(12) United States Patent
Bold et al.

(10) Patent No.: US 6,251,911 B1
(45) Date of Patent: Jun. 26, 2001

(54) PYRIMIDINE DERIVATIVES AND PROCESSES FOR THE PREPARATION THEREOF

(75) Inventors: Guido Bold, Gipf-Oberfrick; Jörg Frei, Hölstein, both of (CH); Marc Lang, Mulhouse (FR); Peter Traxler, Schönenbuch (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/269,823

(22) PCT Filed: Sep. 30, 1997

(86) PCT No.: PCT/EP97/05369

§ 371 Date: Apr. 1, 1999

§ 102(e) Date: Apr. 1, 1999

(87) PCT Pub. No.: WO98/14450

PCT Pub. Date: Apr. 9, 1998

(30) Foreign Application Priority Data

Oct. 2, 1996 (CH) .................................. 2399/96

(51) Int. Cl.$^7$ ............... C07D 487/04; A61K 31/505
(52) U.S. Cl. ................................. 514/258; 544/262
(58) Field of Search ..................... 544/262; 514/258

(56) References Cited

U.S. PATENT DOCUMENTS 5,686,457   11/1997   Traxler et al. ................ 514/258

FOREIGN PATENT DOCUMENTS

| | | |
|---|---|---|
| 3036390 | 5/1982 | (DE) . |
| 0 773 023 A1 | 5/1997 | (EP) . |
| 0 795 556 A1 | 9/1997 | (EP) . |
| WO 92/20642 | 11/1992 | (WO) . |
| WO 95/19774 | 7/1995 | (WO) . |
| WO 95/19970 | 7/1995 | (WO) . |
| WO 96/10028 | 4/1996 | (WO) . |
| WO 96/31510 | 10/1996 | (WO) . |
| WO 96/40142 | 12/1996 | (WO) . |
| WO 97/02266 | 1/1997 | (WO) . |
| WO 97/27199 | 7/1997 | (WO) . |
| WO 97/34895 | 9/1997 | (WO) . |
| WO 98/07726 | 2/1998 | (WO) . |
| WO 98/14449 | 4/1998 | (WO) . |

OTHER PUBLICATIONS

Girgis N.S. et al., Liebigs Ann. Chem., pp. 2066–2072 (1983).
Jorgensen A. et al., Liebigs Ann. Chem., pp. 142–148 (1985).
Jorgensen A. et al., J. Heterocyclic Chem., vol. 22, p. 859–863 (1985).
Derwent Abstract No. 92-213005-26.
Dow R.L. et al., 209th ACS Meeting Apr. 2nd–7th, Anaheim, Calif, 1995.
Sun L. et al., 209th ACS Meeting Apr. 2nd–7th, Anaheim, Calif, 1995.
Bridges A.G. et al., 86th Annual Meeting, American Association of Cancer Res., Toronto, Ontario, Canda, Mar. 18–22, 1995.
Marquet, J.P. et al., Chimie Therapeutique, No. 6, pp. 427–438 (1971).
Mattson R.J. et al., Synthesis, pp. 217–218 (Mar. 1979).

*Primary Examiner*—Richard L. Raymond
*Assistant Examiner*—Hung Liu
(74) *Attorney, Agent, or Firm*—Joseph J. Borovian

(57) ABSTRACT

4-Amino-1H-pyrazolo[3,4-d]pyrimidine derivatives of formula I

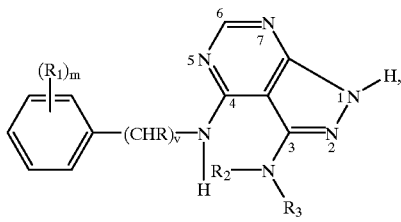

wherein the substituents are as defined in claim 1, are described.

These compounds inhibit the tyrosine kinase activity of the receptor for epidermal growth factor (EGF) and c-erbB2 kinase and can be used as anti-tumor agents.

11 Claims, No Drawings

PYRIMIDINE DERIVATIVES AND PROCESSES FOR THE PREPARATION THEREOF

The invention relates to 4-amino-1H-pyrazolo[3,4] pyrimidine derivatives and intermediates and to processes for the preparation thereof, to pharmaceutical formulations comprising such derivatives, and to the use of those derivatives as medicaments.

The invention relates to 4-amino-1H-pyrazolo[3,4-d] pyrimidine derivatives of formula I

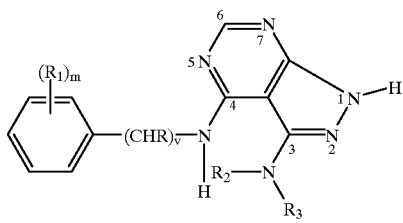

wherein m is an integer from 0 up to and including 3,
v is 0 or 1,
R is hydrogen or lower alkyl,
$R_1$ is halogen, cyano, amino, lower alkanoylamino, lower alkylamino, N,N-di-lower alkylamino, hydroxy, lower alkoxy, lower alkanoyloxy, carboxy, lower alkoxycarbonyl, carbamoyl, N-lower alkyl-carbamoyl, N,N-di-lower alkyl-carbamoyl, or lower alkyl that is unsubstituted or substituted by halogen, cyano, amino, lower alkanoylamino, lower alkylamino, N,N-di-lower alkylamino, hydroxy, lower alkoxy, lower alkanoyloxy, carboxy, lower alkoxycarbonyl, carbamoyl, N-lower alkyl-carbamoyl or by N,N-di-lower alkyl-carbamoyl, it being possible when several phenyl substituents $R_1$ are present for those substituents to be identical or different from one another, and a) $R_2$ is hydrogen and $R_3$ is
α) a radical of formula II

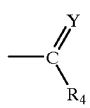

wherein Y is oxygen or sulfur and
$R_4$ is
αα) an alkyl radical that is unsubstituted or substituted by amino, lower alkanoylamino, benzoylamino, benzyloxycarbonylamino, lower alkoxycarbonylamino, phenylamino or by benzylamino and that contains, including the substituents, from 4 to 20 carbon atoms,
αβ) phenylamino, benzylamino, naphthylamino, pyridylmethylamino, or alkylamino having from 4 to 11 carbon atoms, or
αγ) phenyl, or monocyclic heterocyclyl bonded via a carbon atom and having 5 or 6 ring members and from 1 to 4 ring hetero atoms selected from nitrogen, oxygen and sulfur, any phenyl radicals present in the radical $R_4$ being unsubstituted or substituted by one or more radicals selected from nitro, amino, lower alkanoylamino, lower alkylamino, di-lower alkylamino, halogen, cyano, trifluoromethyl, hydroxy, lower alkoxy, lower alkanoyloxy, carboxy, lower alkoxycarbonyl, carbamoyl, N-lower alkyl-carbamoyl, methylenedioxy and lower alkyl, it being possible when several phenyl substituents are present for those substituents to be identical or different from one another, β) unsubstituted alkyl having from 5 to 12 carbon atoms or lower alkyl substituted by
βα) unsubstituted or lower-alkyl-substituted monocyclic heterocyclyl having 5 or 6 ring members and from 1 to 4 ring hetero atoms selected from nitrogen, oxygen and sulfur,
β62 ) phenyl substituted by
i) phenyl,
ii) unsubstituted or chloro-substituted phenoxy or iii) unsubstituted or lower-alkyl-substituted monocyclic heterocyclyl having 5 or 6 ring members and from 1 to 4 ring hetero atoms selected from nitrogen, oxygen and sulfur,
βγ) naphthyl,
βδ) cycloalkyl having from 3 to 8 ring members that is unsubstituted or substituted by lower alkyl or by lower alkoxycarbonyl, or
βε) amino, lower alkylamino, di-lower alkylamino, lower alkanoylamino, benzyloxycarbonylamino, lower alkoxycarbonylamino, benzoyl amino, phenylamino, benzylamino, ureido, $N^3$-phenyl-ureido, $N^3$-lower alkyl-ureido, $N^3$,$N^3$-di-lower alkyl-ureido, amino-lower alkanoylamino, (lower alkoxycarbonylamino-lower alkanoyl)-amino, (benzy)oxycarbonylamino-lower alkanoyl)-amino, prolyl-amino, (N-lower alkoxycarbonyl-prolyl)-amino, $N^3$-lower alkyl-thio-ureido, $N^3$-phenyl-thioureido, cyano, guanidino, amidino, toluenesulfonylamino, lower alkanesulfonylamino or unsubstituted or lower-alkyl-substituted monocyclic heterocyclyl-carbonylamino having 5 or 6 ring members and from 1 to 4 ring hetero atoms selected from nitrogen, oxygen and sulfur,
radicals mentioned in section βε) that contain a phenyl radical being unsubstituted or substituted in the phenyl radical by halogen, cyano, nitro, amino, lower alkanoylamino, lower alkylamino, N,N-di-lower alkylamino, hydroxy, lower alkoxy, lower alkanoyloxy, carboxy, lower alkoxycarbonyl, carbamoyl, N-lower alkyl-carbamoyl, N,N-di-lower alkyl-carbamoyl or by lower alkyl, or
γ) a radical of formula III

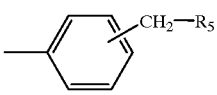

wherein $R_5$ is carboxy-lower alkanoylamino, benzyloxycarbonylamino, ureido, $N^3$-phenyl-ureido, $N^3$-(chloro-phenyl)-ureido, $N^3$-(lower alkoxy-phenyl)-ureido, $N^3$-lower alkyl-ureido, $N^3$,$N^3$-di-lower alkyl-ureido, $N^3$-lower alkyl-thioureido, amino-lower alkanoyl-amino, (lower alkoxycarbonylamino-lower alkanoyl)-amino, (benzyloxycarbonylamino-lower alkanoyl)amino, prolyl-amino, (N-lower alkoxycarbonyl-prolyl)-amino, hydroxy-lower alkanoyl-amino, di-lower alkylamino-methyleneamino, succinimido, phthalimido, guanidino or amidino,
δ) unsubstituted or lower-alkyl-substituted monocyclic heterocyclyl bonded via a ring carbon atom and having 5 or 6 ring members and from 1 to 4 ring hetero atoms selected from nitrogen, oxygen and sulfur, or
ε) lower alkanesulfonyl or unsubstituted or lower-alkyl-substituted benzenesulfonyl, or
b) $R_2$ and $R_3$ together are
di-lower alkylamino-methyleneamino, or a substituted or unsubstituted alkylene or alkenylene radical having up to 15 carbon atoms, wherein from 1 to 3 carbon atoms may have been replaced by oxygen, sulfur or nitrogen,
and salts, solvates and tautomers thereof.

The general terms used hereinabove and hereinbelow preferably have the following meanings within the scope of the present Application:

The term "lower" denotes a radical having up to and including a maximum of 7, especially up to and including a maximum of 4, and more especially 1 or 2, carbon atoms.

When m is 0, the phenyl ring does not carry any substituents $R_1$. Preferably, m is an integer from 0 up to and including 2. When m is 1, the phenyl substituent $R_1$ is primarily in the 4-position, i.e. in the para-position, or especially in the 3-position, i.e. in the meta-position.

When m is 2, the two phenyl substituents $R_1$ are preferably in the 3- and 4-positions.

When v is 0, the $(R_1)_m$ phenyl radical is bonded directly to the nitrogen atom in the 4-position of the 1H-pyrazolo[3,4-d]pyrimidine derivative.

Halogen $R_1$ is fluorine, bromine, iodine or preferably chlorine.

Lower alkoxy $R_1$ is, for example, methoxy.

Lower alkanoyloxy $R_1$ is, for example, acetoxy.

Lower alkoxycarbonyl $R_1$ is, for example, methoxycarbonyl.

N-Lower alkyl-carbamoyl $R_1$ is, for example, N-methyl-carbamoyl.

Amino- or cyano-substituted lower alkyl $R_1$ is, for example, —$(CH_2)_x$—$NH_2$ or —$(CH_2)_x$—CN, respectively, wherein x is in each case from 1 to 4.

Unsubstituted or lower-alkyl-substituted monocyclic heterocyclyl having 5 or 6 ring members and from 1 to 4 ring hetero atoms selected from nitrogen, oxygen and sulfur is preferably bonded via a ring carbon atom, for example pyridyl, such as 2-, 3- or 4-pyridyl, lower alkyl-pyridyl, such as 2-methyl-pyrid-6-yl, lower alkyl-pyridinium-yl, such as N-methyl-pyridinium-4-yl, thienyl, such as 3-thienyl, thiazolyl, such as 2- or 5-thiazolyl, pyrrolyl, such as 2-pyrrolyl, N-lower alkyl-pyrrolyl, such as N-lower alkyl-pyrrol-2-yl, imidazolyl, such as 2- or 4-imidazolyl, furyl, such as 2- or 3-furyl, tetrazolyl, such as 5-tetrazolyl, or lower alkyl-tetrazolyl, such as 2-lower alkyl-tetrazol-5-yl.

Unsubstituted or lower-alkyl-substituted monocyclic heterocyclylcarbonylamino having 5 or 6 ring members and from 1 to 4 ring hetero atoms selected from nitrogen, oxygen and sulfur preferably contains one of the above-mentioned heterocyclyl radicals and is, for example, furoylamino, such as especially 2-furoylamino.

Amidino is a radical of the formula —C(=NH)—$NH_2$.

Guanidino is a radical of the formula —NH—C(=NH)—$NH_2$.

Ureido is a radical of the formula —NH—C(=O)—$NH_2$.

$N^3$-Lower alkyl-ureido is a radical of the formula —NH—C(=O)—NH-lower alkyl, preferably $N^3$-ethyl-ureido.

$N^3,N^3$-Di-lower alkyl-ureido is a radical of the formula —NH—C(=O)—N(lower alkyl)$_2$.

$N^3$-Phenyl-ureido is a radical of the formula —NH—C(=O)—NH-phenyl.

$N^3,N^3$-Diphenyl-ureido is a radical of the formula —NH—C(=O)—N(phenyl)$_2$.

Thioureido is a radical of the formula -NH-C(=S)-$NH_2$.

$N^3$-Lower alkyl-thioureido is a radical of the formula -NH-C(=S)-NH-lower alkyl, preferably $N^3$-methyl-thioureido.

$N^3,N^3$-Di-lower alkyl-thioureido is a radical of the formula —NH—C(=S)-N(lower alkyl)$_2$.

Lower alkoxycarbonylamino is, for example, methoxycarbonylamino, ethoxycarbonylamino, isopropyloxycarbonylamino or 2-methyl-propyloxycarbonylamino.

Morpholine-4-carbonyl is also referred to as morpholinocarbonyl.

4-Lower alkyl-piperazine-1-carbonyl is preferably 4-methyl-piperazine-1-carbonyl.

Lower alkylsulfonylamino is preferably methylsulfonylamino, ethylsulfonylamino or isopropylsulfonylamino.

The radical of the formula —N=C—N(CH$_3$)$_2$ is referred to as di-lower alkylamino-methyleneamino. Corresponding radicals that contain, instead of the di-lower alkylamino radical, piperidino, 4-lower alkyl-piperazino or morpholino are referred to as (piperidino etc.)-methyleneamino radicals, for example piperidino-methyleneamino.

Lower alkanoylamino is, for example, formylamino or acetylamino.

A substituted or unsubstituted alkylene or alkenylene radical having up to 15 carbon atoms, wherein from 1 to 3 carbon atoms may have been replaced by oxygen, sulfur or nitrogen, which is represented by $R_2$ and $R_3$ together, is branched or unbranched and has preferably not more than 10 carbon atoms, and generally not more than 5 carbon atoms, for example 4 or 5 carbon atoms, the carbon atoms present in any substituents not being included in the count. The substituents can be located both on a carbon atom and, especially, on a nitrogen atom. Preferred radicals are, for example, 1,2-ethylene, propane-1,3-diyl, butane-1,4-diyl, pentane-1,5-diyl, 3-(3-amino-propionyl)-3-aza-pentane-1,5-diyl, 2-amino-butane-1,4-diyl, 1-aminomethyl-butane-1,4-diyl, 1-hydroxymethyl-butane-1,4-diyl, 3-hydroxypentane-1,5-diyl, 1-hydroxy-hexane-1,5-diyl, 3(2-amino-ethyl)-pentane-1,5-diyl, 3-aza-pentane-1,5-diyl (—$CH_2$—$CH_2$—NH—$CH_2$—$CH_2$—), 3-aza-2,4-dimethyl-pentane-1,5-diyl (—$CH_2$—CH[$CH_3$]—NH—CH[$CH_3$]—$CH_2$—), 3-amino-3-aza-pentane-1,5-diyl (—$CH_2$—$CH_2$—N[$NH_2$]—$CH_2$—$CH_2$—), 1-aza-pentane-1,5-diyl, 1-aza-1-toluoylaminocarbonyl-pentane-1,5-diyl, 1-aza-1-(methylamino-thiocarbonyl)-pentane-1,5-diyl, 1-aza-1-(tert-butylamino-carbonyl)-pentane-1,5-diyl, 1-aza-1-(cyclohexylamino-carbonyl)-pentane-1,5-diyl, 3-aza-1-hydroxy-heptane-3,7-diyl, 3-aza-1-cyano-heptane-3,7-diyl, 1-amino-3-aza-heptane-3,7-diyl, 3-(2-amino-ethyl)-3-aza-pentane-1,5-diyl (—$CH_2$—$CH_2$—N[—$CH_2$—$CH_2$—$NH_2$]—$CH_2$—$CH_2$—), 1-carbamoyl-butane-1,4-diyl, 2-formylamino-pentane-1,4-diyl, 2-aza-butadiene-1,4-diyl (—CH=CH—N=CH—), 2-aza-3-hydroxymethyl-butadiene-1,4-diyl (—CH=C[$CH_2$OH]—N=CH—) and 2-aza-1-hydroxy-1-(4-methoxy-phenyl-amino)-heptane-2,7-diyl {—$(CH_2)_4$—N[—CH(OH)—NH—$C_6H_4$—$OCH_3$]—}. Especially preferred radicals are, for example, 3-oxa-pentane-1,5-diyl, N-lower alkoxycarbonyl-3-aza-pentane-1,5-diyl, N-($C_1$–$C_{12}$alkanoyl)-3-aza-pentane-1,5-diyl, N-benzoyl-3-aza-pentane-1,5-diyl and N-(pyrid-2-yl-carbonyl)-3-aza-pentane-1,5-diyl.

Since compounds of formula I have basic properties, salts of those compounds are acid addition salts with organic or inorganic acids, especially the pharmaceutically acceptable, non-toxic salts. Suitable inorganic acids are, for example, carbonic acid (preferably in the form of the carbonates or hydrogen carbonates); hydrohalic acids, such as hydrochloric acid; sulfuric acid; or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, 2-hydroxybutyric acid, gluconic acid, glucosemonocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetylcystine, pyruvic acid, acetoacetic acid, phosphoserine, 2- or 3-glycerophosphoric acid, glucose-6-phosphoric acid, glucose-1-phosphoric acid, fructose-1,6-bis-phosphoric acid, maleic acid, hydroxymaleic acid, methylmaleic acid, cyclohexanecarboxylic acid, adamantanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, mandelic acid, cinnamic acid, nicotinic acid, isonicotinic acid, glucuronic acid, galacturonic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. Only salts that are pharmaceutically acceptable and non-toxic (at the appropriate dosages) are used therapeutically and those salts are therefore preferred.

Under certain conditions, e.g. when dissolved in certain solvents, it is possible for the compounds of the formula I and intermediates used for their preparation that contain a pyrazole moiety to be present to some extent in a tautomeric form wherein the hydrogen atom normally located on the nitrogen atom in position 1 is located instead on another suitable nitrogen atom, e.g. the nitrogen in position 2, 5 or 7. The invention relates also to those tautomers.

The compounds of formula I have valuable pharmacologically useful properties. In particular they exhibit specific inhibitory activities that are of pharmacological interest. They are effective especially as protein tyrosine kinase inhibitors and/or (furthermore) as inhibitors of protein serine/threonine kinases; they exhibit, for example, powerful inhibition of the tyrosine kinase activity of the receptor for epidermal growth factor (EGF) and of c-erbB2 kinase. Those receptor-specific enzyme activities play a key role in signal transmission in a large number of mammalian cells, including human cells, especially epithelial cells, cells of the immune system and cells of the central and peripheral nervous system. For example, in various cell types, EGF-induced activation of receptor-associated protein tyrosine kinase (EGF-R-PTK) is a prerequisite for cell division and hence for the proliferation of the cell population. The administration of EGF-receptor-specific tyrosine kinase inhibitors thus inhibits the proliferation of the cells. The same applies analogously to the other protein kinases mentioned hereinbefore and hereinafter.

The inhibition of EGF-receptor-specific protein tyrosine kinase (EGF-R-PTK) can be demonstrated using known methods, for example using the recombinant intracellular domain of the EGF-receptor (EGF-R ICD; see, for example, E. McGlynn et al. Europ. J. Biochem. 207, 265–275 (1992)). Compared with the control without inhibitor, the compounds of formula I inhibit the enzyme activity by 50% ($IC_{50}$), for example in a concentration of from 0.0005 to 5 $\mu$M, especially from 0.001 to 0.1 $\mu$M.

In the micromolar range too, the compounds of formula I exhibit, for example, inhibition of the cell growth of EGF-dependent cell lines, for example the epidermoid BALB/c mouse keratinocyte cell line (see Weissmann, B. A., and Aaronson, S. A., Cell 32, 599 (1983)) or the A431 cell line, which are recognized useful standard sources of EGF-dependent epithelial cells (see Carpenter, G., and Zendegni, J. Anal. Biochem. 153, 279–282 (1985)). In a known test method (see Meyer et al., Int. J. Cancer 43, 851 (1989)), the inhibitory activity of the compounds of formula I is determined, briefly, as follows: BALB/MK cells (10 000/microtiter plate well) are transferred to 96-well microtiter plates. The test compounds (dissolved in DMSO) are added in a series of concentrations (dilution series) in such a manner that the final concentration of DMSO is not greater than 1% (v/v). After the addition, the plates are incubated for three days during which the control cultures without test compound are able to undergo at least three cell-division cycles. The growth of the MK cells is measured by means of methylene blue staining: after the incubation the cells are fixed with glutaraldehyde, washed with water and stained with 0.05% methylene blue. After a washing step the stain is eluted with 3% HCl and the optical density per well of the microtiter plate is measured using a Titertek multiskan at 665 nm. $IC_{50}$ values are determined by a computer-aided system using the formula:

$$IC_{50}=[(OD_{test}-OD_{start})/(OD_{control}-OD_{start})]\times 100.$$

The $IC_{50}$ value in those experiments is given as that concentration of the test compound in question that results in a cell count that is 50% lower than that obtained using the control without inhibitor. The compounds of formula I exhibit inhibitory activity in the micromolar range, for example an $IC_{50}$ of approximately from 0.1 to 10 $\mu$M, specially from 0.4 to 4 $\mu$M.

The compounds of formula I exhibit inhibition of the growth of tumor cells also in vivo, as shown, for example, by the test described below: the test is based on inhibition of the growth of the human epidermoid carcinoma A431 (ATCC No. CRL 1555; American Type Culture Collection, Rockville, Md., USA; see Santon, J. B., et al. Cancer Research 46, 4701–4705 (1986) and Ozawa, S., et al., Int. J. Cancer 40, 706–710 (1987)), which is transplanted into female BALB/c nude mice (Bomholtgard, Denmark). That carcinoma exhibits a growth that correlates with the extent of the expression of EGF-receptor. In the experiment, tumor having a volume of approximately 1 $cm^3$ cultured in vivo are surgically removed from experimental animals under sterile conditions. The tumors are comminuted and suspended in 10 volumes (w/v) of phosphate-buffered saline. The suspension is injected s.c. (0.2 ml/mouse in phosphate-buffered saline) into the left flank of the animals. Alternatively, $1\times 10^6$ cells from an in vitro culture can be injected in 0.2 ml of phosphate-buffered saline. Treatment with test compounds of formula I is started 5 or 7 days after the transplant, when the tumors have reached a diameter of 4–5 mm. The test compound in question is administered (in different doses for different animal groups) once a day for 15 successive days. The tumor growth is determined by measuring the diameter of the tumors along three axes that are perpendicular to each other. The tumor volumes are calculated using the known formula $p\times L\times D^2/6$ (see Evans, B. D., et al., Brit J. Cancer 45, 466–468 (1982)). The results are given as treatment/control percentages (T/C$\times$100 =T/C %). At a dose of from 3 to 50 mg/kg active ingredient, distinct inhibition of the tumor growth is found, for example T/C % values of less than 10, which indicates strong inhibition of tumor growth.

In addition to or instead of inhibiting EGF-receptor protein tyrosine kinase, the compounds of formula I also inhibit other protein tyrosine kinases that are involved in signal transmission mediated by trophic factors, for example abl kinase, kinases from the family of the src kinases, especially c-src kinase (IC$_{50}$, for example, from 1 to 10 μM) and c-erbB2 kinase (HER-2), as well as serine/threonine kinases, for example protein kinase C, all of which play a part in growth regulation and transformation in mammalian cells, including human cells.

The inhibition of c-erbB2-tyrosine kinase (HER-2) can be determined, for example, analogously to the method used for EGF-R-PTK (see C. House et al., Europ. J. Biochem. 140, 363–367 (1984)). The c-erbB2 kinase can be isolated, and its activity determined, by means of protocols known per se, for example in accordance with T. Akiyama et al., Science 232, 1644 (1986).

The compounds of formula I which inhibit the tyrosine kinase activity of the receptor for the epidermal growth factor (EGF) or also of the other protein tyrosine kinases mentioned are therefore useful, for example, in the treatment of benign or malignant tumor. They are capable of effecting tumor regression and of preventing the formation of tumor metastases and the growth of micrometastases. They can be used especially in the case of epidermal hyperproliferation (psoriasis), in the treatment of neoplasia of epithelial character, e.g. mammary carcinomas, and in leukemias. In addition, the compounds of formula I can be used in the treatment of tumor disorders of the lungs, the intestine and the skin and in the treatment of disorders of the immune system insofar as several or, especially, individual protein tyrosine kinases and/or (furthermore) protein serine/threonine kinases are involved; those compounds of formula I can also be used in the treatment of disorders of the central or peripheral nervous system insofar as signal transmission by several or, especially, a single protein tyrosine kinase(s) and/or (furthermore) protein serine/threonine kinase(s) is/are involved.

In general, the present invention relates also to the use of the compounds of formula I in the inhibition of the mentioned protein kinases.

The compounds according to the invention can be used both alone and in combination with other pharmacologically active compounds, for example together with inhibitors of the enzymes of polyamine synthesis, inhibitors of protein kinase C, inhibitors of other tyrosine kinases, cytokines, negative growth regulators, for example TGF-β or IFN-β, aromatase inhibitors, antioestrogens and/or cytostatic agents.

In the case of the preferred subjects of the invention mentioned below, general definitions can be replaced by the more specific definitions given at the beginning, where appropriate and expedient.

Preference is given to derivatives of formula I wherein m is an integer from 0 up to and including 3, v is 0 or 1, R is hydrogen or lower alkyl, $R_1$ is halogen, or lower alkyl that is unsubstituted or substituted by halogen, cyano, amino, lower alkanoylamino, lower alkylamino, N,N-di-lower alkylamino, hydroxy, lower alkoxy, lower alkanoyloxy, carboxy, lower alkoxycarbonyl, carbamoyl, N-lower alkyl-carbamoyl or by N,N-di-lower alkyl-carbamoyl, it being possible when several phenyl substituents $R_1$ are present for those substituents to be identical or different from one another, and a) $R_2$ is hydrogen and $R_3$ is α) a radical of formula II

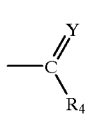

(II)

wherein Y is oxygen or sulfur and $R_4$ is

αα) an alkyl radical that is unsubstituted or substituted by amino, lower alkanoylamino, benzoylamino, benzyloxycarbonylamino, lower alkoxycarbonylamino, phenylamino or by benzylamino and that contains, including the substituents, from 4 to 20 carbon atoms, αβ) phenylamino, benzylamino, naphthylamino, pyridylmethylamino, or alkylamino having from 4 to 11 carbon atoms, or αγ) phenyl, or monocyclic heterocyclyl bonded pia a ring carbon atom, selected from furyl, thienyl and pyridyl, any phenyl radicals present in the radical $R_4$ being unsubstituted or substituted by one or more radicals selected from nitro, amino, lower alkanoylamino, lower alkylamino, di-lower alkylamino, halogen, cyano, trifluoromethyl, hydroxy, lower alkoxy, lower alkanoyloxy, carboxy, lower alkoxycarbonyl, carbamoyl, N-lower alkyl-carbamoyl, methylenedioxy and lower alkyl, it being possible when several phenyl substituents are present for those substituents to be identical or different from one another, β) unsubstituted alkyl having from 5 to 12 carbon atoms or lower alkyl substituted by βα) unsubstituted or lower-alkyl-substituted monocyclic heterocyclyl bonded via a ring carbon atom, selected from pyridyl, thienyl, thiazolyl, pyrrolyl, imidazolyl, furyl and tetrazolyl, ββ) phenyl substituted by i) phenyl, ii) unsubstituted or chloro-substituted phenoxy or iii) unsubstituted or lower-alkyl-substituted monocyclic heterocyclyl bonded via a ring carbon atom, selected from tetrazolyl, pyridyl and thiazolyl, βγ) naphthyl, βδ) cycloalkyl having from 3 to 8 ring members that is unsubstituted or substituted by lower alkyl or by lower alkoxycarbonyl, or βε) amino, lower alkylamino, di-lower alkylamino, lower alkanoylamino, benzyloxycarbonylamino, lower alkoxycarbonylamino, benzoylamino, phenylamino, benzylamino, ureido, $N^3$-phenyl-ureido, $N^3$-lower alkyl-ureido, $N^3$,N-di-lower alkyl-ureido, amino-lower alkanoylamino, (lower alkoxycarbonylamino-lower alkanoyl)-amino, (benzyloxycarbonylamino-lower alkanoyl)-amino, prolyl-amino, (N-lower alkoxycarbonyl-prolyl)-amino, $N^3$-lower alkyl-thioureido, $N^3$-phenyl-thioureido, cyano, guanidino, amidino, toluenesulfonylamino, lower alkanesulfonylamino or furoylamino, radicals mentioned in section βε) that contain a phenyl radical being unsubstituted or substituted in the phenyl radical by halogen, cyano, nitro, amino, lower alkanoylamino, lower alkylamino, N,N-di-lower alkylamino, hydroxy, lower alkoxy, lower alkanoyloxy, carboxy, lower alkoxycarbonyl, carbamoyl, N-lower alkyl-carbamoyl, N,N-di-lower alkyl-carbamoyl or by lower alkyl, or γ) a radical of formula III

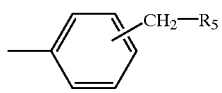

(III)

wherein R$_5$ is carboxy-lower alkanoylamino, benzyloxycarbonylamino, ureido, N$^3$-phenyl-ureido, N$^3$,N$^3$(chloro-phenyl)-ureido, N$^3$-(lower alkoxy-phenyl)-ureido, N$^3$-lower alkyl-ureido, N$^3$,N$^3$-di-lower alkylureido, N$^3$-lower alkyl-thioureido, amino-lower alkanoyl-amino, (lower alkoxycarbonylamino-lower alkanoyl)-amino, (benzyloxycarbonylamino-lower alkanoyl)-amino, prolyl-amino, (N-lower alkoxycarbonyl-prolyl)-amino, hydroxy-lower alkanoyl-amino, di-lower alkylamino-methyleneamino, succinimido, phthatimido, guanidino or amidino, δ) pyridyl, or ε) lower alkanesulfonyl or unsubstituted or lower-alkyl-substituted benzenesulfonyl, or b) R$_2$ and R$_3$ together are di-lower alkylamino-methyleneamino, 1,2-ethylene, propane-1,3-diyl, butane-1,4-diyl, pentane-1,5-diyl, 3-(3-amino-propionyl)-3-aza-pentane-1,5-diyl, 2-amino-butane-1,4-diyl, 1-aminomethyl-butane-1,4-diyl, 1-hydroxymethyl-butane-1,4-diyl, 3-hydroxy-pentane-1,5-diyl, 1-hydroxy-hexane-1,5-diyl, 3-(2-amino-ethyl)-pentane-1,5-diyl, 3-aza-pentane-1,5-diyl (—CH$_2$—CH$_2$—NH—CH$_2$—CH$_2$—), 3-aza-2,4-dimethyl-pentane-1,5-diyl (—CH$_2$—CH[CH$_3$]—NH—CH[CH$_3$]—CH$_2$—), 3-amino-3-aza-pentane-1,5-diyl (—CH$_2$—CH$_2$—N[NH$_2$]—CH$_2$—CH$_2$—), 1-aza-pentane-1,5-diyl, 1-aza-1-toluylaminocarbonyl-pentane-1,5-diyl, 1-aza-1-(methylamino-thiocarbonyl)-pentane-1,5-diyl, 1-aza-1-(tert-butylamino-carbonyl)-pentane-1,5-diyl, 1-aza-1-(cyclohexylaminocarbonyl)-pentane-1,5-diyl, 3-aza-1-hydroxy-heptane-3,7-diyl, 3-aza-1-cyano-heptane-3,7-diyl, 1-amino-3-aza-heptane-3,7-diyl, 3-(2-aminoethyl)-3-aza-pentane-1,5-diyl (—CH$_2$—CH$_2$—N[—CH$_2$—CH$_2$—NH$_2$]—CH$_2$—CH$_2$—), 1-carbamoyl-butane-1,4-diyl, 2-tormylamino-pentane-1,4-diyl, 2-aza-butadiene-1,4-diyl (—CH=CH—N=CH—), 2-aza-3-hydroxymethyl-butadiene-1,4-diyl (—CH=C[CH$_2$OH]—N=CH—), 2-aza-1-hydroxy-1-(4-methoxy-phenyl-amino)-heptane-2,7-diyl {—(CH$_2$)$_4$—N[—CH(OH)—NH—C$_6$H$_4$—OCH$_3$]}, 3-oxa-pentane-1,5-diyl, N-lower alkoxycarbonyl-3-aza-pentane-1,5-diyl, N-(C$_1$–C$_{12}$alkanoyl)-3-aza-pentane-1,5-diyl, N-benzoyl-3-aza-pentane-1,5-diyl or N-(pyrid-2-yl-carbonyl)-3-aza-pentane-1,5-diyl, and salts, solvates and tautomers thereof.

Special preference is given to derivatives of formula I wherein m is an integer from 0 up to and including 2, v is 0 or 1, R is hydrogen or lower alkyl, R$_1$ is halogen or lower alkyl, it being possible when several phenyl substituents R$_1$ are present for those substituents to be identical or different from one another, and a) R$_2$ is hydrogen and R$_3$ is α) a radical of formula II

(II)

wherein Y is oxygen or sulfur and

R$_4$ is

αα) unsubstituted C$_4$–C$_7$alkyl or a lower alkyl radical that is unsubstituted or substituted by amino, lower alkanoylamino, benzoylamino, benzyloxycarbonylamino, lower alkoxycarbonylamino, phenylamino or by benzylamino and that contains, including the substituents, from 4 to 20 carbon atoms, αβ) phenylamino, benzylamino, naphthylamino, pyridylmethylamino, or alkylamino having from 4 to 11 carbon atoms, or αγ) phenyl, or monocyclic heterocyclyl bonded via a ring carbon atom, selected from furyl, thienyl and pyridyl, any phenyl radicals present in the radical R$_4$ being unsubstituted or substituted by one or more radicals selected from halogen, methylenedioxy and lower alkyl, it being possible when several phenyl substituents are present for those substituents to be identical or different from one another, β) unsubstituted alkyl having from 5 to 12 carbon atoms or lower alkyl substituted by βα) unsubstituted or lower-alkyl-substituted monocyclic heterocyclyl that is bonded via a ring carbon atom and selected from pyridyl, thienyl, thiazolyl, pyrrolyl, imidazolyl, furyl and tetrazolyl, ββ) phenyl substituted by i) phenyl, ii) unsubstituted or chloro-substituted phenoxy or iii) unsubstituted or lower-alkyl-substituted monocyclic heterocyclyl that is bonded via a ring carbon atom and selected from tetrazolyl, pyridyl and thiazolyl, βγ) naphthyl, βδ) cycloalkyl having from 3 to 8 ring members that is unsubstituted or substituted by lower alkyl or by lower alkoxycarbonyl, or βε) amino, lower alkylamino, di-lower alkylamino, lower alkanoylamino, benzyloxycarbonyl. amino, lower alkoxycarbonylamino, benzoylamino, phenylamino, benzylamino, ureido, N$^3$-phenyl-ureido, N$^3$-lower alkyl-ureido, N$^3$,N$^3$-di-lower alkyl-ureido, amino-lower alkanoylamino, (lower alkoxycarbonylamino-lower alkanoyl)-amino, (benzyloxycarbonylamino-lower alkanoyl)-amino, prolyl-amino, (N-lower alkoxycarbonyl-prolyl)-amino, N$^3$-lower alkyl-thioureido, N$^3$-phenyl-thioureido, cyano, guanidino, amidino, toluenesulfonylamino, lower alkanesulfonylamino or turoylamino, radicals mentioned in section βε) that contain a phenyl radical being unsubstituted or substituted in the phenyl radical by halogen, nitro, amino, lower alkylamino, N,N-di-lower alkylamino or by lower alkyl, or γ) a radical of formula III

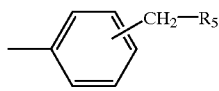
(III)

wherein $R_5$ is carboxy-lower alkanoylamino, benzyloxycarbonyiamino, ureido, $N^3$-phenyl-ureido, $N^3$-(chloro-phenyl)-ureido, $N^3$-(lower alkoxy-phenyl)-ureido, $N^3$-lower alkyl-ureido, $N^3,N^3$-di-lower alkyl-ureido, $N^3$-lower alkyl-thioureido, amino-lower alkanoyl-amino, (lower alkoxycarbonylamino-lower alkanoyl)-amino, (benzyloxycarbonylamino-lower alkanoyl)-amino, prolyl-amino, (N-lower alkoxycarbonyl-prolyl)-amino, hydroxy-lower alkanoyl-amino, di-lower alkylamino-methyleneamino, succinimido, phthalimido, guanidino or amidino, δ) pyridyl, or ε) lower alkanesulfonyl or unsubstituted or lower-alkyl-substituted benzenesulfonyl, or b) $R_2$ and $R_3$ together are di-lower alkylamino-methyleneamino, 3-oxa-pentane-1,5-diyl, N-lower alkoxycarbonyl-3-aza-pentane-1,5-diyl, N-($C_1$–$C_{12}$alkanoyl)-3-aza-pentane-1,5-diyl, N-benzoyl-3-aza-pentane-1,5-diyl or N-(pyrid-2-yl-carbonyl)-3-aza-pentane-1,5-diyl, and salts, solvates and tautomers thereof.

Greatest preference is given to the compounds of formula I described in the Examples and their pharmaceutically acceptable salts and solvates thereof.

The compounds of formula I and their salts, solvates and tautomers can be prepared in a manner known per se.

The preparation process according to the invention is as follows:

a) a compound of formula IV

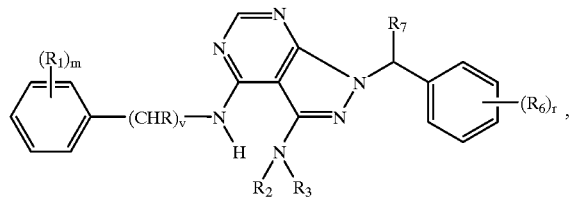
(IV)

wherein $R_7$ is hydrogen or methyl, $R_6$ is alkoxy having from 1 to 3 carbon atoms or nitro, r is an integer from 0 to 2, and the other substituents and symbols are as defined above, is treated with a suitable Lewis acid, or b) a compound of formula V

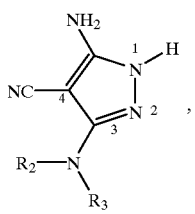
(V)

wherein the symbols are as defined above, is reacted with an amine of formula VI

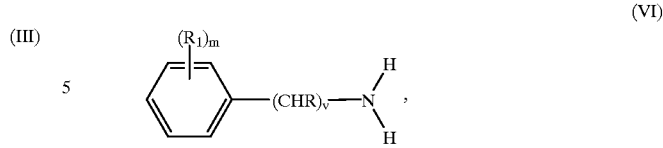
(VI)

wherein v is 1 and the other symbols are as defined above, or with a salt thereof, in the presence of formic acid, or c) a compound of formula V

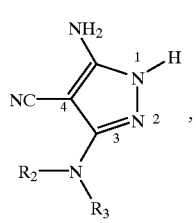
(V)

wherein the symbols are as defined above, is reacted with a formamide derivative of formula VII

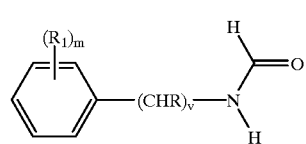
(VII)

wherein v is 1 and the other symbols are as defined above, or d) a compound of formula VIII

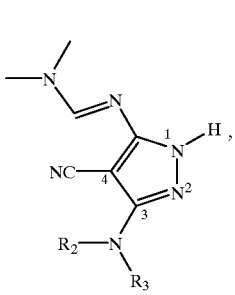
(VIII)

wherein the symbols are as defined above, is reacted with an amine of formula VI

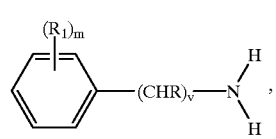
(VI)

wherein v is 0 or 1 and the other symbols are as defined above, or with a salt thereof, or e) a compound of formula IX

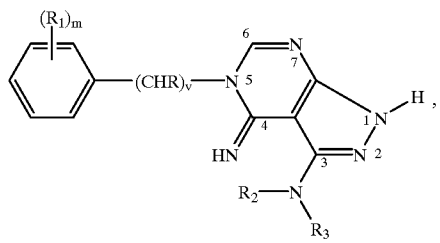

(IX)

wherein v is 0 and the other symbols are as defined above, is subjected to the conditions of a Dimroth rearrangement, and, if desired, a compound of formula I obtainable in accordance with any one of processes a) to e) is converted into its salt, or a resulting salt of a compound of formula I is converted into the free compound.

Further possible ways of preparing compounds of formula I are illustrated by way of example in the Examples section and will be apparent to the person skilled in the art by generalization of the Examples and the use of expert knowledge.

The procedure for carrying out those process variants and the preparation of starting materials are described in greater detail below:

General Remarks:

If necessary, interfering functional groups in starting materials are protected in a manner known per se prior to the reaction by readily removable protecting groups which are removed again when the reaction is over.

Process a):

When $R_7$ is hydrogen, a suitable Lewis acid is especially aluminum chloride. The reaction is carried out in an inert organic solvent, for example a hydrocarbon, such as preferably an aromatic hydrocarbon, such as especially benzene or toluene, at a temperature of from room temperature (about 20° C.) to +200° C., if necessary under protective gas, such as argon, and/or elevated pressure, preferably at the boiling temperature of the solvent used, that is to say under reflux. When $R_7$ is methyl, the reaction mixture is boiled preferably with polyphosphoric acid.

The starting material of formula IV is obtained as follows: first a compound of formula X

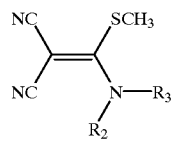

(X)

is reacted with a hydrazine derivative of formula XI

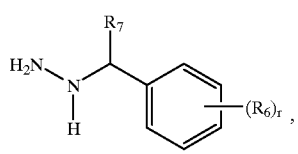

(XI)

wherein $R_7$ is hydrogen or methyl, $R_6$ is alkoxy having from 1 to 3 carbon atoms or nitro and r is an integer from 0 to 2, or with a salt thereof, to form a pyrazole derivative of formula XII

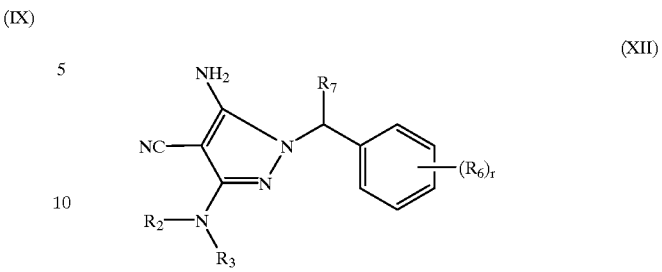

(XII)

wherein the substituents are as defined above. For example, there is used as starting material a methanolic solution of a hydrazine derivative of formula XI in the form of the dihydrochloride to which there are added first, with cooling, for example with ice, a methanolic sodium methanolate solution and then, at room temperature, a solution of a compound of formula X in a suitable anhydrous alcohol, such as absolute ethanol. The reaction mixture is then heated at reflux for several hours.

The resulting compound of formula XII is reacted with formic acid, with formation of the pyrimidine ring, to form a compound of formula XIII

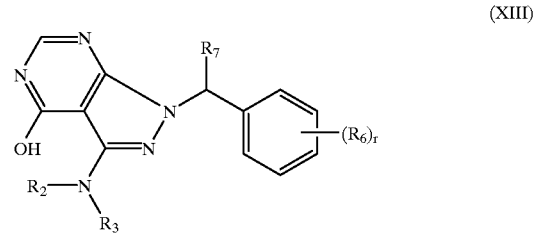

(XIII)

wherein the substituents are as defined above. Preferably a compound of formula XII is heated at reflux for several hours in 85% aqueous formic acid.

From a compound of formula XII there is obtained with phosphoryl chloride (phosphorus oxychloride, POCl₃) or phosphorus trichloride (PCl₃), with replacement of the hydroxy group by chlorine, a compound of formula XIV

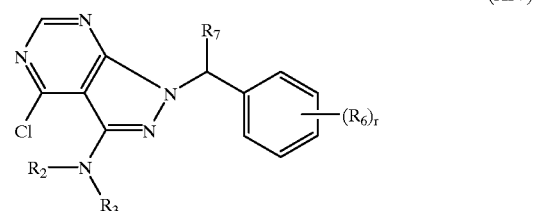

(XIV)

wherein the substituents are as defined above. Preferably a compound of formula XII is heated at reflux for several hours in phosphoryl chloride under protective gas, such as argon.

The compound of formula XIV is then reacted with an aniline derivative of formula XV

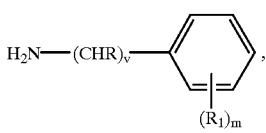

(XV)

wherein the symbols are as defined above, preferably in a suitable solvent, such as a suitable alcohol, for example ethanol, under protective gas, such as nitrogen, at elevated temperature, for example under reflux, to form the desired starting material of formula IV.

The starting material of formula X is obtained, for example, by reaction of 3,3-bis-methylmercapto-2-cyano-acrylonitrile of formula XVI

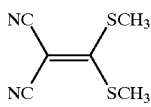

(XVI)

with an amine of formula XVII

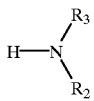

(XVII)

wherein the symbols are as defined above. The above-mentioned 3,3-bis-methylmercapto-2-cyano-acrylonitrile of formula XVI is described under the name "2,2-bis-methylmercapto-1-cyano-acrylonitrile" by R. Gompper and W. Tbpel, Chem. Ber. 95, 2861–2870, especially on page 2868, center, and can be prepared at a temperature of from 5 to 20° C. by an addition reaction between malonic acid dinitrile of the formula $CH_2(CN)_2$ and carbon disulfide in the presence of sodium methanolate in methanol, followed by methylation of the intermediate so obtained with dimethyl sulfate.

Process b):

The starting material of formula VI can be used in the form of a salt, for example in the form of the acetate. In addition to formic acid it is also possible to add further acids, such as glacial acetic acid. The reaction is carried out at elevated temperature, preferably at from 100 to 250° C., such as especially at 200° C.

The starting material of formula V is obtained from a compound of formula X by reaction with hydrazine in a suitable solvent, such as a suitable alkanol, such as especially methanol, for example at reflux temperature.

Process c):

The reaction is carried out at elevated temperature, preferably at from 100 to 250° C., such as especially at 200° C., in the presence or, where possible, in the absence of a solvent, that is to say the formamide derivative of formula VII can act simultaneously as solvent.

Process d):

The reaction is carried out at elevated temperature, preferably at from 50 to 180° C., such as especially at 120° C., in the presence or, where possible, in the absence of a solvent, that is to say the amine derivative of formula VI can act simultaneously as solvent. When v is 0, the amine derivative of formula VI is used preferably in the form of a salt, for example in the form of the hydrochloride. When v is 1, the amine derivative of formula VI is used preferably in the form of the free amine.

The starting material of formula VII is obtained from a compound of formula V by reaction with a suitable dimethylformamide acetal, such as N,N-dimethylformamide diethyl acetal, in a suitable solvent, such as a suitable aromatic hydrocarbon, such as especially toluene, at elevated temperature, preferably at from 50 to 180° C., such as especially under reflux.

Process e):

The Dimroth rearrangment is carried out at elevated temperature, for example at from 70 to 200° C., preferably at from 80 to 150° C., for example under reflux, in a suitable water-containing solvent mixture, for example a mixture of water and a suitable ether, such as a cyclic ether, for example dioxane, for example a dioxane/water mixture in a ratio by volume of 1:1.

The imine of formula IX is obtained, for example, from a compound of formula V in two steps as follows:

In the first step, a compound of formula V is reacted with triethyl orthoformate of the formula $HC(OC_2H_5)_3$ to form an ethoxymethyeneamino compound of formula XVIII

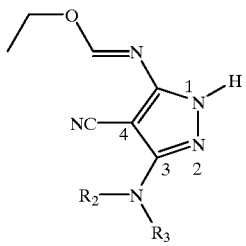

(XVIII)

wherein the symbols are as defined above.

The reaction is carried out at elevated temperature, preferably at from 50 to 180° C., such as especially at 120° C., the triethyl orthoformate acting simultaneously as solvent. The ethanol formed by the reaction is distilled off continuously from the reaction mixture.

In the second step, the resulting compound of formula XVIII is reacted with an amine of formula VI, wherein v is 0 or 1 and the other symbols are as defined above, to form the desired imine of formula IX. This reaction is carried out in a suitable solvent, such as a suitable alcohol, for example an alkanol, such as especially ethanol, at elevated temperature, preferably at from 50 to 180° C., such as especially at from 70 to 120° C., for example at reflux temperature.

Alternatively, the imine of formula IX is obtained directly from a compound of formula VIII by reaction with an amine of formula VI [similarly to process d)] in admixture with the end product of formula I. This reaction is carried out in a suitable solvent, such as a suitable alcohol, for example an alkanol, such as especially ethanol, at elevated temperature, preferably at from 50 to 180° C., such as especially at from 70 to 120° C., for example at reflux temperature.

Acid addition salts of compounds of formula I are obtained in a manner known per se, for example by treatment with an acid or a suitable anion exchange reagent.

Acid addition salts can be converted into the free compounds in customary manner, for example by treatment with a suitable basic agent.

Mixtures of isomers can be separated into the individual isomers in a manner known per se, for example by fractional crystallization, chromatography etc.

The following reaction scheme illustrates some possible ways of synthesizing certain compounds of formula I:

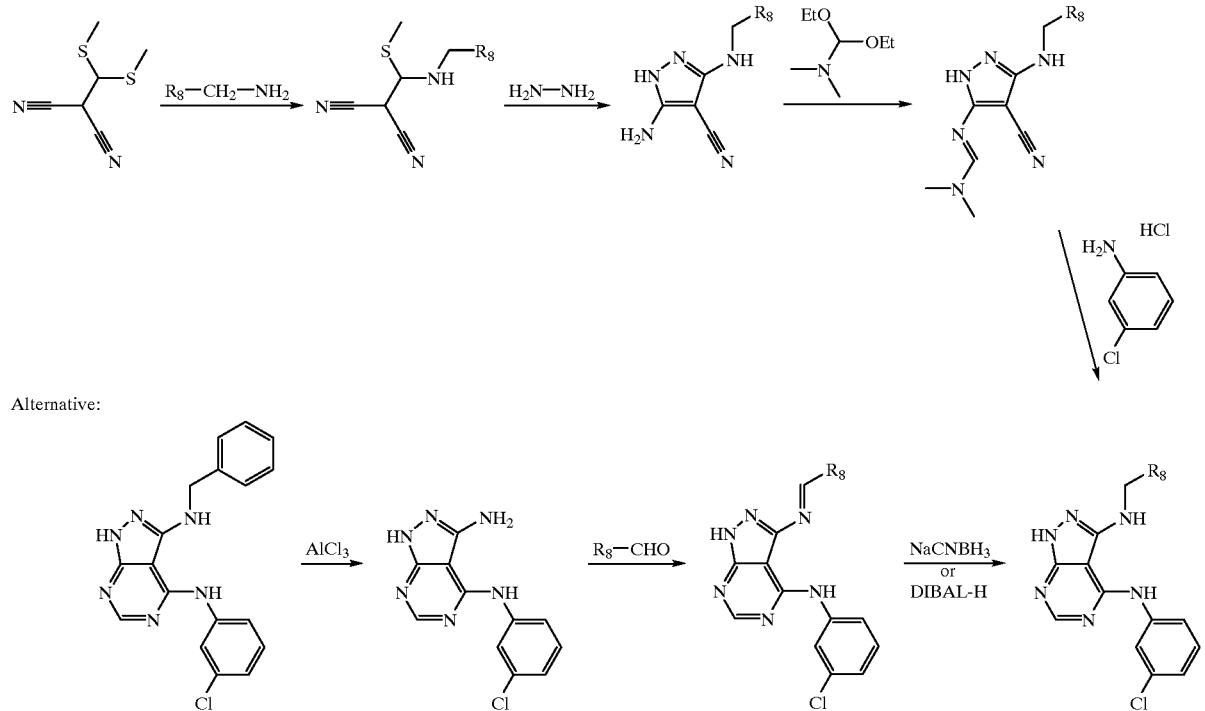

Alternative:

General Process Conditions:

Free compounds of formula I having salt-forming properties obtainable in accordance with the process can be converted into their salts in a manner known per se, for example by treatment with acids or suitable derivatives thereof, for example by the addition of the acid in question to the compound of formula I dissolved in a suitable solvent, for example an ether, such as a cyclic ether, especially dioxane or more especially tetrahydrofuran.

Mixtures of isomers obtainable according to the invention can be separated into the individual isomers in a manner known per se: racemates, for example, by the formation of salts with optically pure salt-forming reagents and separation of the diastereoisomeric mixture so obtainable, for example by means of fractional crystallisation.

The reactions mentioned above can be carried out under reaction conditions known per se, in the absence or, usually, in the presence of solvents or diluents, preferably those solvents or diluents which are inert towards the reagents used and are solvents therefor, in the absence or presence of catalysts, condensation agents (e.g. phosphorus pentoxide) or neutralizing agents, for example bases, especially nitrogen bases, such as triethylamine hydrochloride, depending upon the nature of the reaction and/or the reactants, at reduced, normal or elevated temperature, for example in a temperature range of from approximately −80° C. to approximately 200° C., preferably from approximately −20° C. to approximately 150° C., for example at the boiling point of the solvent used, under atmospheric pressure or in a closed vessel, optionally under pressure, and/or in an inert atmosphere, for example under a nitrogen atmosphere.

The reaction conditions specifically indicated in each case are preferred. Solvents and diluents are, for example, water, alcohols, for example lower alkyl hydroxides, such as methanol, ethanol, propanol or especially butanol, diols, such as ethylene glycol, triols, such as glycerol, or aryl alcohols, such as phenol, acid amides, for example carboxylic acid amides, such as dimethylformamide, dimethylacetamide or 1,3-dimethyl-3,4,5,6-tetrahydro-2(1H)-pyrimidinone (DMPU), carboxylic acids, especially formic acid or acetic acid, amides of inorganic acids, such as hexamethylphosphoric acid triamide, ethers, for example cyclic ethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitrites, such as acetonitrile, acid anhydrides, such as acetic anhydride, esters, such as ethyl acetate, bisalkane sulfines, such as dimethyl sulfoxide, nitrogen heterocycles, such as pyridine, hydrocarbons, for example lower alkanes, such as heptane, or aromatic compounds, such as benzene, toluene or xylene(s), or mixtures of those solvents, it being possible to select whichever solvents are suitable for the above-mentioned reactions.

Customary methods are used for working up the obtainable compounds of formula I or their salts, for example solvolysis of excess reactants; recrystallization; chromatography, for example partition, ion or gel chromatography; partition between an inorganic and an organic solvent phase; single or multiple extraction, especially after acidification or after increasing the basicity or the salt content; drying over hygroscopic salts; digestion; filtration; washing; dissolution; concentration by evaporation (if necessary in vacuo or under a high vacuum); distillation; crystallization, for example of resulting compounds in oil form or from the mother liquor, it also being possible to carry out seeding with a crystal of the end product; or a combination of two or more of the mentioned working-up steps, which may also be used repeatedly, etc.

Starting materials and intermediates can be used in pure form, for example after working-up, as mentioned immediately above, in partially purified form or alternatively without further processing, for example in the form of the crude product.

The compounds, including their salts, can also be obtained in the form of hydrates, or their crystals may include, for example, the solvent used for crystallization. The present invention relates also to such hydrates or solvates of the compounds of formula I and of the starting materials described as forming part of the invention.

As a result of the close relationship between the compounds of formula I in free form and in the form of their salts, hereinabove and hereinbelow any reference to the free compounds or their salts is to be understood, where appropriate and expedient, as including also the salts or the free compounds respectively, provided that the compounds contain salt-forming groups. The same applies analogously to the hydrates and solvates.

In the process of the present invention it is preferable to use those starting materials which result in the novel compounds of formula I described at the beginning as being especially valuable.

The invention relates also to those forms of the process in which a compound obtainable as intermediate at any stage of the process is used as starting material and the remaining process steps are carried out, or in which a starting material is formed under the reaction conditions or is used in the form of a derivative, for example a salt thereof.

Pharmaceutical Compositions, the Preparation Thereof and the Use According to the Invention of Compounds of Formula I and Compositions Comprising Those Compounds As Active Ingredient The present invention relates also to pharmaceutical compositions that comprise one of the compounds of formula I as active ingredient and that can be used especially in the treatment of the diseases mentioned at the beginning. Special preference is given to compositions for enteral, such as nasal, buccal, rectal or especially oral, administration and parenteral, such as intravenous, intramuscular or subcutaneous, administration to warm-blooded animals, especially human beings. The compositions comprise the active ingredient on its own or preferably together with a pharmaceutically acceptable carrier. The dosage of the active ingredient depends on the disease to be treated, and on species, age, weight and individual condition, individual pharmacokinetic conditions, and the mode of administration.

The invention relates also to pharmaceutical compositions for use in a method for the therapeutic treatment of the human or animal body, a process for the preparation thereof (especially as agents in tumor treatment) and a method of treating tumor diseases, especially those mentioned above.

Preference is given to a pharmaceutical composition suitable for administration to a warm-blooded animal, especially a human being, suffering from a disease that is responsive to the inhibition of a protein kinase, especially psoriasis or a tumor, comprising a compound of formula I, or a salt thereof where salt-forming groups are present, in an amount effective in the inhibition of the protein kinase, together with at least one pharmaceutically acceptable carrier.

The pharmaceutical compositions comprise from approximately 1% to approximately 95% active ingredient, forms of administration in single dose form preferably comprising from approximately 20% to approximately 90% active ingredient and forms of administration that are not in single dose form preferably comprising from approximately 5% to approximately 20% active ingredient. Unit dose forms are, for example, dragées, tablets, ampoules, vials, suppositories or capsules. Other forms of administration are, for example, ointments, creams, pastes, foams, tinctures, lipsticks, drops, sprays, dispersions, etc. Examples are capsules comprising from approximately 0.05 g to approximately 1.0 g of the active ingredient.

The pharmaceutical compositions of the present invention are prepared in a manner known per se, for example by means of conventional mixing, granulating, confectioning, dissolving or lyophilizing procedures.

Solutions of the active ingredient, and also suspensions or dispersions, especially isotonic aqueous solutions, dispersions or suspensions, are preferably used, it being possible, for example in the case of lyophilized compositions that contain the active ingredient alone or together with a carrier, for example mannitol, for such solutions, suspensions or dispersions to be made up prior to use. The pharmaceutical compositions may be sterilised and/or may comprise excipients, for example preservatives, stabilizers, wetting agents and/or emulsifiers, solubilizers, salts for regulating the osmotic pressure and/or buffers, and are prepared in a manner known per se, for example by means of conventional dissolving or lyophilizing procedures. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid, or corresponding unsaturated acids, for example oleic acid, elaidic acid, erucic acid, brassidic acid or linoleic acid, if desired with the addition of antioxidants, for example vitamin E, $\beta$-carotene or 3,5-di-tert-butyl-4-hydroxytoluene. The alcohol component of those fatty acid esters has a maximum of 6 carbon atoms and is a mono- or poly-hydric, for example a mono-, di- or tri-hydric, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl paimitate, "Labrafil M 2375" (polyoxyethylene glycerol trioleate, Gattefossé, Paris), "Labrafil M 1944 CS" (unsaturated polyglycolized glycerides prepared by alcoholysis of apricot kernel oil and consisting of glycerides and polyethylene glycol ester; Gattefossé, France), "Labrasol" (saturated polyglycolised glycerides prepared by alcohoiysis of TCM and consisting of glycerides and polyethylene glycol ester; Gattefossé, France) and/or "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into, for example, ampoules or vials and to sealing the containers.

Pharmaceutical compositions for oral administration can be obtained, for example, by combining the active ingredient with one or more solid carriers, it desired granulating a resulting mixture, and processing the mixture or granules, if desired, and if necessary by the addition of additional excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, or alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Dragée cores can be provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures, or, for the production of enteric coatings, solutions of suitable cellulose preparations, such as acetylcellulose phthalate or hydroxypropylmethylcellulose phthalate. Colorings or pigments may be added to the tablets or dragée coatings, for example for identification purposes or to indicate different doses of active ingredient.

Orally administrable pharmaceutical compositions also include dry-filled capsules consisting of gelatin, and also soft, sealed capsules consisting of gelatin and a plasticizer, such as glycerol or sorbitol. The dry-filled capsules may contain the active ingredient in the form of granules, for example in admixture with fillers, such as corn starch, binders and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilisers and detergents, for example of the polyoxyethylene sorbitan fatty acid ester type, may also be added.

Other oral forms of administration are, for example, syrups prepared in customary manner which comprise the active ingredient, for example, in suspended form and in a concentration of about 5% to 20%, preferably about 10%, or in a similar concentration that provides a suitable single dose, for example, when administered in measures of 5 or 10 ml. Also suitable are, for example, powdered or liquid concentrates for the preparation of shakes, for example in milk. Such concentrates may also be packaged in single dose quantities.

Suitable rectally administrable pharmaceutical compositions are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration there are suitable especially aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilisate and can be made into a solution prior to parenteral administration by the addition of suitable solvents.

The invention relates also to a procedure or a method for the treatment of the abovementioned pathological conditions, especially such diseases that are responsive to the inhibition of protein kinases. The compounds of formula I can be administered, prophylactically or therapeutically, as such or in the form of pharmaceutical compositions, preferably in an amount effective against the said diseases, to a warm-blooded animal, for example a human being, requiring such treatment, the compounds being used especially in the form of pharmaceutical compositions. In such treatment an individual of about 70 kg body weight will be administered a daily dose of from approximately 0.1 g to approximately 5 9, preferably from approximately 0.5 9 to approximately 2 g, of a compound of formula I.

The following Examples serve to illustrate the invention.

Unless otherwise indicated, the ratio of solvents to one another is given in parts by volume (v/v).

The short names and abbreviations used have the following meanings:

HPLC Gradients:

$\text{grad}_{20-100/20}$ 20%→100% a) in b) over 20 min.

$\text{grad}_{20-100}$ 20% →100% a) in b) over 13 min+5 min 100% a).

$\text{grad}_{5-40}$ 5%→40% a) in b) over 7.5 min +7 min 40% a).

eluant a): acetonitrile+0.05% TFA; eluant b): water+0.05% TFA.

Column (250×4.6 mm) filled with reversed-phase material C1 8-Nucleosil (5 μm average particle size, silica gel covalently derivatised with octadecylsilanes, Macherey & Nagel, Düren, FRG). Detection by UV absorption at 254 nm. The retention times ($t_{Ret}$) are given in minutes. Flow rate: 1 ml/min.

Abbreviations:

abs. absolute (anhydrous)

Boc tert-butyloxycarbonyl brine saturated sodium chloride solution

DIBAL-H diisobutylaluminum hydride, 1.00M in methylene chloride

DIPE diisopropyl ether

DMEU 1,3-dimethyl-2-imidazolidinone

DMF dimethylformamide

ESI-MS Electro Spray Ionization mass spectroscopy

HV high vacuum min minute(s)

FAB-MS Fast Atom Bombardment mass spectroscopy

NMM N-methylmorpholine

RT room temperature

RV rotary evaporator sat. saturated

TFA trifluoroacetic acid

THIF tetrahydrofuran (dist. over sodium/benzophenone)

Unless otherwise indicated, the crystalline (m.p. >approx. 80° C.) intermediates and end products mentioned in the following Examples are dried under a high vacuum at from 60° C. to a maximum of 1 20° C. for from 6 hours to a maximum of 24 hours.

EXAMPLE 1

With the exclusion of moisture, 171 μl (0.84 mmol) of pivalic anhydride are added at 0° C. to 200 mg (0.767 mmol) of 3-amino-4-(3-chloro-phenylamino)-1H-pyrazolo-[3,4-d] pyrimidine in 4 ml of pyridine/methylene chloride (1:1) and stirred at RT for 3 days. The resulting thick suspension is filtered. The residue is washed with methylene chloride and dried, yielding 4-(3-chloro-phenylamino)-3-(2,2-dimethyl-propionyl-amino)-1H-pyrazolo-[3,4-d]pyrimidine; HPLC: $t_{Ret}(\text{grad}_{20-100/20})$=15.0; FAB-MS: (M+H)$^+$=345.

The starting material is obtained as follows:

Step 1.1:

43.6 ml (400 mmol) of benzylamine are added to a suspension of 68.4 g (400 mmol) of 3,3-bis(methylsulfanyl)-2-cyano-acrylonitrile (Maybridge) in 400 ml of ethyl acetate. The clear solution is slowly heated to 70° C. (→evolution of MeSH!), stirred at that temperature for 1.5 hours, cooled to RT and concentrated by evaporation, yielding crystalline 3-benzylamino-3-methylsulfanyl-2-cyano-acrylonitrile; $^1$H-NMR: (CD$_3$OD) 7.36 (m, 5H), 4.77 (s, 2H), 2.59 (s, 3H).

Step 1.2:

24 ml (0.48 mol) of hydrazine hydrate are added dropwise to a solution of 92 g (0.4 mol) of 3-benzylamino-3-methylsulfanyl-2-cyano-acrylonitrile in 400 ml of methanol, the temperature rising to 40° C. The reaction mixture is slowly heated to boiling (e evolution of MeSH!), boiled for 2 hours, cooled to RT and concentrated by evaporation to a residual volume of ≈200 ml. Dilution with diethyl ether, filtration and washing with diethyl ether yield 5-amino-3-benzylamino-1H-pyrazole-4-carbonitrile [Spectrochimica Acta, 47A, 1635 (1991)]; m.p. 150–152° C.; TLC: R$_f$=0.41 (ethyl acetate).

Step 1.3:

Under a nitrogen atmosphere, a suspension of 74.3 g (348 mmol) of 5-amino-3-benzylamino-1H-pyrazole-4-carbonitrile in 1.0 liter of toluene is boiled under reflux for 2 hours with 70.1 ml (95%; 409 mmol) of N,N-dimethylformamide diethyl acetal. Cooling to RT, filtration with suction and washing with diethyl ether yield N'-(3-benzylamino-4-cyano-1H-pyrazol-5-yl)-N,N-dimethyl-formamidine; m.p. 197–200° C.; TLC: R$_f$=0.50 (ethyl acetate).

Step 1.4:

60 g (0.47 mol) of 3-chloro-aniline are dissolved in 255 ml (0.56 mol) of 2.2N methanolic HCl. Concentration and stirring the residue in diethyl ether yield, after filtration and drying, 3-chloro-aniline hydrochloride.

Step 1.5:

With the exclusion of moisture, 79.2 g (295 mmol) of N'-(3-benzylamino-4-cyano-1 H-pyrazol-5-yl)-N,N-dimethyl-formamidine are suspended in 700 ml of methanol; 60.6 g (369 mmol) of 3-chloro-aniline hydrochloride are added and the mixture is boiled under reflux for 22 hours. The resulting yellow reaction solution is cooled to 50° C. and poured into 2 liters of ice-water, 200 ml of sat. NaHCO$_3$ solution and 1 liter of ethyl acetate. The aqueous phase is separated off and extracted twice with ethyl acetate. The organic phases are washed twice with water, sat. NaHCO$_3$ solution, water and brine, dried (Na$_2$SO$_4$) and concentrated by evaporation to a residual volume of ≈1.5 liters. Seeding and dilution with 300 ml of diethyl ether yield crystalline 3-benzylamino-4-(3-chloro-phenylamino)-1H-pyrazolo[3,4-d]pyrimidine; m.p. 214–217° C.; TLC: R$_f$=0.29 (ethyl acetate:hexane=1:1).

Step 1.6:

Starting with a suspension of 75.8 g (216 mmol) of 3-benzylamino-4-(3-chlorophenylamino)-1H-pyrazolo[3,4-d]pyrimidine in 1.5 liters of benzene, some of the solvent is distilled off for the purpose of removing residual water. Then, with the exclusion of moisture, the suspension is added to 84 g of aluminium chloride (Fluka, Buchs/Switzerland) in 500 ml of benzene and heated at 80° C. for 2.5 hours. The reaction mixture is cooled to RT, the supernatant benzene phase is poured into 2 kg of ice-water (leaving behind a green oily residue), and the solid that separates out is filtered off with suction and washed thoroughly with water (→K$_1$). Using a rotary evaporator, the benzene is evaporated off from the filtrate and the aqueous phase that remains behind is added to the green oily residue together with 1 kg of ice and hydrolyzed at 40° C. for 2 hours. The crystalline product is filtered off with suction and washed with water (K$_2$). K$_1$ and K$_2$ are taken up in 1 liter of methanol, acidified with 4N aqueous HCl and partially concentrated by evaporation. Water is added and the methanol is evaporated off completely. The crystals are filtered off and washed with water. The same purification procedure is repeated using semi-saturated Na$_2$CO$_3$ solution/methanol and water/methanol. Stirring at 50° C. in methanol, precipitation with diethyl ether, filtration and drying yield 3-amino-4-(3-chloro-phenylamino)-1H-pyrazolo[3,4-d]pyrimidine; m.p. 232–234° C.; TLC: R$_f$=0.50 (ethyl acetate).

EXAMPLE 2

Analogously to Example 1, 197 mg (0.84 mmol) of benzoic anhydride are added at 0° C. to 200 mg (0.767 mmol) of 3-amino-4-(3-chloro-phenylamino)-1H-pyrazolo[3,4-d]-pyrimidine (see Step 1.6) in 4 ml of pyridine/methylene chloride (1:1) and reacted for 6 hours at 0° C. and finally for 16 hours at RT to form 3-benzoylamino-4-(3-chloro-phenylamino)-1H-pyrazolo[3,4-d]pyrimidine; HPLC: $t_{Ret}$(grad$_{20-100/20}$)=14.7; FAB MS: (M+H)$_+$=365.

EXAMPLE 3

With the exclusion of air, 83 µl (0.84 mmol) of 2-furancarboxylic acid chloride are added at 0° C. to 200 mg (0.767 mmol) of 3-amino-4-(3-chloro-phenylamino)-1H-pyrazolo[3,4-d]pyrimidine (see Step 1.6) in 4 ml of pyridine/methylene chloride (1:1) and stirred at 0° C. for 1 hour. The reaction mixture is poured into 30 ml of ice-water and extracted with a large amount (poor solubility!) of methylene chloride/methanol/ethanol. The organic phases are washed with water and brine, dried (Na$_2$SO$_4$) and concentrated by evaporation. Stirring in 2 ml of hot ethanol and filtration yield 4-(3-chloro-phenylamino)-3-(fur-2-yl-carbonyl-amino)-1H-pyrazolo[3,4-dipyrimidine; HPLC: $t_{Ret}$ (grad$_{20-100/20}$)=12.7; FARMS: (M+H)$^+$=355.

EXAMPLE 4

Analogously to Example 1, 200 mg (0.767 mmol) of 3-amino-4-(3-chloro-phenylamino)-1H-pyrazolo[3,4-d]pyrimidine (see Step 1.6) in 4 ml of pyridine/methylene chloride 1:1 are reacted at 0° C. with 251 mg (1.05 mmol) of thiophene-2-carboxylic anhydride. Precipitation from a solution in 2 ml of DMSO with 200 ml of citric acid solution (0.5 g/200 ml) yields 4-(3-chloro-phenylamino)-3-(thien-2-yl-carbonylamino)-1H-pyrazolo[3,4-d]pyrimidine; HPLC: $t_{Ret}$(grad$_{20-100/20}$)=14.4; FAB-MS: (M+H)$^+$=371.

EXAMPLE 5

Under a nitrogen atmosphere, 337 µl (3.07 mmol) of NMM and 219 µl (1.68 mmol) of isobutyl chloroformate are added at −20° C. to 189 mg (1.53 mmol) of picolinic acid in 3.2 ml of THF (→white suspension) and then stirred for 30 min. 400 mg (1.53 mmol) of 3-amino-4-(3-chloro-phenylamino)1H-pyrazolo[3,4-d]pyrimidine (see Step 1.6) are then added, and the reaction mixture is allowed to rise to room temperature and is stirred for 1 hour to complete the reaction. The reaction mixture is poured into 100 ml of water, and the crude product is filtered off and washed with water. Stirring at 100° C. in 5 ml of DMSO, the addition of 25 ml of ethanol and filtration result in 4-(3-chlorophenylamino)-3-(pyrid-2-yl-carbonylamino)-1 H-pyrazolo [3,4-d]pyrimidine; m.p. 276–279° C.; HPLC: $t_{Ret}$ $(grad_{20-100/20})=15.2$; FAB-MS: (M+H)$^+$=366.

EXAMPLE 6

Under a nitrogen atmosphere, 320 µl (2.9 mmol) of NMM and 210 1 (1.6 mmol) of isobutyl chloroformate are added at −20° C. to 250 mg (1.5 mmol) of 2,3-methylenedioxybenzoic acid [for preparation see: Chem. Ber. 104 (1971) 2347] in 3.2 ml of THF and then stirred for 45 min. 378 mg (1.45 mmol) of 3-amino-4-(3-chloro-phenylamino)-1H-pyrazolo-[3,4-d]pyrimidine (see Step 1.6) are then added and the reaction mixture is allowed to rise to RT and is stirred for 1 hour to complete the reaction. The reaction mixture is poured into 100 ml of water and stirred for 1 hour, and the crude product is filtered off and washed with water and ethanol. Dissolution in 3 ml of DMSO at =110° C., cooling, filtering and washing with ethanol yield 4-(3chloro-phenylamino)-3-(2,3-methylenedioxy-benzoylamino)-1H-pyrazolo[3,4-d]pyrimidine; HPLC:$t_{Ret}$ $(grad_{20-100/20})=16.5$; FAB-MS: (M+H)$^+$=409.

EXAMPLE 7

Analogously to Example 5, 263 mg (1.53 mmol) of piperonylic acid (Fluka; Buchs/Switzerland) in 3.4 ml of THF and 337 µl (3.07 mmol) of NMM are activated with 219 µl (1.68 mmol) of isobutyl chloroformate and then reacted with 400 mg (1.53 mmol) of 3-amino-4-(3-chloro-phenylamino)-1H-pyrazolo[3,4-d]pyrimidine (see Step 1.6). Crystallization from a hot mixture of 2 ml of DMSO and 16 ml of ethanol yields 4-(3-chlorophenylaminio)- 3-(3,4-methylenedioxy-benzoylamino)-1H-pyrazolo[3,4-d] pyrimidine; m.p. 304–305° C.; HPLC: $t_{Ret}$($grad_{20-100/20}$)=1 4.8; FAB-MS: (M+H)$^+$=409.

EXAMPLE 8

Analogously to Example 5, 386 mg (1.53 mmol) of N-benzyloxycarbonyl-(D,L)valine in 3.2 ml of THF and 337 µl (3.07 mmol) of NMM are activated with 219 µl (1.68 mmol) of isobutyl chloroformate and then reacted with 400 mg (1.53 mmol) of 3-amino-4-(3-chloro-phenylamino)-1H-pyrazolo[3,4-d]pyrimidine (see Step 1.6). The reaction mixture is concentrated by evaporation; ethyl acetate is added to the residue and the ethyl acetate suspension is washed with 2N HCl solution, sat. NaHCO$_3$ solution and brine and finally the insoluble crude product is filtered off. Crystallization from a hot mixture of 1.1 ml of DMSO and 10 ml of ethanol yields rac.-3-([N-benzyloxycarbonyl-valyl]-amino)-4-(3-chlorophenylamino)-1H-pyrazolo[3,4-d]pyrimidine; HPLC:$t_{Ret}$($grad_{20-100/20}$)=1 4.9; FAB-MS: (M+H)$^+$=494.

EXAMPLE 9

Analogously to Example 5, 514 mg (2.3 mmol) of N-benzyloxycarbonyl-(D/L)-alanine in 4.8 ml of THF and 506 µl (4.6 mmol) of NMM are activated with 349 1 (2.6 mmol) of isobutyl chloroformate and then reacted with 600 mg (2.3 mmol) of 3-amino-4-(3-chlorophenylamino)-1H-pyrazolo[3,4-d]pyrimidine (see Step 1.6). Dissolution of the crude product in 2 ml of DMSO at 100° C., addition of 30 ml of ethanol and cooling yield rac.-3-{(N-benzyloxycarbonyl-alanyl)-amino}-4-(3-chloro-phenylamino)-1H-pyrazolo[3,4-d]pyrimidine; mp. 238–240° C.; HPLC: $t_{Ret}$($grad_{20-100/20}$)=13.5; FAB-MS: (M+H)$^+$=466.

EXAMPLE 10

Analogously to Example 5, 436 mg (2.3 mmol) of N-ethoxycarbonyl-(D/L)-valine [prepared from (D/L)-valine as described in J. Org. Chem. 60, 7256 (1995)] in 4.8 ml of THF and 506 µl (4.6 mmol) of NMM are activated with 349 µl (2.6 mmol) of isobutyl chloroformate and then reacted with 600 mg (2.3 mmol) of 3-amino-4-(3-chloro-phenylamino)-1H-pyrazolo[3,4-d]pyrimidine (see Step 1.6). Dissolution in DMSO (2 ml) at 100° C., addition of 25 ml of ethanol and cooling yield rac.-4-(3-chloro-phenylamino)-3{N-ethoxycarbonyl-valyl)-amino}-1H-pyrazolo[3,4-d] pyrimidine; HPLC: $t_{Ret}$($grad_{20-100/20}$)=13.2; FAB-MS: (M+H)$^+$=432.

EXAMPLE 11

Analogously to Example 5, 180 mg (1.03 mmol) of N-methoxycarbonyl-(D/L)-valine [prepared from (D/L)-valine as described in Chem. Lett. 705 (1980)] in 3.2 ml of THF and 260 µl (2.4 mmol) of NMM are activated with 156 µl (1.13 mmol) of isobutyl chloroformate and then reacted with 268.5 mg (1.03 mmol) of 3-amino-4-(3-chloro-phenylamino)-1H-pyrazolo[3,4-d]pyrimidine (see Step 1.6). Stirring in DMSO (1 ml) at 100° C., addition of 7 ml of ethanol and 7 ml of DIPE and cooling yield rac.-4-(3-chloro-phenylamino)-3-{(N-methoxycarbonyl-valyl)-amino}-1H-pyrazolo[3,4d]pyrimidine; HPLC: $t_{Ret}$($grad_{20-100/20}$)=12.4; FAB-MS: (M+H)$^{+=418.}$

EXAMPLE 12

In 4 ml of THF/DMEU 1:3, 40 mg (0.08 mmol) of rac.-3-([N-benzyloxycarbonylvalyl]-amino)-4-(3-chloro-phenylamino)-1H-pyrazolo[3,4-d]pyrimidine (see Example 8) are hydrogenated in the presence of 10 mg of Pd/C (10%) and 10 µl of 1,2-dichlorobenzene. The catalyst is filtered off, and the filtrate is partially concentrated by evaporation in a rotary evaporator, poured into 30 ml of water and again filtered and the filtrate is concentrated by evaporation under a high vacuum first at RT and finally at 50° C. to yield rac.-4-(3-chlorophenylamino)-3-(valyl-amino)-1H-pyrazolo [3,4-d]pyrimidine; HPLC: $t_{Ret}$($grad_{20-100/20}$)=9.2; FAB-MS: (M+H)$^+$=360.

EXAMPLE 13

(S)-3-[3-(Dimethylamino-carbonylamino-methyl)-phenylamino]-4-(1-phenylethylamino)-1H-pyrazolo[3,4-d] pyrimidine is obtained in accordance with the processes described in this text.

EXAMPLE 14

Analogously to Example 5. 502 mg (2.86 mmol) of N-isobutyloxycarbonyl-glycine in 5.9 ml of THF and 580 µl (5.3 mmol) of NMM are activated with 375 µl (2.86 mmol) of isobutyl chloroformate and then reacted with 745 mg (2.86 mmol) of 3-amino-4-(3-chloro-phenylamino)-1H-pyrazolo[3,4-d]pyrimidine (see Step 1.6). Stirring in 7.5 ml of boiling ethanol and filtering while hot yield 4-(3-chloro-phenylamino)-3-([N-iso-butyloxycarbonyl-glycyl]-amino)-1H-pyrazolo[3,4-d]pyrimidine; HPLC: $t_{Ret}$($grad_{20-100/20}$)= 12.8; FAB-MS: (M+H)$^+$=418.

The starting material is prepared as follows:
Step 14.1:
4.3 ml of dioxane and 872 µl (6.66 mmol) of isobutyl chloroformate are added to a solution of 500 mg (6.66 mmol) of glycine in 14 ml of 2N NaOH solution. The mixture is stirred overnight at RT and then extracted with methylene chloride. The aqueous phase is acidified with 4N HCl solution and extracted twice with methylene chloride. Drying (Na$_2$SO$_4$) and concentration of the extracts by evaporation yield N-isobutyloxycarbonyl-glycine; FAB-MS: (M+H)$^+$=176; $^1$H-NMR (CDCl$_3$) 8.0 (sb), 6.93 and 5.21 (2m, 1H), 4.02 and 3.88 (2m, each 2H), 1.93 (m, 1H), 0.94 (d, J=7, 6H).

EXAMPLE 15

Analogously to Example 5, 283 mg (1.49 mmol) of N-methoxycarbonyl-(D/L)-tert-leucine in 3.3 ml of THF and 329 ;d (2.99 mmol) of NMM are activated with 214 μl (1.64 mmol) of isobutyl chloroformate and then reacted with 388 mg (1.49 mmol) of 3-amino-4-(3-chloro-phenylamino)-1H-pyrazolo[3,4-d]pyrimidine (see Step 1.6) for 20 hours. Column chromatography (SiO$_2$; toluene/ethyl acetate=1:1) yields rac.-4-(3-chloro-phenylamino)-3-([2-methoxycarbonylamino-3,3-dimethyl-butyryl]-amino)-1H-pyrazolo[3,4-d]-pyrimidine; HPLC: $t_{Ret}(grad_{20-100/20})$=12.1; FARMS: (M+H)$^+$432.

The starting material is prepared as follows:
Step 15.1:

293 μl (3.81 mmol) of methyl chloroformate are added to a solution of 0.500 g (3.81 mmol) of (D/L)-tert-leucine in a mixture of 8 ml of 2N aqueous sodium hydroxide solution and 2.5 ml of dioxane and the reaction solution is heated at 60° C. for 14 hours. After cooling to RT, the reaction solution is washed with methylene chloride. The aqueous phase is acidified with 4N aqueous hydrochloric acid, saturated with sodium chloride and extracted three times with ethyl acetate. The organic extracts are combined, dried (Na$_2$SO$_4$) and concentrated by evaporation to yield N-(methoxycarbonyl)-(D/L)-tert-leucine; FAB-MS: (M+H)$^+$=190.

EXAMPLE 16

Analogously to Example 5, 365 mg (1.58 mmol) of N-isobutyloxycarbonyl(D/L)-tert-leucine in 3.3 ml of THF and 347 μl (3.15 mmol) of NMM are activated with 226 μl (1.73 mmol) of isobutyl chloroformate and then reacted with 411 mg (1.58 mmol) of 3-amino-4-(3-chloro-phenylamino) 1H-pyrazolo[3,4-d]pyrimidine (see Step 1.6) for 20 hours. Column chromatography (SiO$_2$; toluene/ethyl acetate 1:1) and stirring in ethyl acetate/DIPE yield rac.-4-(3-chloro-phenylamino)-3-([2-isobutyloxycarbonylamino-3,3-dimethylbutyryl)-amino)-1 H-pyrazolo[3,4-d]pyrimidine; HPLC:$t_{Ret}(grad_{20-100/20})$=15.5; FAB-MS: (M+H)$^+$=474.

The starting material is prepared as follows:
Step 16.1:

498 μl (3.81 mmol) of isobutyl chlorotormate are added to a solution of 0.500 g (3.81 mmol) of (D/L)-tert-leucine in a mixture of 8 ml of 2N aqueous sodium hydroxide solution and 2.5 ml of dioxane and the reaction solution is stirred for 14 hours. The reaction solution is then washed with methylene chloride. The aqueous phase is acidified with 4N aqueous hydrochloric acid, saturated with sodium chloride and extracted three times with ethyl acetate. The organic extracts are combined, dried (Na$_2$SO$_4$) and concentrated by evaporation to yield N-isobutyloxycarbonyl-(D/L)-tert-leucine: FAB-MS: (M+H)$^+$=232.

EXAMPLE 17

Analogously to Example 1, 400 mg (1.53 mmol) of 3-amino-4-(3chloro-phenylamino)-1 H-pyrazolo[3,4-d] pyrimidine (see Step 1.6) in 8 ml of pyridine/methylene chloride 1:1 are reacted at 0° C. with 401 μl (1.73 mmol) of caproic anhydride to form 4-(3-chlorophenylamino)-3-hexanoylamino-1 H-pyrazolo[3,4-d]pyrimidine (18 hours RT): HPLC: $t_{Ret}(grad_{20-100})$=12.4; MS: (M)$^+$=358, 259 (M-C$_6$H$_{11}$O).

EXAMPLE 18

Analogously to Example 1, 400 mg (1.53 mmol) of 3-amino-4-(3-chloro-phenylamino)-1H-pyrazolo[3,4-d] pyrimidine (see Step 1.6) in 8 ml of pyridine/methylene chloride 1:1 are reacted at 0° C. with 288 μl (1.68 mmol) of octanoic acid chloride to form 4-(3-chlorophenylamino)-3-octanoylamino-1H-pyrazolo[3,4-d]pyrimidine (18 hours RT): HPLC: $t_{Ret}(grad_{20-100})$=14.5; FAB-MS: (M+H)$^+$=387.

EXAMPLE 19

With the exclusion of moisture, 196 mg (1.12 mmol) of methanesulfonic anhydride are added at 0° C. to 200 mg (0.767 mmol) of 3-amino-4-(3-chloro-phenylamino)-1H-pyrazolo[3,4]pyrimidine (see Step 1.6) in 4 ml of pyridine/methylene chloride 1:1 and the mixture is stirred for 2 hours in an ice bath and overnight at RT. 9 ml of DIPE and 2 ml of hexane are added to the resulting yellow solution, and the product that precipitates is filtered off, dissolved in 2 ml of boiling ethanol and crystallized by the addition of 1 ml of water, yielding 4-(3-chloro-phenylamino)-3-methanesulfonylamino-1H-pyrazolo[3,4-d]-pyrimidine; HPLC: $t_{Ret}(grad_{20-100/20})$=11.3; FABMS: (M+H)$^+$=339.

EXAMPLE 20

With the exclusion of moisture, 275 mg (0.844 mmol) of toluene-4-sulfonic anhydride are added at 0° C. to 200 mg (0.767 mmol) of 3amino-4-(3-chloro-phenylamino)-1 H-pyrazolo[3,4-d]pyrimidine (see Step 1.6) in 4 ml of pyridine/methylene chloride 1:1 and stirred in an ice bath for 7 hours. A further 275 mg of toluene-4-sulfonic anhydride are added and the reaction mixture is stirred overnight at room temperature to complete the reaction. The reaction mixture is poured into water and extracted with 3 portions of methylene chloride. The organic phases are washed with water and brine, dried over Na$_2$SO$_4$ and concentrated by evaporation. Fractional crystallization from hot ethanol and hot DMSO/ethanol (1:10) yields 4-(3-chloro-phenylamino)-3-toluenesulfonylamino-1H-pyrazolo[3,4-d]pyrmidine; HPLC:$t_{Ret}(grad_{20-100/20})$=14.7; FAB-MS: (M+H)$^+$=415.

EXAMPLE 21

With the exclusion of moisture, 200 mg (0.767 mmol) of 3-amino-4-(3-chlorophenylamino)-1 H-pyrazolo[3,4-d] pyrimidine (see Step 1.6) are suspended in 3.2 ml of toluene; 150 μl (0.87 mmol) of N,N-dimethylformamide diethyl acetal in 6 ml of toluene are added and the reaction mixture is heated to boiling. After 5 hours, filtration is carried out, followed by thorough washing with toluene. 4-(3-Chlorophenylamino)-3-(dimethylaminomethyleneamino)-1H-pyrazolo[3,4-d]pyrimidine is obtained; m.p. 243–245° C.; HPLC: $t_{Ret}(grad_{20-100/20})$=9.7; FAB-MS: (M+H)$^+$=316.

EXAMPLE 22

With the exclusion of air, 1.86 g (7.49 mmol) of N'-[3-(morpholin-4-yl)-4-cyano-1 H-pyrazol-5-yl]-N,N-dimethylformamidine in 45 ml of methanol are heated to boiling with 1.84 g (11.2 mmol) of 3-chloro-aniline hydrochloride, during which the solid temporarily dissolves. After about 30 min, a precipitate separates out again. After 8 hours the reaction mixture is cooled, filtered and washed with methanol and DIPE. Stirring the crude product in a boiling mixture of 40 ml of ethanol, 20 ml of chloroform and 20 ml of dioxane yields 4-(3-chloro-phenylamino)-3-(morpholin-4-yl)-1H-pyrazolo[3,4-d]pyrimidine; m.p. 275–276° C.; HPLC:$t_{Ret}(grad_{20-100/20})$=11.6.

The starting material is prepared as follows:
Step 22.1:

A suspension of 8.51 g (50 mmol) of 3,3-bis (methytsulfanyl)-2-cyano-acrylonitrile (Maybridge) and 4.36 ml (50 mmol of morpholine in 100 ml of isopropanol is heated at 80° C. under a nitrogen atmosphere for 3 hours. Cooling, filtering and washing with isopropanol and DIPE yield 3-(morpholin-4-yl)-3-methylsulfanyl-2-cyano-acrylonitrile; m.p . 140–141° C.; TLC: $R_f$=0.39 (ethyl acetate/toluene=1:1).

Step 22.2:

2.78 ml (56 mmol) of hydrazine hydrate are added to a slurry of 9.8 9 (46.8 mmol) of 3-(morpholin-4-yl)-3methylsulfanyl-2-cyanoacrylonitrile in 60 ml of methanol and heated to boiling, with the solid dissolving. After 3.5 hours, the reaction mixture is cooled to RT, concentrated by evaporation and recrystallised from ≈70 ml of boiling ethanol, yielding 5-amino-3-(morpholin-4-yl)-1H-pyrazole-4-carbonitrile: m.p. 199–201° C.; TLC: $R_f$=0.19 (ethyl acetate/toluene=3 3:1).

Step 22.3:

Under a nitrogen atmosphere, a suspension of 4.00 g (20.7 mmol) of 5-amino-3-(morpholin-4-yl)-1H-pyrazole-4-carbonitrile in 85 ml of toluene is boiled under reflux for 5 hours with 4.17 ml (97%; 23.6 mmol) of N,N-dimethylformamide diethyl acetal, during which the solid dissolves. Cooling to RT (→crystallization), filtration with suction an d washing with toluene and hexane yield N'-[3-(morpholin-4-yl)-4-cyano-1H-pyrazol-5-yl]-N,N-dimethyl-formamidine; m.p. 182–183° C.; TLC: $R_f$=0.20 (ethyl acetate).

Step 22.4:

60 g (0.47 mol) of 3-chloro-aniline are dissolved in 255 ml (0.56 mol) of HCl (2.2N in methanol). Concentration and stirring the residue in diethyl ether yield, after filtration and drying (40° C., HV), 3-chloroaniline hydrochloride.

EXAMPLE 23

With the exclusion of air, 496.6 mg (2.00 mmol) of N'-[3-(morpholino-4-yl)-4-cyano-1H-pyrazol-5-yl]-N,N-dimethyl-formamidine in 30 ml of methanol are heated to boiling with 543 mg (3.00 mmol) of 3chloro-4-fluoro-aniline hydrochloride. After 9 hours the reaction mixture is cooled, and 4-(3-chloro-4-fluoro-phenylamino)-3-(morpholin-4-yl)-1H-pyrazolo[3,4-d]pyrimidine is filtered off and washed with methanol and DIPE: m.p. 262–264° C.; HPLC:$t_{Ret}(grad_{20-100/20})$=11.8.

The starting material is prepared as follows:

Step 23.1:

1.75 g (12 mmol) of 3-chloro-4-fluoroaniline are dissolved in 20 ml of methanol, and 3 ml (12 mmol) of HCl (4.0N) are added. Concentration and drying (40° C., HV) yield 3-chloro-4-fluoro-aniline hydrochloride.

EXAMPLE 24

With the exclusion of air, 16.2 9 (46.6 mmol) of N'-[3-(4-tert-butoxycarbonyl-piperazin-1 -yl)-4-cyano-1H-pyrazol-5-yl]-N,N-dimethyl-formamidine in 130 ml methanol are heated to boiling with 11.47 g (70 mmol) of 3-chloro-aniline hydrochloride. After 9 hours the reaction mixture is cooled, filtered and washed with methanol and DIPE. Stirring the crude product in boiling ethanol, cooling and filtration yield 4-(3-chloro-phenylamino)-3-(4-tert-butyloxycarbonyl-piperazin-1-yl)-1H-pyrazolo[3,4-d] pyrimidine; HPLC: $t_{Ret}(grad_{20-100/20})$=15.7; IR (KBr) interalia 1706 s, 1631 s, 1610 s, 1589 s, 1508 m, 1482 s, 1425 m, 1364 m, 1304 m, 1283 m, 1245 m, 1170 m, 1122 m.

The starting material is prepared as follows:

Step 24.1:

With the exclusion of air, 7.22 g (42.4 mmol) of 3,3-bis (methylsulfanyl)-2-cyano-acrylonitrile (Maybridge), 7.90 g (42.4 mmol) of piperazine-N-carboxylic acid tert-butyl ester (Aldrich; Milwaukee/USA) and 0.24 g (3 mmol) of pyridine are heated to boiling in 75 ml of isopropanol for 4 hours. Cooling, concentration by evaporation and drying under a high vacuum yield 3-(4-tert-butoxycarbonyl-piperazin-1-yl)-3-methylsulfanyl-2-cyano-acrylonitrile; $C_{14}H_{20}N_4SO_2$: calc. $C_{54.52}$%, H 6.54%, N 18.17%, S 10.40%; found $C_{54.37}$%, H 6.50%, N 17.85%, S 10.25%.

Step 24.2:

With the exclusion of air, 15.0 g (48.7 mmol) of 3(4-tert-butoxycarbonyl-piperazin-1 -yl)-3-methylsutfanyl-2-cyano-acrylonitrile and 2.93 g (58.4 mmol) of hydrazine hydrate are heated to boiling in 85 ml of methanol. After 5.5 hours the reaction mixture is cooled and concentrated by evaporation to yield 5-amino-3(4-tert-butoxycarbonyl-piperazin-1-yl)-1H-pyrazole-4-carbonitrile; analysis calc. for $C_{13}H_{20}N_6O_2$ (+0.18 $H_2O$): C 52.83%, H 6.94%, N 28.43%, $H_2O$ 1.10%; found C 52.64%, H 6.87%, N 28.35%, $H_2O$ 1.07%.

Step 24.3:

Under a nitrogen atmosphere, a suspension of 12.87 g (44 mmol) of 5-amino-3-(4tert-butoxycarbonyl-piperazin-1-yl)-1H-pyrazole-4-carbonitrile in 150 ml of toluene is boiled under reflux for 6 hours with 18.1 ml (90%; 94 mmol) of N,N-dimethylformamide diethyl acetal. Cooling, concentration by evaporation and stirring in DIPE yield N'-[3-(4-tert-butoxycarbonyl-piperazin-1-yl)-4-cyano-1H-pyrazol-5-yl-]-N,N-dimethyl-tormamidine; analysis calc. for $C_{16}H_{25}N_7O_2$ (+0.07 $H_2O$): $C_{55.12}$%, H 7.27%, N 28.12%, $H_2O$ 0.36%; found $C_{55.14}$%, H 7.24%, N 27.74%, $H_2O$ 0.34%.

EXAMPLE 25

Under a nitrogen atmosphere, 2.0 g (4.65 mmol) of 4-(3-chloro-phenylamino)-3-(4-tert-butyloxycarbonyl-piperazin-1-yl)-1H-pyrazolo[3,4-d]pyrimidine (see Example 24) in 80 ml of dioxane and 80 ml of HCl/dioxane (4N) are stirred at 60° C. for 2 hours. Cooling and filtering yield 4-(3-chloro-phenylamino)-3-(piperazin-1-yl)-1H-pyrazolo[3,4-d]pyrimidine dihydrochloride; analysis calc. for $C_{15}H_{16}N_7Cl.2HCl$ (+0.14 $H_2O$+5% dioxane): $C_{44.93}$%, H 4.78%, N 22.97%, Cl 24.91%, $H_2O$ 0.68%; found $C_{45.12}$%, H 4.73%, N 23.16%, Cl 24.67%, $H_2O$ 0.68%; HPLC: $t_{Ret}(grad_{20-100/20})$=8.0.

EXAMPLE 26

With ice-cooling, a solution of 48.5 mg (0.37 mmol) of propionic anhydride in 10 ml of dioxane is added to 100 mg (0.248 mmol) of 4-(3-chloro-phenylamino)-3-(piperazin-1-yl)-1H-pyrazolo[3,4-d]pyrimidine dihydrochloride (see Example 25) and 103 mg (0.74 mmol) of potassium carbonate in 10 ml of water. The mixture is slowly heated to RT, stirred for 5 hours, then diluted with methylene chloride and washed twice with water and brine. The inorganic phases are extracted twice with methylene chloride; the organic phases are dried ($Na_2SO_4$) and concentrated by evaporation. Stirring in=10 ml of ethanol yields 4-(3-chloro-phenylamino)-3-(4-propionyl-piperazin-1-yl)-1H-pyrazolo[3,4-d] pyrimidine; m.p. 247–250° C.; HPLC: $t_{Ret}(grad_{20-100/20})$= 11.8; FAB-MS: $(M+H)^+$=386.

EXAMPLE 27

Analogously to Example 26, 100 mg (0.248 mmol) of 4-(3-chlorophenylamino)-3-(piperazin-1-yl)-1H-pyrazolo

[3,4-d]pyrimidine dihydrochloride and 103 mg (0.74 mmol) of potassium carbonate in 10 ml of water are reacted with 38 mg (0.37 mmol) of acetic anhydride in 10 ml of dioxane to form 3-(4-acetyl-piperazin-1-yl)-4-(3-chlorophenylamino)-1H-pyrazolo(3,4-d]pyrimidine; HPLC: $t_{Ret}(\text{grad}_{20-100/20})$= 10.8; FAB-MS: $(M+H)^+$=372.

EXAMPLE 28

Under a nitrogen atmosphere, 57.6 mg (0.41 mmol) of benzoyl chloride are added at 0° C. to 150 mg (0.373 mmol) of 4-(3-chloro-phenylamino)-3-(piperazin-1-yl)-1H-pyrazolo[3,4-d]pyrimidine dihydrochloride in 6 ml of methylene chloride/pyridine (1:1). After 17 hours' stirring at 0° C., a further 1 equivalent of benzoyl chloride is added and the reaction mixture is then stirred for a further 6 hours. The mixture is diluted with methylene chloride and washed twice with water and brine. The inorganic phases are extracted twice with methylene chloride; the organic phases are dried $(Na_2SO_4)$ and concentrated by evaporation. Stirring in a small amount of ethyl acetate yields 3-(4-benzoyl-piperazin-1-yl)-4-(3-chloro-phenylamino)-1H-pyrazolo[3,4 d] pyrimidine; m.p. 277–281° C.; HPLC: $t_{Ret}(\text{grad}_{20-100/20})$= 13.5; FABMS: $(M+H)^+$=434.

EXAMPLE 29

In an ampoule, 150 mg (1.25 mmol) of pivalic acid chloride and 10 mg of 4-dimethylaminopyridine are added to 150 mg (0.373 mmol) of 4-(3-chloro-phenylamino)-3-(piperazin-1-yl)-1H-pyrazolo[3,4-d]pyrimidine dihydrochloride in 6 ml of methylene chloride/pyridine (1:1). After 8 days' stirring at 70° C., the reaction mixture is cooled, filtered and washed with methylene chloride. The filtrate is concentrated by evaporation, and the residue is dissolved in DMSO and poured into water. Filtration and washing with water yield 4-(achloro-phenylamino)-3-(4-pivaloyl-piperazin-1-yl)-1H-pyrazolo[3,4-d]pyrimidine; HPLC: $t_{Ret}$ $(\text{grad}_{20-100/20})$=13.8; FAB-MS: $(M+H)^+$=414.

EXAMPLE 30

Analogously to Example 26, 100 mg (0.248 mmol) of 4-(3-chloro-phenylamino)-3-(piperazin-1-yl)-1H-pyrazolo[3,4-d]pyrimidine dihydrochloride and 103 mg (0.74 mmol) of potassium carbonate in 10 ml of water are reacted with 81.5 mg (0.37 mmol) of lauric acid chloride in 10 ml of dioxane and extracted. Column chromatography $(SiO_2;$ methylene chloride/ethyl acetate/acetic acid=50:50:1) yields 4-(3-chloro-phenylamino)-3-(4-[n-dodecanoyl]-piperazin-1-yl)-1H-pyrazolo[3,4-d]pyrimidine; HPLC: $t_{Ret}(\text{grad}_{20-100/20})$=22.6; FAB-MS: $(M+H)^+$=512.

EXAMPLE 31

Under a nitrogen atmosphere, 75 mg (0.74 mmol) of NMM and 110 µl (0.84 mmol) of isobutyl chloroformate are added at 0° C. to 92 mg (0.74 mmol) of picolinic acid in 4 ml of THF and the mixture is heated to RT and then stirred for 35 min. Then 100 mg (0.248 mmol) of 4-(3-chloro-phenylamino)-3-(piperazin-1-yl)-1H-pyrazolo[3,4d] pyrimidine dihydrochloride and 103 mg (0.74 mmol) of potassium carbonate in 20 ml of water/dioxane (1:1) are added and the mixture is stirred for 1 hour to complete the reaction. The reaction mixture is poured into 200 ml of water, and the desired compound is filtered off and washed with water. 4-(3-Chloro-phenylamino)-(4-[pyridyl-2-carbonyl]-piperazin-1-yl)-1H-pyrazolo[3,4-d)pyrimidine is obtained; m.p. 233–235° C.; HPLC: $t_{Ret}(\text{grad}_{20-100/20})$= 11.6; FAB-MS: $(M+H)^+$=435.

EXAMPLE 32

Under a nitrogen atmosphere and with ice-cooling, 8 ml (8 mmol) of DIBAL-H are added to 345 mg of 4-(3-chloro-phenylamino)-3-1(pyrid-2-yl)-methyleneamino]-1H-pyrazolo[3,4-d]pyrimidine in 30 ml of DMEU and the mixture is stirred for 2 hours, during which the suspension dissolves. 15 ml of ethyl acetate are added and the mixture is stirred for 30 min and diluted with 150 ml of methanol. 1 ml of water and 10 g of $Na_2SO_4$ are added to the precipitate, followed by stirring for 15 min and then filtration. The methyl alcohol is evaporated off from the filtrate in a rotary evaporator. The resulting DMEU solution is poured into 400 ml of water, stirred to complete the reaction and filtered. The filter residue is taken up in DMSO, filtered again and the filtrate is poured into 200 ml of water. Filtration and washing with water yield 4-(3-chloro-phenylamino)-3-1(pyrid-2-yl)-methylamino]-1H-pyrazolo[3,4-d]pyrimidine; m.p. 235–239° C.; HPLC: $t_{Ret}(\text{grad}_{20-100/20})$=7.9; FAB-MS: $(M+H)^+$=352.

The starting material is obtained as follows:

Step 32.1:

With gentle heating, 522 mg (2.00 mmol) of 3-amino-4-(3-chloro-phenylamino)-1H-pyrazolo[3,4-d]pyrimidine (see Step 1.6) and 360 mg of acetic acid are dissolved in 52 ml of methanol. Then, at RT, 321 mg (3.0 mmol) of pyridine-2-carbaldehyde are added and the reaction mixture is stirred overnight to complete the reaction, during which time 4-(3-chloro-phenylamino)-3-[(pyrid-2-yl)-methyleneamino]-1H-pyrazolo[3,4-d]pyrimidine separates out. The latter is filtered off, washed with methanol and dried under a high vacuum; $^1$H-NMR (DMSO-$d_6$; 100° C.) 9.22 (s, 1H), 8.79 (m, 2H), 8.51 (s, 1H), 8.45 (d, J=8, 1H), 8.16 (m, 1H), 8.05 (t, J=8, 1H), 7.70 (d, J=8, 1H), 7.59 (m, 1H), 7.42 (t, J=8, 1H), 7.17 (d, J-8, 1H).

EXAMPLE 33

Analogously to Step 32.1, 261 mg (1.00 mmol) of 3-amino-4-(3-chloro-phenyl-amino)-1 H-pyrazolo[3,4-d] pyrimidine (see Step 1.6) and 180 mg of acetic acid are dissolved in 26 ml of methanol and reacted with 161 mg (1.5 mmol) of pyridine-4-carbaldehyde to form 4-(3-chloro-phenylamino)-3-[(pyrid-4-yl)-methyleneamino]-1H-pyrazolo[3,4-d]pyrimidine. Reduction of the above intermediate in 25 ml of DMEU with 8 ml (8 mmol) of DIBAL-H analogously to Example 32 and analogous working-up yield 4-(3-chlorophenylamino)-3-[(pyrid-4-yl)-methylamino]-1H-pyrazolo[3,4-d]pyrimidine; HPLC: $t_{Ret}(\text{grad}_{20-100/20})$ 7.7; FAB-MS: $(M+H)^+$=352.

EXAMPLE 34

Under a nitrogen atmosphere, 261 mg (1.00 mmol) of 3amino-4-(3-chlorophenylamino)-1 H-pyrazolol-[3,4-d] pyrimidine (see Step 1.6), 161 mg (1.5 mmol) of pyridine-3carbaldehyde and 180 mg of acetic acid are stirred in 39 ml of DMEU/methanol (1:2) at RT for 1 hour. 440 mg (7 mmol) of $NaCNBH_3$ are then added and the reaction mixture is heated to boiling. After 20 hours a further 440 mg of $NaCNBH_3$ are added and the reaction mixture is stirred at boiling temperature for 15 hours, then poured into 0.6 liter of a 1% aqueous $K_2B_4O_7.4H_2O$ solution and stirred overnight to complete the reaction. The precipitated product is filtered off and washed with water. Recrystallization from boiling ethyl acetate yields 4-(3-chlorophenylamino)-3-[(pyrid-3-yl)methylamino]-1H-pyrazolo[3,4-d]pyrimidine; m.p. 204–206° C.; MS $(M)^+$=351; HPLC:$t_{Ret}(\text{grad}_{20-100/20})$=7.6.

EXAMPLE 35

Under a nitrogen atmosphere, 261 mg (1.00 mmol) of 3-amino-4-(3-chlorophenylamino)-1 H-pyrazolo[3,4-d]pyrimidine (see Step 1.6), 261 mg (1.5 mmol) of 4-(tetrazol-5-yl)-benzaldehyde and 180 mg of acetic acid are stirred in 39 ml of DMEU/methanol (1:2) at RT for 1 hour. Then 440 mg (7 mmol) of NaCNBH$_3$ are added and the reaction mixture is heated to boiling. After 15 hours a further 440 mg of NaCNBH$_3$ are added and the reaction mixture is again stirred at boiling temperature for 15 hours, then poured into 0.6 liter of a 1 aqueous K$_2$B$_4$O$_7$.4H$_2$O solution and stirred overnight to complete the reaction. The mixture is acidified to pH 3.9 with 2N HCl and the product that precipitates is filtered off and washed with water. Heating in 20 ml of ethanol and filtration yield 4-(3chloro-phenylamino)-3-[4-(tetrazol-5-yl)-benzylamino]-1H-pyrazolo-[3,4-d]pyrimidine; HPLC:t$_{Ret}$(grad$_{20-100/20}$)=9.8; MS: (M)$^{+-}$418.

The starting material is prepared as follows:
Step 35.1:
20.0 g (0.47 mol) of lithium chloride and 20.5 g (0.315 mol) of sodium azide are added to 41.2 9 (0.315 mol) of 4-cyano-benzaldehyde in 310 ml of methoxy-ethanol and the mixture is heated at boiling for 6 hours (argon atmosphere). When cool the reaction mixture is poured into 1 liter of ice/HCl 37% (10:1) and stirred thoroughly to complete the reaction. Filtration and washing with water yield 4-(tetrazol-5-yl)-benzaldehyde; m.p. 180–182° C.

EXAMPLE 36

Under a nitrogen atmosphere, 261 mg (1.00 mmol) of 3-amino-4-(3-chlorophenylamino)-1 H-pyrazolo[3,4-d]pyrimidine (see Step 1.6), 273 mg (1.5 mmol) of biphenyl-4-carbaldehyde and 180 mg of acetic acid are stirred in 39 ml of DMEU/methanol (1:2) at RT for 1 hour. 440 mg (7 mmol) of NaCNBH$_3$ are then added and the reaction mixture is heated to 50° C. After 15 hours a further 440 mg of NaCNBH$_3$ are added and the reaction mixture is stirred at boiling temperature for 15 hours, then poured into 0.6 liter of a 1% aqueous K$_2$B$_4$O$_7$.4H$_2$O solution and stirred overnight to complete the reaction. The precipitated product is filtered off and washed with water. Heating in 20 ml of ethanol and filtration yield 4-(3-chloro-phenylamino)-3-(4-phenyl-benzylamino)-1H-pyrazolo[3,4-d]pyrimidine; m.p. 250–252° C.; HPLC: t$_{Ret}$(grad$_{20-100/20}$=14.1; FAB-MS: (M+H)$^+$=427.

EXAMPLE 37

Analogously to Example 34, 261 mg (1.00 mmol) of 3amino-4-(3-chlorophenylamino)-1H-pyrazolo[3,4-d]pyrimidine (see Step 1.6), 282 mg (1.5 mmol) of 4-(2-methyl-2H-tetrazol-5-yl)-benzaldehyde and 180 mg of acetic acid are stirred in 39 ml of DMEU/methanol (1:2) at RT for 1 hour and then reacted with two 440 mg (7 mmol) portions of NaCNBH$_3$. 4-(3-Chloro-phenylamino)-3-[4-(2-methyl-tetrazol-5-yl)-benzylamino]-1H-pyrazolo[3,4-d]pyrimidine is obtained; m.p. 232–235° C.; HPLC: t$_{Ret}$(grad$_{20-100/20}$)=11.4; FAB-MS: (M+H)$^+$=433.

The starting material is prepared as follows:
Step 37.1:
With ice-cooling, a solution of 75.5 g (0.434 mol) of 4-(tetrazol-5-yl)-benzaldehyde (Step 35.1) in 550 ml of DMF/dioxane (1:1) is added dropwise to 179.7 g (1.30 mol) of K$_2$CO$_3$ in 200 ml of DMF/dioxane (1:1); stirring is carried out for 30 min and then 40 ml (0.64 mol) of methyl iodide are added dropwise. The reaction mixture is stirred for 3 hours in an ice bath and finally for 15 hours at RT, poured into 2.8 liters of ice-water and stirred for 10 min, and the compound is filtered off and washed with water, yielding 4-(2-methyl-2H-tetrazol-5-yl)-benzaldehyde; m.p. 137–139° C.

EXAMPLE 38

Analogously to Example 32, 261 mg (1.00 mmol) of 3-amino-4-(3-chlorophenylamino)-1H-pyrazolo[3,4-d]pyrimidine (see Step 1.6) and 180 mg of acetic acid are dissolved in 26 ml of methanol and reacted with 168 mg (1.5 mmol) of thiophene-3-carbaldehyde to form 4-(3-chlorophenylamino)-3-[(thien-3-yl)-methyleneamino]-1H-pyrazolo[3,4-d]pyrimidine. Reduction of that intermediate in 15 ml of DMEU with 8 ml (8 mmol) of DIBAL-H, analogous working-up and digestion in DIPE yield 4-(3-chlorophenylamino)-3-[(thien-3-yl)-methylamino]-1H-pyrazolo[3,4-d]pyrimidine; HPLC: t$_{Ret}$(grad$_{20-100/20}$)=11.4; FAB-MS: (M+H)$^+$=357.

EXAMPLE 39

Analogously to Example 32, 261 mg (1.00 mmol) of 3-amino-4-(3-chlorophenylamino)-1H-pyrazolo[3,4-d]pyrimidine (see Step 1.6) and 180 mg of acetic acid are dissolved in 26 ml of methanol and reacted with 170 mg (1.5 mmol) of thiazole-2-carbaldehyde to form 4-(3-chlorophenylamino)-3-[(thiazol-2-yl)-methyleneamino]-1H-pyrazolo[3,4-d)pyrimidine. Reduction of the above intermediate in 15 ml of DMEU with 8 ml (8 mmol) of DIBAL-H, analogous working-up and digestion in DIPE yield 4-(3-chloro-phenylamino)3[(thiazol-2-yl)-methylamino]-1H-pyrazolo[3,4-d]pyrimidine; HPLC:t$_{Ret}$(grad$_{20-100/20}$)=9.8; FAB-MS: (M+H)$^+$=358.

EXAMPLE 40

Analogously to Example 32, 261 mg (1.00 mmol) of 3-amino-4-(3-chlorophenylamino)-1H-pyrazolo[3,4-d]pyrimidine (see Step 1.6) and 180 mg of acetic acid are dissolved in 26 ml of methanol and reacted with 143 mg (1.5 mmol) of pyrrole-2-carbaldehyde to form 4-(3-chlorophenylamino)-3-[(1H-pyrrol-2-yl)-methyleneamino]-1H-pyrazolo[3,4-d]pyrimidine. Reduction of the above intermediate in 15 ml of DMEU with 8 ml (8 mmol) of DIBAL-H, analogous working-up and digestion in DIPE yield 4-(3-chloro-phenylamino)-3-[(1H-pyrrol-2-yl)-methylamino]-1H-pyrazolo[3,4-d]pyrimidine; HPLC: t$_{Ret}$(grad$_{20-100/20}$)= 8.2; FAB-MS: (M+H)$^+$=340.

EXAMPLE 41

Analogously to Example 32, 261 mg (1.00 mmol) of 3-amino-4-(3-chlorophenylamino)-1H-pyrazolo[3,4-d]pyrimidine (see Step 1.6) and 180 mg of acetic acid are dissolved in 26 ml of methanol and reacted with 144 mg (1.5 mmol) of imidazole-2-carbaldehyde to form 4-(3-chlorophenylamino)-3-[(1H-imidazol-2-yl)-methyleneamino]-1H-pyrazolo[3,4-d]pyrimidine. Reduction of the above intermediate in 15 ml of DMEU with 8 ml (8 mmol) of DIBAL-H, analogous working-up and digestion in ethanol yield 4-(3-chlorophenylamino)-3-(1H-imidazol-2-yl)-methylamino]-1H-pyrazolo[3,4-d]pyrimidine; HPLC: t$_{Ret}$(grad$_{20-100/20}$) 5.8; FABMS: (M+H)$^+$=341.

EXAMPLE 42

Analogously to Example 32, 261 mg (1.00 mmol) of 3-amino-4-(3-chlorophenylamino)-1H-pyrazolo[3,4-d]

pyrimidine (see Step 1.6) and 180 mg of acetic acid are dissolved in 26 ml of methanol and reacted with 144 mg (1.5 mmol) of 3-furaldehyde to form 4-(3-chloro-phenylamino)-3-[(fur-3-yl)-methyleneamino]-1H-pyrazolo[3,4-d] pyrimidine. Reduction of the above intermediate in 15 ml of DMEU with 8 ml (8 mmol) of DIBAL-H, analogous working-up and digestion in DIPE yield 4-(3-chloro-phenylamino)-3-[(fur-3-yl)-methylamino]-1H-pyrazolo[3,4-d]pyrimidine; m.p. 207–209° C.; HPLC: $t_{Ret}(\text{grad}_{20-100/20})$=8.4; MS: (M)+=340, (M−H)$^+$=339.

EXAMPLE 43

Analogously to Example 32, 261 mg (1.00 mmol) of 3-amino-4-(3-chlorophenylamino)-1H-pyrazolo[3,4-d] pyrimidine (see Step 1.6) and 180 mg of acetic acid are dissolved in 26 ml of methanol and reacted with 144 mg (1.5 mmol) of imidazole-4-carbaldehyde (for preparation see: Ph. D. Stein and St. E Hall, U.S. Pat. No. 4,977,174, 11th Dec. 1990) to form 4-(3-chloro-phenylamino)-3-[1H-(imidazol-4-yl)-methyleneamino]-1H-pyrazolo[3,4-d] pyrimidine. Reduction of the above intermediate in 15 ml of DMEU with 8 ml (8 mmol) of DIBAL-H, analogous working-up and digestion in ethyl acetate yield 4-(3-chlorophenylamino)-3-[1H-(imidazolyl-4-yl)-methylamino]-1H-pyrazolo[3,4-d]pyrimidine; HPLC: $t_{Ret}$ (grad$_{20-100}$)=5.9; FAB-MS: (M+H)$^+$=341.

Example 44

Analogously to Example 32, 261 mg (1.00 mmol) of 3-amino-4-(3-chlorophenylamino)-1H-pyrazolo[3,4-d] pyrimidine (see Step 1.6) and 180 mg of acetic acid are dissolved in 26 ml of methanol and reacted with 144 mg (1.5 mmol) of furfural to form 4-(3-chloro-phenylamino)-3-[(fur-2-yl)-methyleneamino]-1H-pyrazolo[3,4-d]-pyrimidine. Reduction of the above intermediate in 15 ml of DMEU with 8 ml (8 mmol) of DIBAL-H and analogous working-up yield 4-(3-chloro-phenylamino-3-[(fur-2-yl)-methylamino]-1H-pyrazolo[3,4-d]pyrimidine; HPLC: $t_{Ret}$ (grad$_{20-100}$) 8.4; MS (M)$^+$=340.

EXAMPLE 45

Analogously to Example 32, 261 mg (1.00 mmol) of 3-amino-4-(3-chlorophenylamino)-1H-pyrazolo[3,4-d] pyrimidine (see Step 1.6) and 180 mg of acetic acid are dissolved in 26 ml of methanol and reacted with 164 mg (1.5 mmol) of 1-methyl-pyrrole-2-carbaldehyde to form 4,(3-chloro-phenylamino)-3-[(1-methyl-pyrrol-2-yl)-methyleneamino]-1H-pyrazolo[3,4-d]pyrimidine. Reduction of the above intermediate in 15 ml of DMEU with 8 ml (8 mmol) of DIBAL-H and analogous working-up yield 4-(3-chloro-phenylamino)-3-[(1-methyl-pyrrol-2-yl)-methylamino]-1H-pyrazolo[3,4-d]pyrimidine; HPLC: $t_{Ret}$ (grad$_{20-100}$)=6.7; FAB-MS: (M+H)$^+$=354.

EXAMPLE 46

Analogously to Example 32, 4-(3-chloro-phenylamino)-3-(3-phenoxy-benzylamino)-1H-pyrazolo[3,4-d]pyrimidine is obtained.

EXAMPLE 47

Analogously to Example 32, 4-(3-chloro-phenylamino)-3-[(3-(4-chlorophenoxy)-benzylamino]-1H-pyrazolo[3,4-d]pyrimidine is obtained.

EXAMPLE 48

Analogously to Example 32, 4-(3-chloro-phenylamino)-3-(naphth-2-yl-methylamino)-1H-pyrazolo[3,4-d]pyrimidine is obtained.

EXAMPLE 49

Analogously to Example 32, 261 mg (1.00 mmol) of 3-amino-4-(3-chlorophenylamino)-1 H-pyrazolo[3,4-d] pyrimidine and 180 mg of acetic acid are dissolved in 26 ml of methanol and reacted with 182 mg (1.5 mmol) of 6-methyl-pyridine-2-carbaldehyde to form 4-(3-chloro-phenylamino)-3-[(6-methyl-pyrid-2-yl)-methyleneamino)-1H-pyrazolo-[3,4-d]pyrimidine. Reduction of the above intermediate in 15 ml of DMEU with 8 ml (8 mmol) of DIBAL-H, analogous working-up and digestion in ethyl acetate yield 4-(3-chloro-phenylamino)-3-[(6-methyl-pyrid-2-yl)-methylamino]-1H-pyrazolo[3,4-d]pyrimidine; m.p: 231–233° C.; HPLC: $t_{Ret}(\text{grad}_{20-100})$=6.6; MS: (M)$^+$=365.

EXAMPLE 50

Analogously to Example 34, 4-(3-chloro-phenylamino)-3-[(2-ethoxycarbonylcycloprop-1-yl)-methylamino]-1H-pyrazolo[3,4-d]pyrimidine is obtained.

EXAMPLE 51

Analogously to Example 32, 261 mg (1.00 mmol) of 3-amino-4-(3-chlorophenylamino)-1H-pyrazolo[3,4d] pyrimidine (see Step 1.6) and 180 mg of acetic acid are dissolved in 26 ml of methanol and reacted with 345 mg (1.5 mmol) of 4-(2-tert-butyl-tetrazol-5-yl)-benzaldehyde to form 4-(3-chloro-phenylamino)-3-[{4-(2-tert-butyl-tetrazol-5-yl}-phen-1-yl)-methyleneamino]-1H-pyrazolol[3,4-d] pyrimidine. Reduction of the above intermediate in 15 ml of DMEU with 8 ml (8 mmol) of DIBAL-H and analogous working-up and stirring in DIPE yield 4-(3-chloro-phenylamino)-3-[4-(2-tert-butyl-tetrazol-5-yl)-benzylamino]-1H-pyrazolo[3,4-d]pyrimidine; m.p. 168–170° C., HPLC: $t_{Ret}(\text{grad}_{20-100})$=10.4; MS: (M)$^{+=474}$.

The starting material is prepared as follows:
Step 51.1:

In an autoclave, 5.0 9 (28.7 mmol) of 4-(tetrazol-5-yl)-benzaldehyde (Step 35.1) in 33 ml of toluene are heated at 110° C. for 2 hours with -2.4 g of isobutene and 377 μl of methanesulfonic acid. When cold the reaction mixture is diluted with 50 ml of ethyl acetate, washed twice with sat. NaHCO$_3$ solution, once with water and brine, dried (Na$_2$SO$_4$) and concentrated by evaporation. Crystallization from ethanol yields 4-(2-tert-butyl-tetrazol-5-yl)-benzaldehyde; $^1$H-NMR (DMSO-d$_6$) 10.11 (s, HCO), 8.31 (d, J=8, 2H), 8.11 (d, J=8, 2H), 1.78 (s, 9H).

EXAMPLE 52

With the exclusion of air, 261 mg (1.00 mmol) of 3-amino-4-(3-chloro-phenylamino)-1H-pyrazolo[3,4-d] pyrimidine and 180 mg of acetic acid are dissolved, with gentle heating, in 26 ml of methanol and reacted with 419 mg (1.5 mmol) of 4-formyl-1-methyl-pyridinium benzene-suftonate. After 20 hours' stirring at RT, the reaction mixture is concentrated by evaporation. The residue is taken up in 15 ml of DMEU, cooled to 0° C. and 8 ml (8 mmol) of DIBAL-H are added. After 2 hours 15 ml of ethyl acetate are added and the reaction mixture is stirred for 1 hour and diluted with 150 ml of methanol. 1 ml of water and 10 g of Na$_2$SO$_4$ are added, followed by stirring for 1 hour and then filtration. The filtrate is concentrated by evaporation (RV, HV); the residue is taken up in 12 ml of methanol/HCl 1 N (1:1) and filtered. Concentration of the filtrate by evaporation and separation by means of preparative high pressure chromatography (C18-Nucleosil, water/acetonitrile+0.05% TFA) yield 4-{[4-(3-chloro-phenylamino)-1H-pyrazolo[3,4- d]pyrimidin-3-ylamino]-methyl}-1-methyl-pyridinium trifluoroacetate; HPLC: $t_{Ret}(grad_{5-40})$=11.6; $^1$H-NMR (CD$_3$OD) 9.17 (d, J=6, 2H), 8.64 (d, J=6, 2H), 8.41 (s, 1H), 7.85 (sb, 1H), 7.55 (d, J=8, 1H), 7.35 (t, J=8, 1H), 7.17 (d, J=8, 1H), 4.53 (s, 3H).

EXAMPLE 53

Analogously to Example 32,261 mg (1.00 mmol) of 3-amino-4-(3-chlorophenylamino)-1H-pyrazolo[3,4-d]pyrimidine (see Step 1.6) and 180 mg of acetic acid are dissolved in 26 ml of methanol and reacted with 168 mg (1.5 mmol) of thiophene-2-carbaldehyde to form 4-(3-chlorophenylamino)-3-[(thien-2-yl)-methyleneamino]-1H-pyrazolo[3,4-d]pyrimidine. Reduction of the above intermediate in 0.15 ml of DMEU with 8 ml (8 mmol) of DIBAL-H, analogous working-up and crystallization from ethyl acetate yield 4-(3-chloro-phenylamino)-3-[(thien-2-yl)-methylamino]-1H-pyrazolo[3,4-d]pyrimidine; m.p. 228–229° C., HPLC: $t_{Ret}(grad_{20-100})$=8–9; MS: (M)$^+$=356.

EXAMPLE 54

Analogously to Example 32, 261 mg (1.00 mmol) of 3-amino-4-(3-chloro-phenylamino)-1H-pyrazolo[3,4-d]pyrimidine (see Step 1.6) and 180 mg of acetic acid are dissolved in 26 ml of methanol and reacted with 293 mg (1.5 mmol) of 4-(pyrid-2-yl)-benzaldehyde to form 4-(3-chloro-phenylamino)-3-[{4-(pyrid-2-yl)-phen-1-yl}-methyleneamino]-1H-pyrazolo[3,4-d]pyrimidine. Reduction of the above intermediate in 36 ml of DMEU with 9.6 ml (9.6 mmol) of DIBAL-H and analogous working-up yield 4-(3-chloro-phenylamino)-3 -[4-(pyrid-2-yl)-benzylamino[-1H-pyrazolo[3,4-d]pyrimidine; HPLC:$t_{Ret}$ (grad$_{20-100/20}$)=9.0; FAB-MS: (M+H)$^+$=428.

The starting material is obtained as follows:
Step 54.1:

6.93 g (29.9 mmol) of 4-bromo-benzaldehyde dimethyl acetal in 40 ml of THF are added dropwise to a suspension at 40–50° C. of 0.8 g (31.6 mmol) of magnesium turnings and a small amount of iodine in 10 ml of THF. The reaction mixture is heated to 65° C. and stirred at that temperature for about 30 min. The reaction mixture is cooled to RT and the Grignard reagent is added dropwise to a solution of 4.46 g (28.2 mmol) of 2-bromo-pyridine (Fluka, Buchs, Switzerland) and 0.4 g (0.74 mmol) of [1,3-bis (diphenylphosphino)propane]nickel(II) chloride (DPPP, Fluka, Buchs, Switzerland) in 100 ml of THF (slightly exothermic). When the dropwise addition is complete, the reaction mixture is boiled at reflux for 4 hours, then allowed to cool, and 100 ml of water are added. The mixture is concentrated to about 50 ml in a rotary evaporator, diluted with ethyl acetate and extracted with 0.1N hydrochloric acid (3 times). The combined HCl extracts are stirred at RT for 20 min, rendered basic with conc. ammonia solution and extracted with methylene chloride. After removal of the solvent, the residue is chromatographed on silica gel (hexane:ethyl acetate=2:1). The fractions containing the product are concentrated, and 4-(pyrid-2-yl)-benzaldehyde crystallizes out spontaneously; TLC: R$_f$=0.22 (hexane/ethyl acetate=2:1).

EXAMPLE 55

With ice-cooling, 10.3 ml (10.3 mmol) of DISAL-H are added to 550 mg (1.29 mmol) of 4-(3-chloro-phenylamino)-3-{[4-(pyrid-3-yl)-phenyl]-methyleneamino}-1H-pyrazolo [3,4-d]pyrimidine that have been dissolved in 25 ml of DMEU and the reaction mixture is stirred for 60 min. 15 ml of ethyl acetate are added and the mixture is stirred for 5 min and diluted with 300 ml of methanol and 1 ml of water; 20 g of Na$_2$SO$_4$ are added and after 15 min the mixture is filtered and the filtrate is concentrated by evaporation in a rotary evaporator. The residue is poured into 0.5 liter of water and 0.7 liter of ethyl acetate, and the aqueous phase is separated off and extracted twice more with ethyl acetate. The organic phases are washed 20 times with water (until DMEU-free) and finally with brine, dried (Na$_2$SO$_4$) and concentrated by evaporation. Stirring in methanol and filtration until clear and stirring in ethyl acetate and diethyl ether yield 4-(3-chloro-phenylamino)-3-[4-(pyrid-3-yl)-benzylamino]-1H-pyrazolo[3,4-d]pyrimidine; TLC: R$_f$=0.47 (CHCl$_3$/methano/H$_2$O/acetic acid=85:13:1.5:0.5); HPLC: $t_{Ret}(grad_{20-100})$=6.4; FAB-MS: (M+H)$^+$=428.

The starting material is prepared as follows:
Step 55.1:

A solution of 7.05 g (102 mmol) of sodium nitrite in 16 ml of water is added dropwise at 5° C. in the course of 30 min to a suspension of 11.8 g (0.10 mol) of 4-aminobenzonitrile in 40 ml of water and 36.2 ml of conc. HCl. The turbid yellow reaction solution is then added dropwise at 35–40° C. over a period of 100 min to 121 ml of pyridine. After 45 minutes' stirring at 90° C. the excess pyridine is evaporated off (RV; 60° C.), and the residue is taken up in ethyl acetate and washed with water and brine, dried (Na$_2$SO$_4$) and concentrated by evaporation. Column chromatography (SiO$_2$; hexane/ethyl acetate 4:1→3:2→1:1→ethyl acetate) yields 4-(pyridin-2-yl)-benzonitrile, followed by 4-(pyrid-3-yl)-benzonitrile [$^1$H-NMR (CDCl$_3$) 8.86 (dd, J=2, 1, 1H), 8.68 (dd, J=5, 2, 1H), 7.89 (m, 1H), 7.79 (d, J=9, 2H), 7.69 (d, J=9, 2H), 7.43 (dd, J=8, 5, 1H)] and finally 4-(pyridin-4-yl)-benzonitrile.
Step 55.2:

In the presence of 1 g of Raney nickel, 783 mg (4.34 mmol) of 4-(pyrid-3-yl)-benzonitrile and 2.71 g (10.4 mmol) of 3-amino-4-(3-chloro-phenylamino)-1H-pyrazolo-[3,4-d] pyrimidine are hydrogenated in 200 ml of methanol and 1.87 g of acetic acid (normal pressure; RT). The resulting gray suspension is diluted with 0.3 liter of THF, heated to 50° C. and filtered. From the filtrate there is obtained, after concentration by evaporation and stirring in ethyl acetate and then in methanol, 4-(3-chloro-phenylamino)-3-{14-(pyrid-3-yl)-phenyl]-methyleneamino}-1H-pyrazolo[3,4-d] pyrimidine; TLC: R$_f$=0.57 (CHCl$_3$/methanol/H$_2$O/acetic acid=85:13:1.5:0.5); FAB-MS: (M+H)$^+$=426.

EXAMPLE 56

Analogously to Example 55, 4-(3-chloro-phenylamino)-3-[4-(pyrid-4-yl)-benzylamino]-1H-pyrazolo[3,4-d] pyrimidine is obtained from 3-amino-4-(3-chloro-phenylamino)-1H-pyrazolo[3,4-d9 pyrimidine and 4-(pyrid-4-yl)-benzonitrile (Step 55.2).

EXAMPLE 57

Analogously to Example 32, 521 mg (2.00 mmol) of 3-amino-4-(3-chlorophenylamino)-1H-pyrazolo[3,4-d] pyrimidine (see Step 1.6) and 343 µl of acetic acid are dissolved in 50 ml of methanol and reacted with 567 mg (3.0 mmol) of 4-(thiazol-2-yl)-benzaldehyde to form 4-(3chloro-phenylamino)-3t{4-(thiazol-2-yl)-phen-1-yl) methyleneamino]-1H-pyrazolo[3,4-d]pyrimidine. The above intermediate is reduced in 30 ml of DMEU with 16 ml (16 mmol) of DIBAL-H and worked up analogously. The crude product is dissolved in THF/methanol; 20 g of silica gel are added and the mixture is dried to a powder. Application to a silica gel column and elution with $CH_2Cl_2$/methanol/$H_2O$/acetic acid (85:13:1.5:0.5) yield 4-(3-chloro-phenylamino)-3-[4-(thiazol-2-yl)-benzylamino]-1H-pyrazolo[3,4-d]pyrimidine; m.p. 241–243° C.; TLC: $R_f$=0.44 ($CHCl_3$/methanol/$H_2O$/acetic acid=85:13:1.5:0.5); HPLC: $t_{Ret}$(grad20–100)=9.0; FAB-MS: $(M+H)^+$=434.

The starting material is prepared as follows:
Step 57.1:

Under argon, 9.2 g (379 mmol) of magnesium are placed in 84 ml of THF and heated to 60° C. A solution of 82.6 g (357 mmol) of 4-bromo-benzaldehyde dimethyl acetal (for preparation see *J. Org. Chem.* 56, 4280 (1991)) in 677 ml of THF is then added dropwise thereto in the course of 30 min and the mixture is stirred at boiling temperature for a further 40 min. The Grignard solution is cooled, decanted into a dropping funnel and added dropwise in the course of 30 min to a reddish suspension of 31.7 ml (338 mmol) of 2-bromo-thiazole and 5.39 g (9.95 mmol) of 1,3-bis(diphenylphosphino)propane-nickel(II) chloride (Aldrich; Milwaukee/USA) in 1.68 liters of THF. The reaction mixture is stirred at RT for 12 hours; a further 5.39 g of 1,3bis(diphenylphosphino)-propane-nickel(II) chloride are added and stirring is continued for a further 7 hours. 840 ml of water are added, stirring is carried out for 10 min, the THF is evaporated off in a rotary evaporator and the residue is stirred in 1.0 liter of diethyl ether and 340 ml of 2N HCl for 1.5 hours. The aqueous phase is separated off and extracted twice with ethyl acetate. The organic phases are washed twice with 0.5N HCl, water, sat. $NaHCO_3$ solution, water and brine, dried ($Na_2SO_4$) and concentrated by evaporation. Chromatography ($SiO_2$; hexane/ethyl acetate=4:1) and digestion in hexane yield 4-(thiazol-2-yl)-benzaldehyde; TLC: Rf=0.21 (hexane/ethyl acetate=3:1); m.p. 91–92° C.

EXAMPLE 58

Analogously to Example 32, 521 mg (2.00 mmol) of 3-amino-4-(3-chlorophenylamino)-1H-pyrazolo[3,4-d]pyrimidine (see Step 1.6) and 343 µl of acetic acid are dissolved in 50 ml of methanol and reacted with 567 mg (3.0 mmol) of 4-(thiazol-5-yl)-benzaldehyde to form 4-(3-chloro-phenylamino)-3-[{4-(thiazol-5yl)-phenyl}-methyleneamino]-1H-pyrazolo[3,4-d]pyrimidine. Reduction of the above intermediate in 30 ml of DMEU with 16 ml (16 mmol) of DIBAL-H, analogous working-up and digestion in diethyl ether yield 4-(3-chloro-phenylamino)-3-[4-(thiazol-5-yl)-benzylamino]-1H-pyrazolo[3,4-d]pyrimidine; m.p. 235° C.; TLC: Rf=0.42 ($CHCl_3$/methanol/$H_2O$/acetic acid=85:13:1.5:0.5); HPLC: $t_{Ret}$(grad$_{20-100}$)=8.5; FABMS: $(M+H)^+$=434.

The starting material is prepared as follows:
Step 58.1:

In a bomb tube, a mixture of 3.7 g (20 mmol) of 4-bromo-benzaldehyde, 6.64 ml (93 mmol) of thiazole, 2.94 g of potassium acetate and 1.16 g (1 mmol) of Pd(PPh$_3$)$_4$ is stirred in 50 ml of dimethylacetamide at 150° C. for 12 hours. The reaction mixture is concentrated by evaporation; water is added to the residue and the mixture is extracted three times with methylene chloride. The organic phases are filtered through cotton wadding, concentrated by evaporation and chromatographed ($SiO_2$; hexane/ethyl acetate=1:2): 4-(Thiazol-5-yl)-benzaldehyde is obtained; HPLC:$t_{Ret}$(grad$_{20-100/20}$)=11.4.

EXAMPLE 59

Analogously to Example 32, 521 mg (2.00 mmol) of 3-amino-4-(3-chlorophenylamino)-1H-pyrazolo[3,4-d]pyrimidine (see Step 1.6) and 343 µl of acetic acid are dissolved in 50 ml of methanol and reacted with 565 mg (3.0 mmol) of 3-(2-methyl-tetrazol-5-yl)-benzaldehyde to form 4-(3-chloro-phenylamino)-3-[{3-(2-methyl-tetrazol-5-yl)-phenyl}-methyleneamino]-1H-pyrazolo[3,4-d]pyrimidine. Reduction of the above intermediate in 30 ml of DMEU with 16 ml (16 mmol) of DIBAL-H, analogous working-up and digestion in methanol yield 4-(3-chloro-phenylamino)-3-[3-(2-methyl-tetrazol-5-yl)-benzylamino]-1H-pyrazolo[3,4-d]pyrimidine; TLC: $R_f$=0.51 ($CHCl_3$/methanol/$H_2O$/acetic acid=85:13:1.5:0.5); HPLC: $t_{Ret}$(grad$_{20-100}$)=8.7; FAB-MS: $(M+H)^+$=433.

The starting material is prepared as follows:
Step 59.1:

5.8 g (42.1 mmol) of triethylamine hydrochloride and 6.0 g (92.3 mmol) of sodium azide are added to a solution of 4.0 g (30.5 mmol) of 3cyano-benzaldehyde in 100 ml of 1-methyl-2-pyrrolidone and heated at 110° C. for 1.5 hours (argon atmosphere). When cool the reaction mixture is poured into 0.6 liter of ice/37% HCl (20:1) and stirred thoroughly to complete the reaction. Extraction with 3 portions of ethyl acetate, washing the organic phases with 3× water and brine, drying ($Na_2SO_4$), concentration by evaporation and stirring in diethyl ether yield 3-(tetrazol-5-yl)-benzaldehyde; m.p. 185–189° C.; TLC: $R_f$=0.13 ($CHCl_3$/methanol/$H_2O$/acetic acid=85:13:1.5:0.5).

Step 59.2:

With the exclusion of air, 10.0 g (57.4 mmol) of 3-(tetrazol-5-yl)-benzaldehyde are added to 23.7 g (172 mmol) of potassium carbonate in 120 ml of DMF/dioxane (1:1) in an ice bath. 5.37 ml (86 mmol) of methyl iodide are added dropwise thereto and the reaction mixture is stirred for 2 hours in the ice bath and for 1 hour at RT. The reaction mixture is stirred into 0.5 liter of water, and the crude product is filtered off with suction and washed with water. Dissolution in 0.3 liter of ethyl acetate, washing with brine, drying ($Na_2SO_4$), concentration by evaporation and stirring in diethyl ether yield 3-(2-methyl-tetrazol-5-yl)-benzaldehyde; TLC: $R_f$=0.47 (hexanelethyl acetate=3:1).

EXAMPLE 60

Analogously to Example 32, 521 mg (2.00 mmol) of 3-amino-4-(3-chlorophenylamino)-1H-pyrazolo[3,4-d]pyrimidine (see Step 1.6) and 343 µl of acetic acid are dissolved in 50 ml of methanol and reacted with 691 mg (3.0 mmol) of 3-(2-tert-butyl-tetrazol-5-yl)-benzaldehyde to form 4-(3-chloro-phenylamino)-3-[{3-(2-tert-butyl-tetrazol-5-yl)-phenyl}-methyleneamino]-1H-pyrazolo[3,4-d]pyrimidine. Reduction of the above intermediate in 30 ml of DMEU with 16 ml (16 mmol) of DIBAL-H, analogous working-up and digestion in methanol yield 4(3-chloro-phenylamino)-3-[3(2-tert-butyl-tetrazol-5-yl)-benzylamino]1H-pyrazolo[3,4-d]pyrimidine; TLC: $R_f$=0.60 ($CHCl_3$/methanol/$H_2O$/acetic acid=85:13:1.5:0.5); HPLC: $t_{Ret}$(grad$_{20-100}$)=10.3.

The starting material is prepared as follows:
Step 60.1:

In an autoclave, 3.2 g (18.4 mmol) of 3-(tetrazol-5-yl)-benzaldehyde (see Step 59.1) in 22 ml of toluene are heated at 110° C. for 1.5 hours with ≈1.5 g of isobutene and 0.216 ml of methanesulfonic acid. When cold the reaction mixture is diluted with 200 ml of ethyl acetate, washed four times with water and once with brine, dried ($Na_2SO_4$) and concentrated by evaporation. Column chromatography ($SiO_2$; hexane/ethyl acetate=3:1) and crystallization from diethyl ether/hexane (−15° C.) yield 3-(2-tert-butyl-tetrazol-5-yl)-benzaldehyde; TLC: Rf=0.41 (hexane/ethyl acetate=3:1); FAB-MS: $(M+H)^+$=231.

EXAMPLE 61

Analogously to Example 32, 521 mg (2.00 mmol) of 3-amino-4-(3-chlorophenylamino)-1H-pyrazolo[3,4-d]pyrimidine and 343 µl of acetic acid are dissolved in 50 ml of methanol and reacted with 565 mg (3.0 mmol) of 2-(2-methyl-tetrazol-5-yl)-benzaldehyde to form 4-(3-chlorophenylamino)-3-[{2-(2-methyl-tetrazol-5-yl-phenyl}-methyleneamino]-1H-pyrazolo[3,4-d]pyrimidine. The above intermediate is reduced in 30 ml of DMEU with 16 ml (16 mmol) of DIBAL-H and the reaction mixture is hydrolyzed analogously. The DMEU solution is poured into water and extracted with ethyl acetate. The organic phase yields, after washing seven times with water and once with brine, drying ($Na_2SO_4$), concentration by evaporation and digestion in diethyl ether, 4-(3-chloro-phenylamino)-3-[2-(2-methyl-tetrazol-5-yl)-benzylamino]-1H-pyrazolo[3,4-d]pyrimidine; TLC: $R_f$=0.47 ($CHCl_3$/methanol/$H_2O$/acetic acid=85:13:1.5:0.5); HPLC: $t_{Ret}(grad_{20-100})$=9.0; FAB-MS: $(M+H)^+$=433.

The starting material is prepared as follows:

Step 61.1:

20.3 g (147 mmol) of triethylamine hydrochloride and 21.0 g (322 mmol) of sodium azide are added to a solution of 14.0 g (107 mmol) of 2-cyano-benzaldehyde in 350 ml of 1-methyl-2-pyrrolidone and heated at 110° C. for 3 hours (argon atmosphere). The black reaction solution is poured into 0.6 liter of ice/37% HCl (20:1) and stirred thoroughly to complete the reaction. Extraction with 3 portions of ethyl acetate, washing the organic phases with 3× water and brine, drying ($Na_2SO_4$), concentration by evaporation and stirring in diethyl ether yield 2-(tetrazol-5-yl)-benzaldehyde; m.p. 130° C.; TLC: $R_f$=0.10 ($CHCl_3$/methano/$H_2O$/acetic acid=85:13:1.5:0.5).

Step 61.2: With the exclusion of air, 8.0 g (45.9 mmol) of 2-(tetrazol-5-yl)-benzaldehyde are added to 19 g (138 mmol) of potassium carbonate in 100 ml of DMF/dioxane (1:1) in an ice bath. 4.25 ml (68 mmol) of methyl iodide are added dropwise thereto and the reaction mixture is stirred in the ice bath for 1 hour and at RT for 1.5 hours. The mixture is stirred into 1 liter of icewater and 0.6 liter of ethyl acetate and the aqueous phase is separated off and extracted twice more with ethyl acetate. The organic phases are washed four times with water and with brine, dried ($Na_2SO_4$) and concentrated by evaporation. Column chromatography ($SiO_2$; hexane/ethyl acetate=3:1) and stirring in hexane yield 2-(2-methyl-tetrazol-5-yl)-benzaldehyde; TLC: Rf=0.41 (hexanelethyl acetate=3:1); FAB-MS: $(M+H)^+$=189.

EXAMPLE 62

Analogously to Example 32, 521 mg (2.00 mmol) of 3-amino-4-(3-chloro-phenylamino)-1H-pyrazolo[3,4-d]pyrimidine (see Step 1.6) and 343 µl of acetic acid are dissolved in 50 ml of methanol and reacted with 691 mg (3.0 mmol) of 2-(2-tert-butyl-tetrazol-5-yl)-benzaldehyde to form 4-(3-chloro-phenylamino)-3-[(2-(2-tert-butyl-tetrazol-5-yl)-phenyl}-methyleneamino]-1H-pyrazolo[3,4-d]pyrimidine. Reduction of the above intermediate in 30 ml of DMEU with 16 ml (16 mmol) of DIBAL-H and analogous working-up yield 4-(3-chloro-phenylamino)-3-[2-(2-tert-butyl-tetrazol-5-yl)-benzylamino]-1H-pyrazolo[3,4d]pyrimidine; TLC: $R_f$=0.64 ($CHCl_3$/methanol/$H_2O$/acetic acid=85:13:1.5:0.5); HPLC: $t_{Ret}(grad_{20-100})$=10.3.

The starting material is prepared as follows:

Step 62.1:

In an autoclave, 6.4 g (36.7 mmol) of 2-(tetrazol-5-yl)-benzaldehyde (Step 61.1) in 50 ml of toluene are heated at 110° C. for 1.5 hours with ≈3 g of isobutene and 0.432 ml of methanesulfonic acid. When cold the reaction mixture is diluted with 300 ml of ethyl acetate, washed four times with water and once with brine, dried ($Na_2SO_4$) and concentrated by evaporation. Column chromatography ($SiO_2$; hexane/ethyl acetate=4:1) and crystallization from hexane with a small amount of diethyl ether at −20° C. yield 2-(2-tert-butyl-tetrazol-5-yl)-benzaldehyde; TLC: $R_f$=0.36 (hexane/ethyl acetate=10:1).

EXAMPLE 63

With gentle heating, 195 mg (0.75 mmol) of 3-amino-4-(3-chloro-phenylamino)-1H-pyrazolo[3,4-d]pyrimidine (see Step 1.6) and 135 mg of acetic acid are dissolved in 20 ml of methanol. Then, at RT, 1.0 mmol of tetrazole-5-carbaldehyde is added and the reaction mixture is stirred overnight to complete the reaction, during which a solid separates out. Concentration by evaporation to approximately half volume and filtration yield 4-(3-chloro-phenylamino)-3-[(tetrazol-5-yl)-methyleneamino]-1H-pyrazolo[3,4-d]pyrimidine. More material can be recovered from the mother liquor by concentration by evaporation and stirring the residue in isopropanol. Under a nitrogen atmosphere, 208 mg of the above intermediate are dissolved in 27 ml of DMEU and, with ice cooling, 4.2 ml (4.2 mmol) of DIBAL-H are added and the mixture is stirred for 7 hours. 13 ml of ethyl acetate are added and the mixture is stirred for 30 min and diluted with 130 ml of methanol. 0.9 ml of water and 9 g of $Na_2SO_4$ are added to the precipitate, followed by stirring for 30 min and then filtration. The filtrate is concentrated by evaporation (RV, HV) and chromatographed ($SiO_2$; $CH_2Cl_2$/-methanol=4:1) and the crude product is stirred in isopropanol/diethyl ether to yield 4-(3-chloro-phenylamino)-3-[(tetrazol-5-yl)-methylamino]-1H-pyrazolo[3,4-d]pyrimidine:HPLC: $t_{Ret}(grad_{20-100})$=6.7; FAB MS $(M+H)^+$=343.

The starting material is prepared as follows:

Step 63.1:

With the exclusion of moisture, 420 g of sodium acetate are added to 167 ml of hydroxy-acetonitrile (70% in water) and 1.2 liters of diethyl ether. With ice cooling, 244 ml of acetyl chloride are added dropwise and the reaction mixture is stirred at RT for 5 hours. The mixture is filtered and the filtrate is concentrated by evaporation under mild conditions. Distillation of the residue yields acetoxy-acetonitrile; b.p.: 80° C. (30 mbar).

Step 63.2:

With the exclusion of moisture, 70 g (0.7 mol) of acetoxy-acetonitrile and 146 g (2.25 mol) of sodium azide are placed in 200 ml of THF. In a second apparatus, with ice-cooling 107 g (0.8 mol) of anhydrous aluminum chloride are introduced in portions into 1 liter of THF (exothermic). That solution is then added dropwise to the acetoxy-acetonitrile solution. The mixture is then heated at boiling for 25 hours. At 5° C., 40 ml of 5N HCl, 300 ml of methanol and a further 300 ml of 5N HCl are added dropwise (pH=1, $HN_3$ destroyed!). Nitrogen is passed through the apparatus for 2 hours, followed by filtration and washing with methanol. The filtrate is concentrated by evaporation and the evaporation residue is extracted three times with hot ethyl acetate and once with acetone. Partial concentration of the ethyl acetate/acetone extracts by evaporation (⇒ crystallization), filtration and stirring in diethyl ether yield 5-hydroxymethyl-tetrazole; m.p. 180–181° C.

Step 63.3:

15 g (0.15 mol) of 5-hydroxymethyl-tetrazole and 90 g of manganese dioxide (Aldrich; Milwaukee/USA) are stirred in 1.5 liters of acetone at RT for 13 days. The reaction mixture is then filtered through Hyflo and the residue is washed with a large amount of acetone and finally methanol. Concentration of the acetone extract by evaporation yields tetrazole-5-carbaldehyde; $^1$H-NMR (acetone-$d_6$): 10.26 (s, 1H), 5.02 (s, 1H).

EXAMPLE 64

In accordance with the processes described in this text, 4-(3-chloro-phenyl-amino)-3-[(2-methyl-tetrazol-5-yl)-methylamino]-1H-pyrazolo[3,4-d]pyrimidine is obtained.

EXAMPLE 65

In accordance with the processes described in this text, 4-(3-chloro-phenyl-amino)-3-[(2-tert-butyl-tetrazol-5-yl)-methylamino]-1H-pyrazolo[3,4-d]pyrimidine is obtained.

EXAMPLE 66

With the exclusion of moisture, 261 mg (1.00 mmol) of 3-amino-4-(3-chloro-phenylamino)-1H-pyrazolo[3,4-d]pyrimidine (see Step 1.6) are dissolved in 2.5 ml of dioxane and 1 ml of DMEU; 138 µl (1.1 mmol) of benzyl isocyanate are added and the reaction mixture is stirred at RT overnight. The dioxane is evaporated off from the reaction mixture in a rotary evaporator. The resulting yellow solution is poured into 75 ml of water and the product that precipitates is filtered off. Stirring in boiling ethyl acetate yields 3-(benzylamino-carbonylamino)-4-(3-chloro-phenylamino)-1H-pyrazolo[3,4-d]pyrimidine; HPLC:$t_{Ret}$ (grad$_{20-100}$)=9.5; FAB-MS: (M+H)$^+$=394.

EXAMPLE 67

With the exclusion of moisture, 261 mg (1.00 mmol) of 3-amino-4-(3-chlorophenylamino)-1H-pyrazolo[3,4-d]pyrimidine (see Step 1.6) are dissolved in 2.5 ml of dioxane and 1 ml of DMEU; 137 I (1.1 mmol) of 3-chloro-phenyl isocyanate are added and the reaction mixture is stirred overnight at RT and finally for 16 hours at 60° C. Since, according to HPLC, not all of the pyrazolo-pyrimidine has reacted, a further 40 all of 3chloro-phenyl isocyanate are added and the mixture is stirred for a further 20 hours at 60° C. Working-up analogously to Example 66 and stirring in hot ethanol yield 4-(3-chloro-phenylamino)-3-[(3-chloro-phenyl-amino)-carbonylamino]-1H-pyrazolo[3,4-d]pyrimidine; HPLC: $t_{Ret}$(grad$_{20-100}$)=12.4; FARMS: (M+H)$^+$=414.

EXAMPLE 68

With the exclusion of moisture, 261 mg (1.00 mmol) of 3-amino-4-(3-chlorophenylamino)-1H-pyrazolo[3,4-d]pyrimidine (see Step 1.6) are dissolved in 2.5 ml of dioxane and 1 ml of DMEU; 202 mg (1.1 mmol) of 4-chloro-2-methyl-phenyl isothiocyanate (Maybridge) are added and the reaction mixture is stirred overnight at RT and finally for 16 hours at 60° C. Working-up analogously to Example 66 and stirring in DMSO/ethyl acetate yield 3-[(4-chloro-2-methyl-phenyl-amino)-thiocarbonyl-amino]-4-(3-chloro-phenylamino)-1H-pyrazolo[3,4-d]pyrimidine; HPLC: $t_{Ret}$ (grad$_{20-100}$)=12.2; FAB-MS: (M+H)$^+$=444.

EXAMPLE 69

With the exclusion of moisture, 261 mg (1.00 mmol) of 3-amino-4-(3-chloro-phenylamino)-1H-pyrazolo[3,4-d]pyrimidine (see Step 1.6) are dissolved in 2.5 ml of dioxane and 1 ml of DMEU; 161 µl (1.1 mmol) of 1-naphthyl isocyanate are added and the reaction mixture is stirred overnight at RT. Working-up analogously to Example 66 yields 4-(3-chloro-phenylamino)-3-[(naphth-1-yl-amino)-carbonylamino]-1H-pyrazolo[3,4-d]pyrimidine; HPLC: $t_{Ret}$ (grad$_{20-100}$)=12.0; FAB-MS: (M+H)$^+$=430.

EXAMPLE 70

With the exclusion of moisture, 261 mg (1.00 mmol) of 3-amino-4-(3-chlorophenylamino)-1H-pyrazolo[3,4-d]pyrimidine are dissolved in 2.5 ml of dioxane and 1 ml of DMEU; 160 µl (1.1 mmol) of n-hexyl isocyanate are added and the reaction mixture is stirred overnight at RT. The dioxane is then evaporated off in a rotary evaporator and 30 ml of DIPE and 40 ml of hexane are added to the residue. Filtration with suction and washing with DIPE/hexane yield 4-(3chloro-phenylamino)-3-[(n-hexyl-amino)-carbonyl-amino]-1H-pyrazolo[3,4-d]pyrimidine; HPLC:$t_{Ret}$ (grad$_{20-100}$)=10.3; FAB-MS: (M+H)$^+$=388.

EXAMPLE 71

Analogously to Example 70, 4-(3-chloro-phenylamino)-3-(pyrid-3-yl-methylamino)-carbonyl-amino]-1H-pyrazolol-3,4-d]pyrimidine is obtained.

EXAMPLE 72

Analogously to Example 34, 261 mg (1.00 mmol) of 3-amino-4-(3-chloro-phenylamino)-1 H-pyrazolo[3,4-d]pyrimidine (see Step 1.6), 168 mg (1.5 mmol) of cyclohexanecarbaldehyde and 180 mg of acetic acid are stirred in 39 ml of DMEU/methanol (1:2) and then reacted with 440 mg (7 mmol) of NaCNBH$_3$. Stirring in DIPE yields 4-(3-chloro-phenylamino)-3-(cyclohexyl-methyl-amino)-1H-pyrazolo[3,4-d]pyrimidine; m.p. 188–190° C.; HPLC: $t_{Ret}$ (grad$_{20-100/20}$)=12.8; FAB-MS: (M+H)$^+$=357.

EXAMPLE 73

Analogously to Example 34, 261 mg (1.00 mmol) of 3-amino-4-(3-chlorophenylamino)-1H-pyrazolo[3,4-d]pyrimidine (see Step 1.6), 129 mg (1.5 mmol) of pivaldehyde and 180 mg of acetic acid are stirred in 39 ml of DMEU/methanol (1:2) and then reacted with 440 mg (7 mmol) of NaCNBH$_3$. Since, according to HPLC, the reaction is incomplete, 129 mg of pivaldehyde, 180 mg of acetic acid and 440 mg of NaCNBH$_3$ are added a number of times until HPLC indicates that all the pyrazolo-pyrimidine has reacted. Between the individual additions, the reaction mixture is stirred at boiling temperature for 20 hours each time. Analogous working-up and stirring in hexane yield 4-(3-chloro-phenylamino)-3-(2,2-dimethylpropyl-amino)-1H-pyrazolo[3,4-d]pyrmidine; m.p. 229–231° C.; HPLC: $t_{Ret}$ (grad$_{20-100/20}$)=11.6; FAB-MS: (M+H)$^+$=331.

EXAMPLE 74

Analogously to Example 34, 261 mg (1.00 mmol) of 3-amino-4-(3-chlorophenylamino)-1H-pyrazolo[3,4-d]pyrimidine (see Step 1.6), 150 mg (1.5 mmol) of capronaidehyde and 180 mg of acetic acid are stirred in 39 ml of DMEU/methanol (1:2) and then reacted with 440 mg (7 mmol) of NaCNBH$_3$. Stirring in DIPE yields 4-(3-chloro-phenyl-amino)-3-(n-hexyl-amino)-1H-pyrazolo[3,4-d]pyrimidine; HPLC: $t_{Ret}$(grad$_{20-100}$)=9.9; FAB-MS: (M+H)$^+$=345.

EXAMPLE 75

Analogously to Example 32, 260 mg (1.00 mmol) of 3-amino-4-(3-chlorophenylamino)-1H-pyrazolo[3,4-d]

pyrimidine and 172 μl of acetic acid are dissolved in 25 ml of methanol and reacted with 261 mg (1.5 mmol) of 3-(tetrazol-5-yl)-benzaldehyde (Step 59.1) to form 4-(3-chloro-phenylamino)-3-{[3-(tetrazol-5-yl)-phenyl]-methyleneamino}-1H-pyrazolo[3,4-d]pyrimidine. With ice-cooling, 8 ml (8 mmol) of DIBAL-H are added to the above intermediate in 15 ml of DMEU and the reaction mixture is stirred for 30 min. 15 ml of ethyl acetate are added and the mixture is stirred for 15 min, diluted with 150 ml of methanol and 1 ml of water and concentrated by evaporation in a rotary evaporator. The residue is poured into 0.5 liter of water and 0.5 liter of ethyl acetate, and acidified to pH=3 with 1 N HCl, and the aqueous phase is separated off and extracted a further 3× with ethyl acetate. The organic phases are washed several times with water and finally with brine, dried ($Na_2SO_4$) and concentrated by evaporation. Stirring in ether yields 4-(3-chloro-phenylamino)-3-[3-(tetrazol-5-yl)-benzylamino-]-1H-pyrazolo[3,4-d]pyrimidine; TLC: $R_f$=0.13 ($CHCl_3$/methanol/$H_2O$/acetic acid=85:13:1.5:0.5); HPLC: $t_{Ret}(grad_{20-100})$=7.4; FAB-MS: $(M+H)^+$=419.

EXAMPLE 76

Analogously to Example 32, 521 mg (2.00 mmol) of 3-amino-4-(3-chlorophenylamino)-1H-pyrazolo[3,4-d]pyrimidine and 343 μl of acetic acid are dissolved in 50 ml of methanol and reacted with 523 mg (3.0 mmol) of 2-(tetrazol-5-yl)-benzaldehyde (Step 61.1) to form 4-(3-chloro-phenylamino)-3-{[2-(tetrazol-5-yl)-phenyl]-methyleneamino}-1H-pyrazolo[3,4-d]pyrimidine. The above intermediate is reduced in 30 ml of DMEU with 16 ml (16 mmol) of DIBAL-H and the reaction mixture is hydrolyzed analogously. The DMEU solution is poured into water, adjusted to pH=3 with 1 N HCl and extracted with ethyl acetate. The organic phase yields, after washing 10× with water and 1× with brine, drying ($Na_2SO_4$), concentration by evaporation and digestion in diethyl ether, 4-(3-chloro-phenylamino)-3-[2-(tetrazol-5-yl)-benzylamino]-1H-pyrazolo-[3,4-d]pyrimidine; TLC: Rf=0.19 ($CHCl_3$/methanol/$H_2O$/acetic acid=85:13:1.5:0.5); HPLC: $t_{Ret}(grad_{20-100})$=7.7; FAB-MS: $(M+H)^+$=419.

EXAMPLE 77

A mixture of 200 mg (0.521 mmol) of 3-(4-aminomethyl-phenylamino)-4-(3-chloro-phenylamino)-1H-pyrazolo[3,4-d]pyrimidine hydrate, 0.061 ml (0.548 mmol) of butyl isocyanate and 5 ml of THF is stirred at 20° C. for 15 hours and then concentrated by evaporation in vacuo. The residue is digested in 5 ml of boiling methanol, cooled to 5° C. and filtered, yielding 3-[4-(n-butylamino-carbonylamino-methyl)-phenylamino]-4-(3-chloro-phenyl-amino)-1H-pyrazolo[3,4-d]pyrimidine; m.p. 217–218° C.

The starting material is obtained as follows:
Step 77.1:
A mixture of 86.1 g (505.6 mmol) of 3,3-bis-methylmercapto-2-cyano-acrylonitrile [for preparation see: Chem. Ber. 95, 2861 (1962)], 112.4 g (505.6 mmol) of 4-(N-Boc-aminomethyl)-aniline [for preparation see: WO 93/00095] and 750 ml of methanol is heated under reflux for 5 hours and then concentrated in vacuo until crystallization begins. After filtration, 3-14-(N-Boc-aminomethyl)-phenylamino]-2cyano-3-methylmercapto-acrylonitrile is obtained; m.p. 154–157° C.; ESI-MS: $(M-H)^-$=343.
Step 77.2:
A mixture of 117.8 g (342 mmol) of 3-[4-(N-Boc-aminomethyl)-phenylamino)2-cyano-3-methylmercaptoacrylonitrile, 20.54 ml (41.45 mmol) of hydrazine hydrate and 750 ml of methanol is heated under reflux for 3 hours and then concentrated by evaporation in vacuo at 50° C., yielding 5-amino-3-[4-(N-Boc-aminomethyl)-phenylamino]-4-cyano pyrazole in the form of an amorphous residue; TLC-$R_f$=0.28 (methylene chloride/methanol [9:1]).
Step 77.3:
A mixture of 117.7 g (341.9 mmol) of 5-amino-3-[4-(N-Boc-aminomethyl)-phenyl-amino]-4-cyano-pyrazole, 76.3 ml (445.2 mmol) of N,N-dimethylformamide diethyl acetal and 1200 ml of toluene is heated under reflux for 5 hours. Cooling to 20° C., filtration and washing the crystals with toluene and diethyl ether yield 3-[4-(N-Boc-aminomethyl)-phenylamino]-4-cyano-5-dimethylamino-methyleneamino-pyrazole; m.p. 227–228° C.; ESI-MS: $(M-H)^-$=382.
Step 77.4:
A mixture of 94 g (245.1 mmol) of 3-[4-(N-Boc-aminomethyl)-phenylamino]-4-cyano-5-dimethylamino-methyleneamino-pyrazole, 44.2 g (269.4 mmol) of 3-chloro-aniline hydrochloride [for preparation see: Justus Liebigs Ann. Chem. 176, 45 (1875)] and 1000 ml of ethanol is heated under reflux for 60 hours and then concentrated by evaporation in vacuo. The residue is dissolved in ethyl acetate, and the organic phase is washed with ice-cold 0.5N hydrochloric acid, water and brine, dried over sodium sulfate and concentrated by evaporation in vacuo. After recrystallization of the residue from ethyl acetate/hexane and from methanolimethylene chloride, 3-[4-(N-Boc-aminomethyl)-phenylamino]-4-(3-chloro-phenylamino)-1H-pyrazolo[3,4-d]pyrimidine is obtained; m.p. 196° C.; ESI-MS: $(M-H)^-$=464.
Step 77.5:
A mixture of 25 g (53.65 mmol) of 3-[4-{N-tert-butyloxycarbonyl}-aminomethyl]-phenylamino]-4-(3-chloro-phenylamino)-1H-pyrazolo[3,4-d]pyrimidine and 350 ml of 3N methanolic hydrochloric acid is stirred at 50° C. for 30 min. The reaction mixture is then allowed to cool to RT and filtered, and the filter residue is washed with methanol and diethyl ether and the filtration residue is partitioned between saturated aqueous sodium carbonate solution and ethyl acetate. The organic phase is washed with water and brine, dried over sodium sulfate, filtered, and concentrated by evaporation in vacuo. After recrystallization of the residue from methanol/water, 3-(4-aminomethyl-phenylamino)-4-(3-chloro-phenylamino)-1H-pyrazolo[3,4-d]pyrimidine is obtained in the form of the monohydrate; m.p. 207–209° C.; ESI-MS: $(M+H)^+$=366.

EXAMPLE 78

A mixture of 115 mg (0.3 mmol) of 3-(4-aminomethyl-phenylamino)-4-(3chloro-phenylamino)-1H-pyrazolo-[3,4-d]pyrimidine hydrate (see Step 77.5), 0.041 ml (0.318 mmol) of 3-methoxy-phenyl isocyanate and 4 ml of THF is stirred at 20° C. for 15 hours and then concentrated by evaporation in vacuo. After recrystallization of the residue from ethyl acetate/hexane, 4-(3-chloro-phenylamino)-3-{4-[(3-methoxy-phenyl-amino)-carbonylamino-methyl]-phenylamino}-1H-pyrazolo-[3,4-d]pyrimidine is obtained in the form of the monohydrate; m.p. 157–160° C.; ESI-MS: $(M-H)^-$=513.

EXAMPLE 79

A mixture of 150 mg (0.391 mmol) of 3-(4-aminomethyl-phenylamino)-4-(3-chloro-phenylamino)-1H-pyrazolo[3,4-d]pyrimidine hydrate (see Step 77.5), 34.3 mg (0.483 mmol) of ethyl isocyanate and 5 ml of THF is stirred at 20° C. for 15 hours and then 4 ml of diethyl ether are added Filtration and washing the filter residue with diethyl ether yield 4-(3-chloro-phenylamino-3-14-(ethylamino-carbonylamino-methyl)-phenylamino]-1H-pyrazolo[3,4-d] pyrimidine having a water content of 0.61%; m.p. 228–230° C. (decomp.); ESI-MS: (M–H)$^-$=435.

EXAMPLE 80

A mixture of 150 mg (0.391 mmol) of 3-(4-aminomethyl-phenylamino)-4-(3chloro-phenylamino)-1H-pyrazolo[3,4-d]pyrimidine hydrate (see Step 77.5), 31.4 mg (0.429 mmol) of methyl isothiocyanate and 5 ml of THF is stirred at 20° C. for 15 hours. Concentration to a volume of about 1 ml, addition of 5 ml of diethyl ether to the concentrate and filtration yield 4-(3-chloro-phenylamino)-3-[4-(methylamino-thiocarbonylamino-methyl)phenylamino]-1H-pyrazolo[3,4-d]pyrimidine having a water content of 1.22%; m.p. 216–218° C. (decomp.), ESI-MS: (M–H)$^-$=437.

EXAMPLE 81

A solution of 57.4 mg (0.573 mmol) of succinic anhydride in 0.5 ml of THF is added dropwise, with stirring, to a suspension, cooled to 0° C., of 200 mg (0.521 mmol) of 3-(4-aminomethyl-phenylamino)-4-(3-chloro-phenylamino)-1H-pyrazolo[3,4-d]pyrimidine hydrate (see Step 77.5) in 3 ml of THF. The reaction mixture is stirred at RT for 4 hours and then a further solution of 57.4 mg (0.573 mmol) of succinic anhydride in 0.5 ml of THF is added. The mixture is stirred for a further 3 hours at 40° C., then allowed to cool to RT and filtered, and the filter residue is washed with diethyl ether. 3-[4-({3-Carboxy-propionyl}-aminomethyl)-phenylamino]-4-(3-chlorophenylamino)-1H-pyrazolo[3,4-d]pyrimidine having a water content of 2.45% is obtained; m.p. 205–207° C.; ESI-MS: (M–H)$^-$=464.

EXAMPLE 82

A solution of 0.0503 ml (0.548 mmol) of dimethylcarbamoyl chloride in 0.5 ml of THF is added dropwise, with stirring, to a suspension, cooled to 0° C., of 150 mg (0.391 mmol) of 3-(4-aminomethyl-phenylamino)4-(3-chloro-phenylamino)-1H-pyrazolo-[3,4-d]pyrimidine hydrate (see Step 77.5) in 2.5 ml of THF and 0.079 ml (0.567 mmol) of triethylamine. The reaction mixture is stirred at RT for 17 hours and then filtered, and the filter residue is washed in succession with THF, water, THF and diethyl ether. 4-(3-Chloro-phenylamino)-3-[4-(dimethylamino-carbonylamino-methyl)-phenylamino]-1H-pyrazolo[3,4-d] pyrimidine having a water content of 1.22% is obtained; m.p. 238–240° C.; ESI-MS: (M+H)$^+$=437.

EXAMPLE 83

A mixture of 150 mg (0.391 mmol) of 3-(4-aminomethyl-phenylamino)-4-(3chloro-phenylamino)-1H-pyrazolo[3,4-d]pyrimidine hydrate (see Step 77.5), 95 mg (1.17 mmol) of potassium cyanate, 3 ml of ethanol, 3 ml of water and 0.0258 ml (0.451 mmol) of acetic acid is heated under reflux for 1 hour. After cooling to about 20° C., filtration and recrystallization of the filtration residue from methanol/water, 4-(3-chloro-phenylamino)-3-(4-{ureido-methyl}-phenylamino)-1H-pyrazolo[3,4-d]pyrimidine is obtained; m.p. >280° C.; FAB-MS: (M+H)$^+$=409.

EXAMPLE 84

A mixture of 300 mg (0.782 mmol) of 3-(4-aminomethyl-phenylamino)-4-(3-chloro-phenylamino)-1H-pyrazolo[3,4-d]pyrimidine hydrate (see Step 77.5), 223 mg (0.819 mmol) of Boc-glycine hydroxysuccinimide ester (Fluka) and 5 ml of THF is stirred at 20° C. for 1.5 hours. Filtration and washing the filter residue with THF and diethyl ether yield 3-[4-(N-{N-tert-butyloxycarbonyl-glycyl}-aminomethyl)-phenylamino]-4-(3-chlorophenylamino)-1H-pyrazolo[3,4-d]pyrimidine having a water content of 1.02%; m.p. 205° C.; ESI-MS: (M–H)$^-$=521.

EXAMPLE 85

A mixture of 200 mg (0.521 mmol) of 3-(4-aminomethyl-phenylamino)-4-(3-chlorophenylamino)-1H-pyrazolo[3,4-d]pyrimidine hydrate (see Step 77.5), 157 mg (0.548 mmol) of Boc-L-alanyl hydroxysuccinimide ester (Fluka) and 4 ml of THF is stirred at 20° C. for 1.5 hours. Then 2 ml of diethyl ether and 5 ml of hexane are added to the reaction mixture and stirring is continued at RT for a further 0.5 hour. After filtration and recrystallization of the filter residue from methanol/diethyl ether, 3-[4-(N,N-tert-butyloxycarbonyl-L-alanyl)-aminomethyl)-phenylamino]-4-(3-chloro-phenylamino)-1H-pyrazolo[3,4-d]pyrimidine having a water content of 5.09% is obtained; m.p. 153–155° C.; ESI-MS: (M–H)$^-$=535; [a]$D^{20}$–13.4±2.1° (c 0.47%, methanol).

EXAMPLE 86

A mixture of 250 mg (0.651 mmol) of 3-(4-aminomethyl-phenylamino)-4-(3-chloro-phenylamino)-1H-pyrazolo-[3,4-d]pyrimidine hydrate (see Step 77.5), 214 mg (0.685 mmol) of Boc-L-prolyl hydroxysuccinimide ester (Fluka) and 5 ml of THF is stirred at 20° C. for 15 hours. Then 3 ml of diethyl ether and 2.5 ml of hexane are added to the reaction mixture and stirring is continued at RT for about 0.5 hour. After filtration and recrystallization of the filter residue from acetonitrile, 3-[4-(N-(N-tert-butyloxycarbonyl-L-prolyl}-aminomethyl)-phenylamino]-4-(3-chloro-phenylamino)-1H-pyrazolo[3,4-d]pyrimidine having a water content of 1.73% is obtained; m.p. 160° C.; ESI-MS: (M–H)$^{-561}$; [a]$D^{20}$=30.0±1.90 (c=0.527%, methanol).

EXAMPLE 87

A mixture of 200 mg (0.378 mmol) of 3-[4-(N-{N-Boc-glycyl}-aminomethyl)-phenylamino]-4-(3-chloro-phenylamino)-1H-pyrazolo[3,4-d]pyrimidine (see Example 84), 0.049 ml (0.756 mmol) of methanesulfonic acid, 5 ml of methanol and 4 ml of water is heated under reflux for 6 hours and then concentrated by evaporation in vacuao. After recrystallization of the residue from methanol, 4-(3-chlorophenylamino)-3-[4-(N-glycyl-aminomethyl)-phenylamino]-1H-pyrazolo[3,4-d]pyrimidine dimesylate having a water content of 4.78% is obtained; m.p. 140° C. (decomp.); ESI-MS: (M+H)$^+$=423.

EXAMPLE 88

A mixture of 100 mg (0.177 mmol) of 3-[4-(N-{N-Boc-L-alanyl}-aminomethyl)-phenylamino]-4-(3-chloro-phenylamino)-1H-pyrazolo[3,4-d]pyrimidine (see Example 85) and 4 ml of 3N methanolic hydrochloric acid is stirred at 20° C. for 15 hours and then about 5 ml of diethyl ether are added. Filtration and washing the filter residue with diethyl ether yield 4(3chloro-phenylamino)-3-[4-(N-{L-alanyl)-aminomethyl)-phenylamino]-1H-pyrazolo[3,4-d]-pyrimidine.1.9 hydrochloride having a water content of 6.36%; m.p. 220° C. (decomp.); ESI-MS: (M+H)$^+$=437; [a]$_D^{20}$=–1.4=2.0° (c=0.508%, methanol).

EXAMPLE 89

A mixture of 110 mg (0.192 mmol) of 3-4(N-[N-Boc-L-prolyl}-aminomethyl)phenylamino]-4-(3-chloro-phenylamino)-1H-pyrazolo[3,4-d]pyrimidine (see Example 86) and 3.5 ml of 3N methanolic hydrochloric acid is stirred at 20° C. for 3 hours and then about 3.5 ml of diethyl ether are added. Filtration and washing the filter residue with diethyl ether yield 4-(3-chloro-phenylamino)-3-[4-(N-{L-prolyl}-aminomethyl)-phenylamino]-1H-pyrazolo[3,4-d]-pyrimidine.1.6 hydrochloride having a water content of 6.1%; m.p. 230–235° C. (decomp.); ESI-MS: (M+H)$^+$=463; $[a]_D^{20}$=−28.0±2.0° (c=0.49%, methanol).

EXAMPLE 90

A mixture of 500 mg (1.34 mmol) of 3-(3aminomethyl-phenylamino)4-(3-chloro-phenylamino)-1H-pyrazolo[3,4-d]pyrimidine (water content: 1.79%), 402 mg (2.73 mmol) of N,N-dimethylformamide diethyl acetal and 5 ml of methanol is stirred at 30° C. for 2 hours and then concentrated by evaporation in vacuo. Crystallisation of the residue from ethyl acetate, filtration and washing the filter residue with ethyl acetate yield 4-(3-chloro-phenylamino)-3-[3-(dimethylamino-methyleneamino-methyl)-phenylamino]-1H-pyrazolo[3,4-d]pyrimidine having a water content of 1.68%; m.p. 175–177° C.; ESI-MS: (M+H)$^+$=421.

The starting material is obtained as follows:
Step, 90.1:

A mixture of 102.1 g (600 mmol) of 3,3-bis-methylmercapto-2-cyano-acrylonitrile, 133.3 g (600 mmol) of 3-(N-Boc-aminomethyl)-aniline (WO 93/00095) and 1100 ml of methanol is heated under reflux for 6.5 hours and then concentrated by evaporation in vacuo. Crystallization of the residue from ethyl acetate, filtration and washing the filtration residue with ethyl acetate yield 3-[3-(N-Boc-aminomethyl)-phenylamino]-2-cyano-3-methylmercapto-acrylonitrile; m.p. 150–151° C.
Step 90.2:

A mixture of 145.4 g (422 mmol) of 3-[3-(N-Boc-aminomethyl)-phenylamino]-2-cyano-3-methylmercapto-acrylonitrile, 21.96 ml (443 mmol) of hydrazine hydrate and 1000 ml of methanol is heated under reflux for 2 hours and then concentrated by evaporation in vacuo, yielding 5-amino-[3(N-Boc-aminomethyl)-phenylamino]4-cyano-pyrazole; TLC-$R_f$=0.28 (methylene chloride/methanol [9:1]).
Step 90.3:

A mixture of 138.57 g (422 mmol) of 5-amino-3-[3-(N-Boc-aminomethyl)-phenyl-amino]4-cyano-pyrazole, 78.9 ml (460.4 mmol) of N,N-dimethylformamide diethyl acetal, 1350 ml of toluene and 150 ml of ethanol is stirred at 40C for 2 hours. After cooling to 15° C., filtration and washing the crystals with diethyl ether, 3-[3-(N-Boc-aminomethyl)-phenylamino]-4-cyano-5-dimethylamino-methyleneamino-pyrazole is obtained; m.p. 182–184° C.
Step 90.4:

A mixture of 25 g (65.2 mmol) of 3-[3-(N-Boc-aminomethyl)-phenylamino-4-cyano-5-dimethylamino-methyleneamino-pyrazole, 10.7 g (65.2 mmol) of 3-chloro-aniline hydrochloride [for preparation see: Justus Liebigs Ann. Chem. 176, 45 (1875)] and 250 ml of methanol is heated under reflux for 15 hours and then concentrated by evaporation in vacua. The purification of the oily residue is effected by means of flash chromatography on silica gel having a particle size of 0.04–0.06 mm using ethyl acetate. The product-containing fractions are concentrated by evaporation and the residue is recrystallized from methanol, yielding 3-[3-(N-Boc-aminomethyl)-phenylamino]-4-(3-chloro-phenylamino)-1H-pyrazolo-[3,4-d]pyrimidine; m.p. 147–148° C.
Step 90.5:

A mixture of 12 g (25.75 mmol) of 3-[3-(N-Boc-aminomethyl)-phenylamino]-4-(3-chloro-phenylamino)-1H-pyrazolo[3,4-d]pyrimidine and 200 ml of 3N methanolic hydrochloric acid is stirred at RT for 15 hours. The viscous reaction mixture is diluted with methanol and filtered, and the filtration residue is washed with diethyl ether, yielding the crude dihydrochloride of the desired compound (m.p. >260° C.). The dihydrochloride is dissolved in 107 ml of water and, with stirring at RT, 80 ml of a saturated solution of sodium hydrogen carbonate in water are added to the solution. The mixture is stirred at 20° C. for a further 1.5 hours and filtered, and the filter residue is washed with water. After drying under a high vacuum at 120° C., 3-(3-aminomethyl-phenylamino)-4-(3-chloro-phenylamino)-1H-pyrazolo[3,4-d]pyrimidine having a water content of 1.79% is obtained; m.p. 212–214° C.

EXAMPLE 91

A mixture of 300 mg (0.805 mmol) of 3-(3aminomethyl-phenylamino)-4-(3chloro-phenylamino)-1H-pyrazoio[3,4-d]pyrimidine (water content: 1.79%; see Step 90.5), 230 mg (0.845 mmol) of Boc-glycine hydroxysuccinimide ester (Fluka) and 5 ml of THF is stirred at 20° C. for 1.5 hours. The addition of 5 ml of diethyl ether to the reaction mixture, filtration and washing the filter residue with diethyl ether yield 3-13-(N-{N-tert-butyloxy-carbonyl-glycyl}aminomethyl)-phenylamino]4-(3-chloro-phenylamino)-1H-pyrazolo[3,4-d]pyrimidine; m.p. 181–183° C.

EXAMPLE 92

A mixture of 300 mg (0.574 mmol) of 3-[3-(N-{N-Boc-glycyl}-aminomethyl)phenylamino]-4-(3-chloro-phenylamino)-1H-pyrazolo[3,4-d]pyrimidine (see Example 91) and 10 ml of 4N methanolic hydrochloric acid is stirred at 20° C. for 5 hours and then 15 ml of diethyl ether are added. Filtration and washing the filter residue with diethyl ether yield 4-(3-chlorophenylamino)-3-[3(N-glycyl-aminomethyl)-phenylamino]-1H-pyrazolo[3,4d-]-pyrimidine.1.8 hydrochloride having a water content of 6.33%; m.p. 242–245° C.; ESI-MS: (M+H)$^+$=423.

EXAMPLE 93

A mixture of 200 mg (0.537 mmol) of 3(3-aminomethyl-phenylamino)-4-(3-chloro-phenylamino)-1H-pyrazolo[3,4-d]pyrimidine (water content: 1.79%; see Step 90.5) and 10 ml of toluene is concentrated by evaporation in vacuo for the purpose of removing water and, after repetition of that operation, the residue is taken up in 10 ml of toluene. After the addition of 59 mg (0.59 mmol) of succinic anhydride and 0.082 ml (0.59 mmol) of triethylamine, the reaction mixture is heated for 1 hour at 80° C. and for 18 hours under reflux. A further 21 mg (0.21 mmol) of succinic anhydride and 0.041 ml (0.2949 mmol) of triethylamine are added to the reaction mixture which is heated for a further 6 hours under reflux, then cooled to room temperature and 10 ml of diethyl ether are added. Filtration, purification of the filter residue by flash chromatography (silica gel having a particle size of 0.04–0.06 mm; eluant: ethyl acetate), concentration of the product-containing fractions by evaporation in vacuo and recrystallization of the residue from methanol yield 4-(3-chloro-phenylamino)-3-(3-[succinimido-methyl]- phenylamino)-1H-pyrazolo[3,4-d]pyrimidine having a water content of 7.72%; m.p. 140–142° C.; ESI-MS: (M–H)⁻=446.

EXAMPLE 94

A mixture of 250 mg (0.671 mmol) of 3-(3-aminomethyl-phenylamino)-4-(3-chloro-phenylamino)-1H-pyrazolo[3,4-d]pyrimidine (water content: 1.79%; see Step 90.5), 104 mg (1.282 mmol) of potassium cyanate, 1.4 ml of ethanol, 1.4 ml of water and 0.066 ml (1.154 mmol) of acetic acid is heated under reflux for 15 min. After cooling to RT, filtration, washing the filter residue with water and recrystallization from ethanol/diethyl ether/hexane, 4-(3-chloro-phenylamino)-3-(3-[ureido-methyl]-phenylamino)-1H-pyrazolo[3,4-d]pyrimidine having a water content of 1.19% is obtained; m.p. >270° C.; ESI-MS: (M+H)⁺=409.

EXAMPLE 95

A mixture of 300 mg (0.782 mmol) of 3-(4-aminomethyl-phenylamino)-4-(3-chloro-phenylamino)-1H-pyrazolo[3,4-d]pyrimidine hydrate (see Step 77.5) and 15 ml of toluene is concentrated by evaporation in vacuo for the purpose of removing water and, after repetition of that operation, the residue is taken up in 15 ml of toluene. After the addition of 117 mg (1.169 mmol) of succinic anhydride and 0.033 ml (0.237 mmol) of triethylamine the reaction mixture is stirred at 80° C. for 1 hour and heated for 22 hours using a water separator. The reaction mixture is then cooled to RT and about 10 ml of diethyl ether are added; the mixture is filtered and the filtration residue is washed with diethyl ether. The filter residue is then partitioned between ethyl acetate and 25 ml of a saturated solution of sodium hydrogen carbonate in water. After washing of the organic phase with water and brine, drying over sodium sulfate, filtration, and concentration of the filtrate in vacuo, 4-(3-chloro-phenylamino)-3-(4-[succinimido-methyl]-phenylamino)-1H-pyrazolo[3,4-d]pyrimidine precipitates out in crystalline form; m.p. 155–157° C.; FAB-MS: (M+H)⁺=448.

EXAMPLE 96

Analogously to Example 95, starting from 300 mg (0.782 mmol) of 3-(4-amino-methyl-phenylamino)-4-(3-chloro-phenylamino)-1H-pyrazolo[3,4-d]pyrimidine hydrate (see Step 77.5) and 160 mg (1.175 mmol) of phthalic anhydride, with the addition of 0.033 ml (0.237 mmol) of triethylamine, there is obtained 4-(3-chloro-phenylamino)-3-(4-[phthalimido-methyl]-phenylamino)-1H-pyrazolo[3,4d]pyrimidine; m.p. >275° C.; FAB-MS: (M+H)⁺=496.

EXAMPLE 97

Analogously to Example 95, 300 mg (0.805 mmol) of 3-(3-amino-methylphenylamino)-4-(3-chloro-phenylamino)-1H-pyrazolo[3,4-d]pyrimidine (water content: 1.79%; see Step 90.5) and 164 mg (1.205 mmol) of phthalic anhydride are reacted, with the addition of 0.034 ml (0.244 mmol) of triethylamine. The product, which is still slightly contaminated, is converted by means of flash chromatography (silica gel having a particle size of 0.04–0.06 mm; eluant: ethyl acetate), concentration of the product-containing fractions by evaporation in vacuo and recrystallization of the residue from methanol into 4-(3chloro-phenylamino)-3(3-[phthalimido-methyl]-phenylamino)-1H-pyrazolo[3,4]-pyrimidine (water content: 0.9%/o); m.p. 254–256° C.; ESI-MS: (M+H)⁺=496.

EXAMPLE 98

A mixture of 300 mg (0.805 mmol) of 3-(3-aminomethyl-phenylamino)-4-(3-chloro-phenylamino)-1H-pyrazolo[3,4-d]pyrimidine (water content: 1.79%; see Step 90.5), 242 mg (0.845 mmol) of Boc-L-alanyl hydroxysuccinimide ester (Fluka) and 5 ml of THF is stirred at 20° C. for 17 hours. Then about 5 ml of diethyl ether are added to the reaction mixture and stirring is continued at RT for 15 min. Filtration and washing the filter residue with diethyl ether yield 3-[3-(N-{N-tert-butyloxycarbonyl-L-alanyl}-aminomethyl)-phenyl-amino]-4-(3-chloro-phenylamino)-1H-pyrazolo[3,4-d]pyrimidine having a water content of 0.83%; m.p. 150–153° C.; ESI-MS: (M–H)⁻=535; [a]D²⁰=−13.0±1.4 (c=0.783%, methanol).

EXAMPLE 99

A mixture of 300 mg (0.554 mmol) of 3-[3-(N-{N-Boc-L-alanyl}-aminomethyl)-phenylamino]-4-(3-chloro-phenylamino)-1H-pyrazolo[3,4-d]pyrimidine (water content 0.83 %; see Example 98) and 10 ml of 4N methanolic hydrochloric acid is stirred at 20° C. for 21 hours and then concentrated by evaporation in vacuo. Recrystallization of the residue from ethanol/diethyl ether yields 4-(3chloro-phenylamino)-3-[3-(N-{L-alanyl}-aminomethyl)-phenylamino]-1H-pyrazolo[3,4-d]pyrimidine.1.7 hydrochloride having a water content of 6.83%; m.p. 222–225° C.; ESI-MS: (M+H)⁺=437; [a]D²⁰=+1.6±1.1° (c=0.893%, methanol).

EXAMPLE 100

A mixture of 1.65 g (3.86 mmol) of 1-benzyl-4-(3-chloro-phenylamino)-3-(3-pyridylamino)-pyrazolo[3,4]pyrimidine, 3.1 g (23.25 mmol) of anhydrous aluminum chloride and 25 ml of toluene is heated under reflux for 0.5 hour. The reaction mixture is then concentrated by evaporation in vacuo, and the residue is stirred with 40 ml of water and filtered, and the filter residue is washed with water and toluene. The filtration residue is suspended, with heating, in a mixture of 50 ml of ethyl acetate and 15 ml of ethanol, and the suspension is filtered while still warm and the filter residue is washed with ethyl acetate and stirred in 10 ml of 1 N sodium hydroxide solution for about 10 min. Filtration, washing with water and recrystallization of the filter residue twice from isopropyl alcohol yield 4-(3-chloro-phenylamino)-3-(3-pyridylamino)-1-H-pyrazolol-[3,4-d]pyrimidine having a water content of 3.4%; m.p. 233–234° C.

The starting material is prepared as follows:
Step 100.1:
A mixture of 11 g (64.6 mmol) of 3,3-bis-methylmercapto-2-cyano-acrylonitrile, 6 g (63.75 mmol) of 3-amino-pyridine and 50 ml of toluene is stirred at 60° C. for 18 hours. Filtration of the reaction mixture while still warm and washing of the filter residue with toluene yield 2-cyano-3-methylmercapto-3-(3-pyridylamino)-acrylonitrile; m.p. 180–181° C.
Step 100.2:
A mixture of 13.75 g (70.48 mmol) of benzylhydrazine dihydrochloride, 28.2 ml of a 5.4 molar methanolic sodium methanolate solution and 100 ml of ethanol is stirred for 15 min and 12.45 g (57.57 mmol) of 2-cyano-3-methylmercapto-3-(3-pyridylamino)-acrylonitrite are added. The reaction mixture is heated under reflux for 12 hours, cooled to room temperature and filtered, and the filtrate is concentrated by evaporation in vacua. For purification, the residue is dissolved in methylene chloride and the solution is filtered over 200 g of silica gel; the filtrate is again concentrated by evaporation and the residue is subjected to flash chromatography over silica gel having a particle size of 0.035–0.07 mm, using tert-butyl methyl ether and tert-butyl methyl ether/methanol (49:1 and 19:1 and 9:1) as eluant. The product-containing fractions are concentrated by evaporation and the residue is recrystallized from 100 ml of isopropyl alcohol. After repeated recrystallization from isopropyl alcohol, 5-amino-1-benzyl-4-cyano-3-(3-pyridylamino)-pyrazole is obtained; m.p. 191–192° C.

Step 100.3:

A mixture of 3 g (10.33 mmol) of 5-amino-1-benzyl-4-cyano-3-(3-pyridylamino)-pyrazole and 60 ml of 98% aqueous formic acid is heated under reflux for 3 hours and then concentrated by evaporation to about 113 of its original volume. After the addition of a small amount of ice, the reaction mixture is adjusted to a pH value of about 9 by the dropwise addition, with vigorous stirring, of 2N sodium hydroxide solution. Filtration and washing the filter residue with water yield 1-benzyl-4-hydroxy-3-(3-pyridylamino)-pyrazolo[3,4-d]pyrimidine having a water content of 2.8%; m.p. 150–160° C.

Step 100.4:

A mixture of 2.5 9 (7.63 mmol) of 1-benzyl-4-hydroxy-3-(3-pyridylamino)pyrazolo[3,4-d]pyrimidine and 15 ml of phosphorus oxychloride is heated under reflux for 2.5 hours and then concentrated by evaporation in vacuo. The residue is dissolved in 15 ml of methylene chloride; 2.5 ml (23.79 mmol) of 3-chloro-aniline are added to the solution and the reaction mixture is stirred at 20° C. for 15 hours. The mixture is then partitioned between methylene chloride and water and the aqueous phase is rendered basic by the addition of 1 N aqueous sodium carbonate solution. The precipitate that forms in the aqueous phase is filtered off and washed with water, yielding a first charge of 1-benzyl-4-(3-chloro-phenyl-amino)-3-(3-pyridylamino)-pyrazolo[3,4-d]pyrimidine; m.p. 165–167° C.; FAB-MS: (M+H)$^+$=428.

Further product is obtained by concentration of the organic phase by evaporation, purification of the residue by flash chromatography over silica gel having a particle size of 0.035-0.07 mm using methylene chloride and methylene chloride/methanol (49:1), concentration of the product-containing fractions by evaporation and recrystallization of the residue from ethyl acetate/hexane.

EXAMPLE 101

A mixture of 300 mg (0.782 mmol) of 3-(4-aminomethyl-phenylamino)-4-(3-chloro-phenylamino)-1H-pyrazolo[3,4-d]pyrimidine hydrate (see Step 77.5), 554 mg (6.44 mmol) of γ-butyrolactone, 6 mg of 4-dimethylamino-pyridine and 5 ml of methanol is stirred for 16 hours at 95° C. and, after a further addition of 277 mg (3.22 mmol) of γ-butyrolactone and 3 mg of 4-dimethylamino-pyridine, for a further 4 hours at 100° C. The reaction mixture is then concentrated by evaporation in vacua; 5 ml of methanol are added to the residue and the mixture is stirred at 20° C. for 5 min and filtered, and the filter residue is washed with methanol. 4-(3-Chloro-phenylamino)-3-[4-({4hydroxy-butyryl-amino}-methyl)-phenylamino]-1H-pyrazolo[3,4-d]pyrimidine, containing 0.52% water, is obtained; m.p. 215° C.

EXAMPLE 102

A mixture of 500 mg (1.303 mmol) of 3-(4-aminomethyl-phenylamino)-4-(3-chloro-phenylamino)-1H-pyrazolo[3,4-d]pyrimidine hydrate (see Step 77.5), 229 mg (1.562 mmol) of 1H-pyrazole-1-carbamidine monohydrochloride (Fluka), 202 mg (1.563 mmol) of N-ethyldiisopropylamine and 5 ml of DMF is stirred at RT for 7 hours and then concentrated by evaporation under a high vacuum. Crystallization of the residue from methanol, filtration and washing the filter residue with methanol yield 4-(3-chloro-phenyl-amino)-3-(4-{guanidino-methyl}-phenylamino)-1H-pyrazolo-[3,4-d]pyrimidine hydrochloride having a water content of 2.86%; m.p. 254–256° C.

EXAMPLE 103

A mixture of 300 mg (0.8054 mmol) of 3-(3-aminomethyl-phenylamino)4-(3-chloro-phenylamino)-1H-pyrazolo[3,4-d]pyrimidine (water content: 1.79%; see Step 90.5), 277 mg (3.22 mmol) of -γ-butyrolactone, 2 mg of 4-dimethylamino-pyridine and 5 ml of methanol is stirred for 10 hours at 95° C. and, after a further addition of 277 mg (3.22 mmol) of γ-butyrolactone and 4 mg of 4-dimethylaminopyridine, for a further 16 hours at 100° C. The reaction mixture is then concentrated by evaporation in vacuo, and the residue is stirred with ethyl acetate and filtered, and the filter residue is recrystallized from methanol, yielding 4-(3-chloro-phenylamino)-3-[3-({4-hydroxy-butyryl-amino}-methyl)-phenylamino]-1H-pyrazolo[3,4-d]pyrimidine having a water content of 0.67%; m.p. 182–184° C.

EXAMPLE 104

A mixture of 200 mg (0.537 mmol) of 3-(3aminomethyl-phenylamino)-4-(3-chloro-phenylamino)-1H-pyrazolo[3,4-d]pyrimidine (water content: 1.79%; see Step 90.5), 79 mg (0.539 mmol) of 1H-pyrazole-1-carbamidine monohydrochloride and 2 ml of DMF is stirred at RT for 65 hours and then concentrated by evaporation under a high vacuum. Crystallization of the residue from diethyl ether, filtration and washing the filter residue with diethyl ether yield 4-(3-chlorophenylamino)-3-(3-{guanidino-methyl}-phenylamino)-1H-pyrazolo[3,4-d]pyrimidine.1.05 hydrochloride having a water content of 1.76%; m.p. 270° C. (decomp.).

EXAMPLE 105

A mixture of 35 g (108.9 mmol) of 3-[2-(Boc-amino)-ethylamino]-4-cyano-5-dimethylamino-methyleneamino-pyrazole, 17.9 g (109.1 mmol) of 3-chloro-aniline hydrochloride and 350 ml of methanol is heated under reflux for 30 hours and then stirred at RT for 15 hours. Filtration and washing the filter residue with methanol yield 3-[2-(tert-butyloxy-carbonyl-amino)-ethylamino]-4-(3-chloro-phenylamino)-1H-pyrazolo[3,4-d]pyrimidine having a water content of 2.39%; m.p. 206–208° C.; ESI-MS: (M–H)$^-$=402.

The starting material is prepared as follows:

Step 105.1:

A mixture of 59.8 g (351.2 mmol) of 3,3bis-methylmercapto-2-cyano-acrylonitrile, 56.3 g (351.4 mmol) of N-Boc-ethylenediamine [for preparation see: J. Org. Chem. 60, 4305 (1995)] and 500 ml of ethyl acetate is stirred under reflux for 3 hours and then concentrated in vacuo to approximately half its original volume. The reaction mixture is cooled to 0° C.; 300 ml of diethyl ether are added and the mixture is stirred for a further 0.5 hour and filtered. After washing the filter residue with diethyl ether, 3-[2-(Boc-amino)-ethylamino]-2-cyano-3-methylmercapto-acrylonitrile is obtained; m.p. 123–125° C.

Step 105.2:

A mixture of 80.81 g (286.4 mol) of 3-[2-(Boc-amino)-ethylamino]-2-cyano-3-methylmercapto-acrylonitrile, 14.9 ml (300.7 mmol) of hydrazine hydrate and 500 ml of methanol is heated under reflux for 4 hours and then concentrated by evaporation in vacuo at about 50° C., yielding 5-amino-3-[2-(Boc-amino)-ethylamino]-4-cyano-pyrazole; TLC-R$_f$=0.27 (methylene chloride/methanol [9:1]).

Step 105.3:

A mixture of 76.3 9 (286.1 mmol) of 5-amino-3-[2-(Boc-amino)-ethylamino]-4cyano-pyrazole, 54 ml (315.1 mmol) of N,N-dimethylformamide diethyl acetal, 850 ml of toluene and 85 ml of ethanol is stirred at 100° C. for 5 hours. A further 24.5 ml (143 mmol) of N,N-dimethylformamide diethyl acetal are then added to the reaction mixture and stirring is continued for a further 3 hours at 100° C. After cooling to about 10° C., filtration and washing the filter residue with toluene and diethyl ether, 3-[2-(Boc-amino)-ethylamino]-4-cyano-5-(dimethylamino-methyleneamino)-pyrazole is obtained; m.p. 158–160° C.; ESI-MS: (M–H)$^-$=320.

EXAMPLE 106

15 g (36.25 mmol) of 3-[2-(Boc-amino)-ethylamino]-4-(3-chloro-phenylamino)-1H-pyrazolo[3,4-d]pyrimidine (water content: 2.39%; see Example 105) are dissolved in 250 ml of 3N methanolic hydrochloric acid and the reaction mixture is stirred at 20° C. for 18 hours. Subsequent filtration and washing the filter residue with methanol and diethyl ether yield 3-(2-aminoethylamino)-4-(3-chloro-phenylamino)-1H-pyrazolo[3,4-d]pyrimidine dihydrochloride having a water content of 3.31%; m.p.>260° C.

EXAMPLE 107

A mixture of 300 mg (0.983 mmol) of 3-(2-amino-ethylamino)-4-(3-chloro-phenylamino)-1H-pyrazolo[3,4-d]pyrimidine (water content: 0.48%), 257 mg (1.136 mmol) of benzoic anhydride and 5 ml of THF is stirred at RT for 1 hour and then 5 ml of diethyl ether are added. Filtration and washing the filter residue with diethyl ether yield 3-(2-benzoylamino-ethylamino)-4-(3-chloro-phenylamino)-1H-pyrazolo[3,4d]pyrimidine having a water content of 0.32%; m.p. 237–239° C.

The starting material is prepared as follows:

Step 107.1:

With intensive stirring, 35 ml of a saturated aqueous sodium carbonate solution and then 75 ml of ethyl acetate are added to a solution of 9.8 g (25.15 mmol) of 3-(2-amino-ethylamino)-4-(3-chloro-phenylamino)-1H-pyrazolo[3,4-d]pyrimidine dihydrochloride (water content: 3.31%; see Example 106) in 100 ml of water, the desired product precipitating in crystalline form. Filtration and washing the filter residue with ethyl acetate yield 3-(2-amino-ethylamino)-4-(3-chloro-phenylamino)-1H-pyrazolo[3,4-d]pyrimidine having a water content of 0.48%; m.p. 200° C.

EXAMPLE 108

The following compounds are obtained analogously to the processes described in this text:

a) 4-(3-chloro-phenylamino)-3-(4-pyridyl-amino)-1H-pyrazolo[3,4-d]pyrimidine hydrochloride (water content 5.68%)3 m.p. >260° C.; ESI-MS: (M+H)$^+$=338, b) 4-(3-chloro-phenylamino)-3-(2-formylamino-ethylamino)-1H-pyrazolo[3,4-d]pyrimidine, c) 3-(2-acetylamino-ethylamino)-4-(3-chloro-phenylamino)-1H-pyrazolo[3,4-d]pyrimidine; m.p. 245–247° C., ESI-MS: (M+H)$^+$=346, d) 4-(3-chloro-phenylamino)-3-[2-(N$^3$-phenyl-ureido)-ethylamino]-1H-pyrazolo[3,4-d]pyrimidine, e) 4-(3-chloro-phenylamino)-3-{2-[N$^3$-(3-chloro-phenyl)-ureido]-ethylamino}-1H-pyrazolo-[3,4-d]pyrimidine; m.p. 205–208° C., f) 4-(3-chloro-phenylamino)-3-{2-[N$^3$(4-chloro-phenyl)-ureido]-ethylamino}-1H-pyrazolo-[3,4-d]pyrimidine, g) 4-(3-chloro-phenylamino)-3-[2-(N$^3$-ethyl-ureido)-ethylamino]-1H-pyrazolo[3,4-d]pyrimidine (water content 0.31%); m.p. >270° C., ESI-MS: (M+H)$^+$=375, h) 4-(3-chloro-phenylamino)-3-[2-(N$^3$-methyl-thioureido)-ethylamino]-1H-pyrazolo[3,4-d]pyrimidine, m.p. >260° C.; ESI-MS: (M+H)$^+$=377, i) 4-(3-chloro-phenylamino)-3-[2-(N$^3$-phenyl-thioureido)-ethylamino]-1H-pyrazolo[3,4-d]pyrimidine (water content 1.6%); m.p. 120–122° C., ESI-MS: (M+H)$^+$=439, j) 3-[2-({N-Boc-glycyl}-amino)-ethylamino]4-(3-chloro-phenylamino)-1H-pyrazolo[3,4-d]-pyrimidine (water content 3.72%); m.p. 135° C., ESI-MS: (M+H)$^+$=461, k) 4-(3-chloro-phenylamino)-3-[2-(glycyl-amino)ethylamino]-1H-pyrazolo[3,4-d]pyrimidine.1.9 HCl (water content 8.33%); m.p. 250° C. (decomp.), ESI-MS: (M+H)$^+$=361, l) 4-(3-chloro-phenylamino)-3-(2-guanidino-ethylamino)-1H-pyrazolo[3,4-d]pyrimidine hydrochloride (water content: 4.29%), m.p. 150–153° C.; FAB-MS: (M+H)$^+$=346, m) 4-(3-chloro-phenylamino)-3-[2-(2-furoylamino)-ethylamino]-1H-pyrazolo[3,4-d]pyrimidine (water content: 7.07%), m.p. 234–236° C., ESI-MS: (M–H)$^-$=396, n) 3-[3-(Boc-amino)-propylamino]-4-(3-chloro-phenylamino)-1H-pyrazolo[3,4-d]pyrimidine, o) 3-(3-amino-propylamino)-4-(3-chloro-phenylamino)-1H-pyrazolo-[3,4-d]pyrimidine dihydrochloride, p) 4-(3-chloro-phenylamino)-3-(3-formylamino-propylamino)-1H-pyrazolo-[3,4-d]pyrimidine, q) 3-(3-acetylamino-propylamino)4-(3-chloro-phenylamino)-1H-pyrazolo-[3,4-d]pyrimidine, r) 3-[3-({N-Boc-glycyl}-amino)-propylamino]-4-(3-chloro-phenylamino)-1H-pyrazolo[3,4-d]-pyrimidine, s) 4-(3-chloro-phenylamino)-3-[3-(glycyl-amino)-propylamino]-1H-pyrazolo-[3,4-d]pyrimidine, t) 4-(3-chloro-phenylamino)-3-[3-(N$^3$-phenyl-ureido)-propylamino]-1H-pyrazolo[3,4d]pyrimidine, u) 4-(3-chloro-phenylamino)-3-[3-(N$^3$-ethyl-ureido)-propylamino]-1H-pyrazolo[3,4-d]pyrimidine, v) 4-(3-chloro-phenylamino)-3-[3-(toluene-4-sulfonylamino)-propylamino]-1H-pyrazolo[3,4-d]pyrimidine, w) 4-(3-chloro-phenylamino)-3-(3-methanesulfonylamino-propylamino)-1H-pyrazolo[3,4-d]pyrimidine, x) 4(3-chloro-phenylamino)-3(3-guanidino-propylamino)-1H-pyrazolo[3,4-d]pyrimidine, y) 3-[4-(Boc-amino)-butylamino]-4-(3chloro-phenylamino)-1H-pyrazolo[3,4-d]pyrimidine, z) 3-(4-amino-butylamino)-4-(3-chloro-phenylamino)-1H-pyrazolo[3,4-d]pyrimidine dihydrochloride, za) 4-(3-chloro-phenylamino)-3-(4-formylamino-butylamino)-1H-pyrazolo[3,4-d]pyrimidine, zb) 4-(3-chloro-phenylamino)-3-(4-acetylamino-butylamino)-1H-pyrazolo[3,4-d]pyrimidine, zc) 4-(3-chloro-phenylamino)-3-[4-(N$^3$-phenyl-ureido)-butylamino]-1H-pyrazolo[3,4-d]pyrimidine, zd) 4-(3-chloro-phenylamino)-3-[4-(N³-ethyl-ureido)-butylamino]-1H-pyrazolo[3,4-d]pyrimidine, ze) 3-[4-({N-Boc-glycyl}amino)-butylamino]-4-(3-chloro-phenylamino)-1H-pyrazolo[3,4-d]pyrimidine, zf) 4-(3-chloro-phenylamino)-3-[4-(glycyl-amino)-butylamino]1H-pyrazolo[3,4-d]pyrimidine, zg) 4-(3-chloro-phenylamino)-3-(4-guanidino-butylamino)-1H-pyrazolo[3,4-d]pyrimidine, zh) 4-(3-chloro-phenylamino)-3-(4-methanesulfonylamino-butylamino)-1H-pyrazolo[3,4-d]pyrimidine, zi) 3-(4-benzoylamino-butylamino)-4-(3chloro-phenylamino)-1H-pyrazolo[3,4-d]pyrimidine, zj) 3-(3-benzoylamino-propylamino)-4-(3-chloro-phenylamino)-1H-pyrazolo[3,4-d]pyrimidine, zk) 4-(3-chloro-phenylamino)-3-[2-(4-nitro-benzoylamino)-ethylamino]-1H-pyrazolo[3,4-d]pyrimidine; m.p. 243–245° C., ESI-MS: (M+H)⁺=453, zl) 4-(3-chloro-phenylamino)-3-[2-(3-nitro-benzoylamino)-ethylamino]-1H-pyrazolo[3,4-d]pyrimidine (water content 0.76%); m.p. 243–245° C.; ESI-MS: (M+H)⁺=453, zm) 3-[2-(4-amino-benzoylamino)-ethylamino]-4-(3-chloro-phenylamino)-1H-pyrazolo[3,4-d]pyrimidine; m.p. 236–238° C.; ESI-MS: (M+H)⁺=423, zn) 3-[2-(3-amino-benzoylamino)-ethylamino]4-(3-chloro-phenylamino)-1H-pyrazolo[3,4-d]-pyrimidine (water content 3.69%); m.p. 236–238° C.; ESI-MS: (M+H)⁺=423, zo) (R)-3-[4-(dimethylamino-carbonylamino-methyl)-phenylamino]-4-(1-phenyl-ethylamino)-1H-pyrazolo[3,4-d]pyrimidine, zp) (S)-3-[4-(dimethylamino-carbonylamino-methyl)-phenylamino]-4-(1-phenyl-ethylamino)-1H-pyrazolo[3,4-d]pyrimidine, and zq) (R)-3-[3-(dimethylamino-carbonylamino-methyl)-phenylamino]-4-(1-phenyl-ethylamino) 1H-pyrazolo[3,4-d]pyrimidine.

EXAMPLE 109

The following compounds are obtained analogously to the processes described in this text:

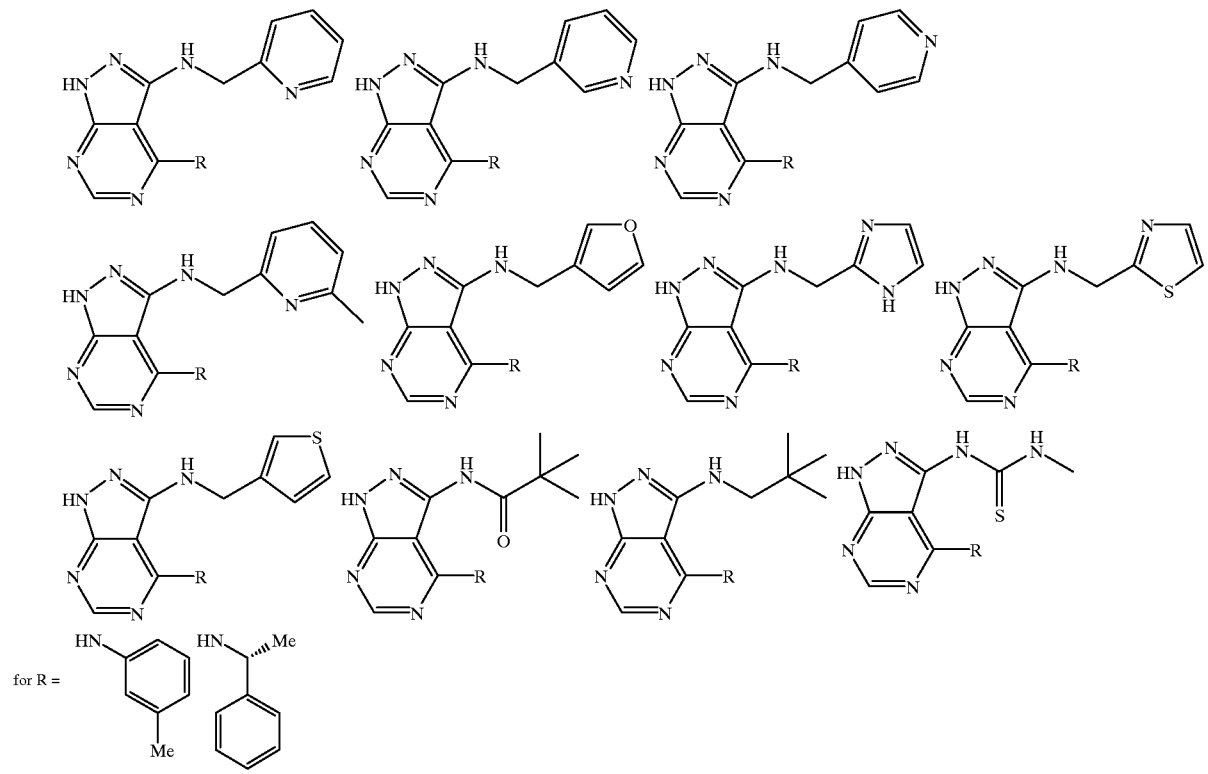

EXAMPLE 110

The following compounds are obtained analogously to the processes described in this text:

a) (S)-3-[3-(dimethylamino-carbonylamino-methyl)-phenylamino]-4-(1-phenyl-ethylamino)-1H-pyrazolo[3,4-d]pyrimidine (cf. Example 108zq), and b) 4(3-chloro-phenylamino)-3-(2-propionylaminothylamino)-1H-pyrazolo[3,4-d]pyrimidine; m.p. 240–242° C.; ESI-MS: (M+H)⁺=360.

EXAMPLE 111

4-(3-Chloro-phenylamino)-3-(2-ureido-ethylamino)-1H-pyrazolo[3,4-d]-pyrimidine (CGP79331)

A mixture of 200 mg (0.655 mmol) of 3-(2-amino-ethylamino)-4-(3-chloro-phenylamino)-1H-pyrazolo[3,4-d]pyrimidine (water content: 0.48%), 72 mg (0.887 mmol) of potassium cyanate, 1.2 ml of ethanol, 1.2 ml of water and 46.8 ml (0.819 mmol) of acetic acid is stirred at RT for 15 hours. 2 ml of water are added to the resulting suspension and the mixture is filtered. Washing the filter residue with water and a small amount of ethanol and drying in vacuo (about 100 mbar, 8 hours, 100C) yield the title compound having a water content of 5.54%; m.p. 212–214° C.; ESI-MS: (M+H)⁺=347

EXAMPLE 112
Dry-Filled Capsules 5000 capsules, each comprising as active ingredient 0.25 g of one of the compounds of formula I mentioned in the preceding Examples, are prepared as follows:

| Composition | |
|---|---|
| active ingredient | 1250 g |
| talcum | 180 g |
| wheat starch | 120 g |
| magnesium stearate | 80 g |
| lactose | 20 g |

Preparation Method:

The powdered substances listed above are pressed through a sieve of 0.6 mm mesh size. 0.33 9 portions of the mixture are introduced into gelatin capsules using a capsule-filling machine.

EXAMPLE 113
Soft Capsules 5000 soft gelatin capsules, each comprising as active ingredient 0.05 g of one of the compounds of formula I mentioned in the preceding Examples, are prepared as follows:

| Composition | |
|---|---|
| active ingredient | 250 g |
| PEG 400 | 1 litre |
| Tween 80 | 1 litre |

Preparation Method:

The powdered active ingredient is suspended in PEG 400 (polyethylene glycol having an M, of from about 380 to about 420, Fluka, Switzerland) and Tween® 80 (polyoxyethylene sorbitan monolaurate, Atlas Chem. Ind., Inc., USA, supplied by Fluka, Switzerland) and ground to a particle size of about 1 to 3 μm in a wet pulverizer. 0.43 g portions of the mixture are then introduced into soft gelatin capsules using a capsule-filling machine.

What is claimed is:
1. A compound of formula I

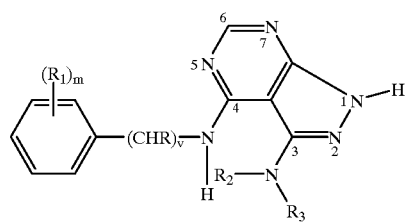

(I)

wherein m is an integer from 0 up to and including 3,
  v is 0 or 1,
  R is hydrogen or lower alkyl,
  $R_1$ is halogen, cyano, amino, lower alkanoylamino, lower alkylamino, N,N-di-lower alkylamino, hydroxy, lower alkoxy, lower alkanoyloxy, carboxy, lower alkoxycarbonyl, carbamoyl, N-lower alkyl-carbamoyl, N,N-di-lower alkyl-carbamoyl, or lower alkyl that is unsubstituted or substituted by halogen, cyano, amino, lower alkanoylamino, lower alkylamino, N,N-di-lower alkylamino, hydroxy, lower alkoxy, lower alkanoyloxy, carboxy, lower alkoxycarbonyl, carbamoyl, N-lower alkyl-carbamoyl or by N,N-di-lower alkyl-carbamoyl, it being possible when several phenyl substituents $R_1$ are present for those substituents to be identical or different from one another, and
  a) $R_2$ is hydrogen and $R_3$ is
    α) a radical of formula II

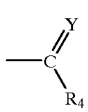

(II)

wherein Y is oxygen or sulfur and
  $R_4$ is
    αα) an alkyl radical that is unsubstituted or substituted by amino, lower alkanoylamino, benzoylamino, benzyloxycarbonylamino, lower alkoxycarbonylamino, phenylamino or by benzylamino and that contains, including the substituents, from 4 to 20 carbon atoms,
    αβ) phenylamino, benzylamino, naphthylamino or pyridylmethylamino, or alkylamino having from 4 to 11 carbon atoms, or
    αγ) phenyl, or monocyclic heterocyclyl bonded via a carbon atom and having 5 or 6 ring members and from 1 to 4 ring hetero atoms selected from nitrogen, oxygen and sulfur, any phenyl radicals present in the radical $R_4$ being unsubstituted or substituted by one or more radicals selected from nitro, amino, lower alkanoylamino, lower alkylamino, di-lower alkylamino, halogen, cyano, trifluoromethyl, hydroxy, lower alkoxy, lower alkanoyloxy, carboxy, lower alkoxycarbonyl, carbamoyl, N-lower alkyl-carbamoyl, methylenedioxy and lower alkyl, it being possible when several phenyl substituents are present for those substituents to be identical or different from one another,
  β) lower alkyl substituted by
    βα) unsubstituted or lower-alkyl-substituted monocyclic heterocyclyl bonded via a ring carbon atom and having 5 or 6 ring members and from 1 to 4 ring hetero atoms selected from nitrogen, oxygen and sulfur,
    ββ) phenyl substituted by
      i) phenyl,
      ii) unsubstituted or chloro-substituted phenoxy or
      iii) unsubstituted or lower-alkyl-substituted monocyclic heterocyclyl having 5 or 6 ring members and from 1 to 4 ring hetero atoms selected from nitrogen, oxygen and sulfur,
    βγ) naphthyl,
    βδ) cycloalkyl having from 3 to 8 ring members that is unsubstituted or substituted by lower alkyl or by lower alkoxycarbonyl, or
    βε) lower alkanoylamino, benzyloxycarbonylamino, lower alkoxycarbonylamino, benzoylamino, phenylamino, benzylamino, ureido, N³phenyl-ureido, $N^3$-lower alkyl-ureido, $N^3,N^3$-di-lower alkyl-ureido, amino-lower alkanoylamino, (lower alkoxycarbonylamino-lower alkanoyl)-amino, (benzyloxycarbonylamino-lower alkanoyl)-amino, prolyl-amino, (N-lower alkoxycarbonyl-propylamino, $N^3$-lower alkyl-thioureido, $N^3$-phenyl-thioureido, cyano, guanidino, amidino, toluenesulfonylamino, lower alkanesulfonylamino or unsubstituted or lower-alkyl-substituted monocyclic heterocyclylcarbonylamino having 5 or 6 ring members and from 1 to 4 ring hetero atoms selected from nitrogen, oxygen and sulfur, radicals mentioned in section OF) that contain a phenyl radical being unsubstituted or substituted in the phenyl radical by halogen, cyano, nitro, amino, lower alkanoylamino, lower alkylamino, N,N-di-lower alkylamino, hydroxy, lower alkoxy, lower alkanoyloxy, carboxy, lower alkoxycarbonyl, carbamoyl, N-lower alkyl-carbamoyl, N,N-di-lower alkyl-carbamoyl or by lower alkyl, or γ) a radical of formula III

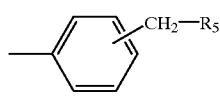

(III)

wherein $R_5$ is carboxy-lower alkanoylamino, benzyloxycarbonylamino, ureido, $N^3$-phenyl-ureido, $N^3$-(chloro-phenyl)-ureido, $N^3$-(lower alkoxy-phenyl)-ureido, $N^3$-lower alkyl-ureido, $N^3,N^3$-di-lower alkyl-ureido, $N^3$-lower alkyl-thioureido, amino-lower alkanoyl-amino, (lower alkoxycarbonylamino-lower alkanoyl)-amino, (benzyloxycarbonylamino-lower alkanoyl)-amino, prolyl-amino, (N-lower alkoxycarbonyl-prolyl)-amino, hydroxy-lower alkanoyl-amino, di-lower alkylamino-methyleneamino, succinimido, phthalimido, guanidino or amidino, δ) unsubstituted or lower-alkyl-substituted monocyclic heterocyclyl bonded via a ring carbon atom and having 5 or 6 ring members and from 1 to 4 ring hetero atoms selected from nitrogen, oxygen and sulfur, or ε) lower alkanesulfonyl or unsubstituted or lower-alkyl-substituted benzenesulfonyl, or b) $R_2$ and $R_3$ together are
di-lower alkylamino-methyleneamino, or a substituted or unsubstituted alkylene or alkenylene radical having up to 15 carbon atoms, wherein from 1 to 3 carbon atoms may have been replaced by oxygen, sulfur or nitrogen, or a salt, solvate or tautomer thereof.

2. A derivative of formula I according to claim 1, wherein
m is an integer from 0 up to and including 3,
v is 0 or 1,
R is hydrogen or lower alkyl,
$R_1$ is halogen, or lower alkyl that is unsubstituted or substituted by halogen, cyano, amino, lower alkanoylamino, lower alkylamino, N,N-di-lower alkylamino, hydroxy, lower alkoxy, lower alkanoyloxy, carboxy, lower alkoxycarbonyl, carbamoyl, N-lower alkyl-carbamoyl or by N,N-di-lower alkyl-carbamoyl, it being possible when several phenyl substituents $R_1$ are present for those substituents to be identical or different from one another, and a) $R_2$ is hydrogen and $R_3$ is
α) a radical of formula II

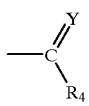

(II)

wherein Y is oxygen or sulfur and
$R_4$ is
αα) an alkyl radical that is substituted by lower alkanoylamino, benzoylamino, benzyloxycarbonylamino, lower alkoxycarbonylamino, phenylamino or by benzylamino and that contains, including the substituents, from 4 to 20 carbon atoms, αβ) phenylamino, benzylamino, naphthylamino or pyridylmethylamino, or αγ) phenyl, or monocyclic heterocyclyl bonded via a ring carbon atom, selected from furyl, thienyl and pyridyl,
any phenyl radicals present in the radical $R_4$ being unsubstituted or substituted by one or more radicals selected from nitro, amino, lower alkanoylamino, lower alkylamino, di-lower alkylamino, halogen, cyano, trifluoromethyl, hydroxy, lower alkoxy, lower alkanoyloxy, carboxy, lower alkoxycarbonyl, carbamoyl, N-lower alkyl-carbamoyl, methylenedioxy and lower alkyl, it being possible when several phenyl substituents are present for those substituents to be identical or different from one another, β)lower alkyl substituted by
βα) unsubstituted or lower-alkyl-substituted monocyclic heterocyclyl bonded via a ring carbon atom, selected from pyridyl, thienyl, thiazolyl, pyrrolyl, imidazolyl, furyl and tetrazolyl, ββ) phenyl substituted by
i) phenyl,
ii) unsubstituted or chlorosubstituted phenoxy or
iii) unsubstituted or lower-alkyl-substituted monocyclic heterocyclyl bonded via a ring carbon atom, selected from tetrazolyl, pyridyl and thiazolyl, βγ) naphthyl,
βδ) cycloalkyl having from 3 to 8 ring members that is unsubstituted or substituted by lower alkyl or by lower alkoxycarbonyl, or βε) lower alkanoylamino, benzyloxycarbonylamino, lower alkoxycarbonylamino, benzoylamino, phenylamino, benzylamino, ureido, $N^3$phenyl-ureido, $N^3$-lower alkyl-ureido, $N^3,N^3$-di-lower alkyl-ureido, amino-lower alkanoylamino, (lower alkoxycarbonylamino-lower alkanoylamino, (benzyloxycarbonylamino-lower alkanoyl)-amino, prolyl-amino, (N-lower alkoxycarbonyl-prolyl)-amino, $N^3$-lower alkyl-thio ureido, $N^3$-phenyl-thioureido, cyano, guanidino, amidino, toluenesulfonylamino, lower alkanesulfonylamino or furoylamino, radicals mentioned in section O) that contain a phenyl radical being unsubstituted or substituted in the phenyl radical by halogen, cyano, nitro, amino, lower alkanoylamino, lower alkylamino, N,N-di-lower alkylamino, hydroxy, lower alkoxy, lower alkanoyloxy, carboxy, lower alkoxycarbonyl, carbamoyl, N-lower alkyl-carbamoyl, N,N-di-lower alkyl-carbamoyl or by lower alkyl, or γ) a radical of formula III

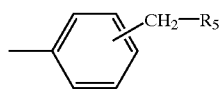

(III)

wherein R₅ is carboxy-lower alkanoylamino, benzyloxycarbonylamino, ureido, $N^3$-phenyl-ureido, $N^3$-(chloro-phenyl)-ureido, $N^3$-(lower alkoxy-phenyl) ureido, $N^3$-lower alkyl-ureido, $N^3,N^3$-di-lower alkyl-ureido, $N^3$-lower alkyl-thioureido, amino-lower alkanoyl-amino, (lower alkoxycarbonylamino-lower alkanoyl)-amino, (benzyloxycarbonylamino-lower alkanoyl)amino, prolyl-amino, (N-lower alkoxycarbonyl-prolyl)-amino, hydroxy-lower alkanoyl-amino, di-lower alkylamino-methyleneamino, succinimido, phthalimido, guanidino or amidino, δ) pyridyl, or ε) lower alkanesulfonyl or unsubstituted or lower-alkyl-substituted benzenesulfonyl, or b) $R_2$ and $R_3$ together are di-lower alkylamino-methyleneamino, 1,2-ethylene, propane-1,3-diyl, butane-1,4-diyl, pentane-1,5-diyl, 3-(3-amino-propionyl)-3-aza-pentane-1,5-diyl, 2-amino-butane-1,4-diyl, 1-aminomethyl-butane-1,4-diyl, 1-hydroxymethyl-butane-1,4-diyl, 3-hydroxy-pentane-1,5-diyl, 1-hydroxy-hexane-1,5-diyl, 3-(2-aminoethyl)-pentane-1,5-diyl, 3-aza-pentane-1,5-diyl (—CH₂—CH₂NH—CH₂—CH₂—), 3-aza-2,4-dimethyl-pentane-1,5diyl (—CH₂—CH[CH₃]—NH—CH[CH₃]—CH₂—), 3-amino-3-aza-pentane-1,5-diyl (—CH₂—CH₂—N[NH₂]—CH₂—CH₂—), 1-aza-pentane-1,5-diyl, 1-aza-1-toluylaminocarbonyl-pentane-1,5-diyl, 1-aza-1-(methylamino-thiocarbonyl)-pentane-1,5-diyl, 1-aza-1-(tert-butylamino-carbonyl)-pentane-1,5-diyl, 1-aza-1-(cyclohexylamino-carbonyl)-pentane-1,5-diyl, 3-aza-1-hydroxy-heptane-3,7-diyl, 3-aza-1-cyano-heptane-3,7-diyl, 1-amino-3-aza-heptane-3,7-diyl, 3-(2-amino-ethyl)-3-aza-pentane-1,5-diyl (—CH₂—CH₂—N[—CH₂—CH₂—NH₂]—CH₂—CH₂—), 1-carbamoyl-butane-1,4-diyl, 2-formylamino-pentane-1,4-diyl, 2-aza-butadiene-1,4-diyl (—CH=CH—N=CH—), 2-aza-3-hydroxymethyl-butadiene-1,4-diyl (—CH=C[CH₂OH]—N=CH—), 2-aza-1-hydroxy-1-(4-methoxy-phenyl-amino)-heptane-2,7-diyl {-(CH₂)₄-N[—CH(OH)—NH—C₆H₄—OCH₃]—}, 3-oxa-pentane-1,5-diyl, N-lower alkoxycarbonyl-3-aza-pentane-1,5-diyl, N—(C₁-C₁₂alkanoyl)-3-aza-pentane-1,5-diyl, N-benzoyl-3-aza-pentane-1,5-diyl or N-(pyrid-2-yl-carbonyl)-3-aza-pentane-1,5-diyl, or a salt, solvate or tautomer thereof.

3. A derivative of formula I according to claim 1, wherein m is an integer from 0 up to and including 2, v is 0 or 1, R is hydrogen or lower alkyl, R. is halogen or lower alkyl, it being possible when several phenyl substituents $R_1$ are present for those substituents to be identical or different from one another, and a) $R_2$ is hydrogen and $R_3$ is α) a radical of formula II

(II)

wherein Y is oxygen or sulfur and $R_4$ is

αα) unsubstituted $C_4$–$C_7$alkyl or a lower alkyl radical that is or substituted by lower alkanoylamino, benzoylamino, benzyloxycarbonylamino, lower alkoxycarbonylamino, phenylamino or by benzylamino and that contains, including the substituents, from 4 to 20 carbon atoms, αβ) phenylamino, benzylamino, naphthylamino or pyridylmethylamino, or αγ) phenyl, or monocyclic heterocyclyl bonded via a ring carbon atom, selected from furyl, thienyl and pyridyl, any phenyl radicals present in the radical $R_4$ being unsubstituted or substituted by one or more radicals selected from halogen, methylenedioxy and lower alkyl, H being possible when several phenyl substituents are present for those substituents to be identical or different from one another, β) lower alkyl substituted by βα) unsubstituted or lower-alkyl-substituted monocyclic heterocyclyl that is bonded via a ring carbon atom and selected from pyridyl, thienyl, thiazolyl, pyrrolyl, imidazolyl, furyl and tetrazolyl, ββ) phenyl substituted by i) phenyl, ii) unsubstituted or chloro-substituted phenoxy or iii) unsubstituted or lower-alkyl-substituted monocyclic heterocyclyl that is bonded via a ring carbon atom and selected from tetrazolyl, pyridyl and thiazolyl, βγ) naphthyl, βδ) cycloalkyl having from 3 to 8 ring members that is unsubstituted or substituted by lower alkyl or by lower alkoxycarbonyl, or βε) lower alkanoylamino, benzyloxycarbonylamino, lower alkoxycarbonylamino, benzoylamino, phenylamino, benzylamino, ureido, $N^3$-phenyl-ureido, $N^3$-lower alkyl-ureido, $N^3,N^3$-di-lower alkyl-ureido, amino-lower alkanoylamino, (lower alkoxycarbonylamino-lower alkanoyl)-amino, (benzyloxycarbonylamino-lower alkanoyl)-amino, prolyl-amino, (N-lower alkoxycarbonyl-prolyl)-amino, $N^3$-lower alkyl-thioureido, $N^3$-phenyl-thioureido, cyano, guanidino, amidino, toluenesulfonylamino, lower alkanesulfonylamino or turoylamino, radicals mentioned in section βε) that contain a phenyl radical being unsubstituted or substituted in the phenyl radical by halogen, nitro, amino, lower alkylamino, N,N-di-lower alkylamino or by lower alkyl, or γ) a radical of formula III

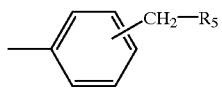
(III)

wherein $R_5$ is carboxy-lower alkanoylamino, benzyloxycarbonylamino, ureido, $N^3$-phenyl-ureido, $N^3$-(chloro-phenyl)-ureido, $N^3$-(lower alkoxy-phenyl)-ureido, $N^3$-lower alkyl-ureido, $N^3,N^3$-di-lower alkyl-ureido, $N^3$-lower alkyl-thioureido, amino-lower alkanoyl-amino, (lower alkoxycarbonylamino-lower alkanoyl)-amino, (benzyloxycarbonylamino-lower alkanoyl)amino, prolyl-amino, (N-lower alkoxycarbonyl-prolyl)-amino, hydroxy-lower alkanoyl-amino, di-lower alkylamino-methyleneamino, succinimido, phthalimido, guanidino or amidino, δ) pyridyl, or ε) lower alkanesulfonyl or unsubstituted or lower-alkyl-substituted benzenesulfonyl, or b) $R_2$ and $R_3$ together are di-lower alkylamino-methyleneamino, 3oxa-pentane-1,5-diyl, N-lower alkoxycarbonyl-3-aza-pentane-1,5-diyl, N—($C_1$–$C_{12}$alkanoyl)-3-aza-pentane-1,5-diyl, N-benzoyl-3-aza-pentane-1,5-diyl or N-(pyrid-2-yl-carbonyl)-3-aza-pentane-1,5-diyl, or a salt, solvate or tautomer thereof.

4. 4-(3-Chloro-phenylamino)-3-[(pyrid-3-yl)-methylamino]-1H-pyrazolo [3,4]pyrimidine or a pharmaceutically acceptable salt thereof according to claim 1.

5. 4-(3-Chloro-phenylamino)-3-(4-{ureido-methyl}-phenylamino)-1H-pyrazolo[3,4d]pyrimidine or a pharmaceutically acceptable salt thereof according to claim 1.

6. 4-(3-Chloro-phenylamino)-3-(3-pyridylamino)-1H-pyrazolo[3,4-d]pyrimidine or a pharmaceutically acceptable salt thereof according to claim 1.

7. 4-(3-Chloro-phenylamino)-3-[(pyrid-4-yl)-methylamino]-1H-pyrazolo[3,4-d]pyrimidine or a pharmaceutically acceptable salt thereof according to claim 1.

8. A process for the preparation of a compound of formula I according to claim 1 or of a salt, solvate or tautomer thereof, wherein a) a compound of formula IV

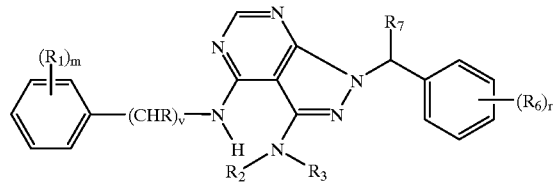
(IV)

wherein $R_7$ is hydrogen or methyl, $R_6$ is alkoxy having from 1 to 3 carbon atoms or nitro, r is an integer from 0 to 2, and the other substituents and symbols are as defined above, is treated with a suitable Lewis acid, and, if desired, a compound of formula I obtainable in accordance with process a) is converted into its salt, or a resulting salt of a compound of formula I is converted into the free compound.

9. A pharmaceutical composition comprising a pharmaceutically acceptable carrier or diluent and a therapeutically effective amount of a compound of formula I according to claim 1, or a pharmaceutically acceptable salt thereof.

10. A method of treating tumors which are responsive to an inhibition of the tyrosine kinase activity of the receptor for EGF comprising administering to a warm-blooded animal in need of such treatment a therapeutically effective amount of a compound of formula I according to claim 1, or a pharmaceutically acceptable salt thereof.

11. A method according to claim 10 wherein the warm-blooded animal is a human.

* * * * *